United States Patent
Zou et al.

(10) Patent No.: US 9,890,199 B2
(45) Date of Patent: Feb. 13, 2018

(54) STAPHYLOCOCCUS AUREUS SPA5 MUTANT, COMPOSITION COMPRISING MUTANT AND PREPARATION METHOD AND USE THEREOF

(71) Applicants: OLYMVAX BIOPHARMACEUTICALS INC., Chengdu, Sichuan (CN); THIRD MILITARY MEDICAL UNIVERSITY, PLA, Chongqing (CN)

(72) Inventors: Quanming Zou, Chongqing (CN); Hao Zeng, Chongqing (CN); Shaowen Fan, Chongqing (CN); Lu Lu, Chongqing (CN); Qiang Feng, Chongqing (CN); Jinyong Zhang, Chongqing (CN); Haiming Jing, Chongqing (CN); Yandong Dong, Chongqing (CN); Yi Wu, Chongqing (CN); Changzhi Cai, Chongqing (CN)

(73) Assignees: Olymvax Biopharmaceuticals Inc., Chengdu (CN); Third Military Medical University, PLA, Chongqing (CN)

( * ) Notice: Subject to any disclaimer, the term of this patent is extended or adjusted under 35 U.S.C. 154(b) by 0 days.

(21) Appl. No.: 15/103,173

(22) PCT Filed: Dec. 9, 2013

(86) PCT No.: PCT/CN2013/088880
§ 371 (c)(1),
(2) Date: Jun. 9, 2016

(87) PCT Pub. No.: WO2015/085463
PCT Pub. Date: Jun. 18, 2015

(65) Prior Publication Data
US 2016/0304566 A1 Oct. 20, 2016

(51) Int. Cl.
*C07K 14/31* (2006.01)
*A61K 39/085* (2006.01)
(Continued)

(52) U.S. Cl.
CPC ............ *C07K 14/31* (2013.01); *A61K 39/085* (2013.01); *A61K 39/40* (2013.01); *C07K 16/12* (2013.01);
(Continued)

(58) Field of Classification Search
CPC .............................. A61K 39/085; A61K 38/04
(Continued)

(56) References Cited

FOREIGN PATENT DOCUMENTS

| EP | 0284368 A1 | 9/1988 |
|---|---|---|
| WO | 2011005341 A2 | 1/2011 |
| WO | 2012003474 A2 | 1/2012 |

OTHER PUBLICATIONS

Kim et al., Nontoxigenic Protein A Vaccine for Methicillin-resistant *Staphylococcus aureus* Infections in Mice, Journal of Experimental Medicine, Aug. 30, 2010 (Aug. 30, 2010), No. 9, vol. 207, ISSN: 0022-1007, pp. 1863-1870, see the entire text.*
(Continued)

*Primary Examiner* — Jana A Hines
(74) *Attorney, Agent, or Firm* — Calfee, Halter & Griswold LLP

(57) ABSTRACT

Provided is staphylococcus protein A expressed by a mutational *Staphylococcus aureus* and its coding sequence, as well as a vector, host bacteria, composition or kit which contains the coding sequence of the mutational protein. Also provided is the use of the mutational protein and the composition thereof in the preparation of vaccines, therapeutic antibodies, diagnostic kits and the like, and for the prevention, treatment and detection of infections by *Staphylococ-*
(Continued)

*cus aureus*. Also provided are methods for producing, fermenting and purifying the mutational protein.

13 Claims, 28 Drawing Sheets

(51) Int. Cl.
*G01N 33/569* (2006.01)
*A61K 39/40* (2006.01)
*C07K 16/12* (2006.01)
*C12N 15/70* (2006.01)
*A61K 39/00* (2006.01)

(52) U.S. Cl.
CPC .......... *C07K 16/1271* (2013.01); *C12N 15/70* (2013.01); *G01N 33/56938* (2013.01); *A61K 2039/55505* (2013.01); *A61K 2039/575* (2013.01); *C07K 2319/00* (2013.01); *G01N 2333/31* (2013.01); *G01N 2469/20* (2013.01); *G01N 2800/26* (2013.01)

(58) Field of Classification Search
USPC ......... 424/130.1, 150.1, 184.1, 185.1, 234.1, 424/237.1
See application file for complete search history.

(56) References Cited

OTHER PUBLICATIONS

Extended European Search Report from European Application No. 13899076.7 dated Jun. 21, 2017.

Falugi et al., "Role of Protein A in the Evasion of Host Adaptive Immune Responses by *Staphylococcus aureus*," mbio.asm.org, vol. 4, Issue 5, Sep./Oct. 2013, 9 pages.

Kobayashi et al., "*Staphylococcus aureus* Protein A Promotes Immune Suppression," mbio.asm.org, vol. 4, Issue 5, Sep./Oct. 2012, 3 pages.

Kim et al., "Nontoxigenic Protein A Vaccine for Methicillin-Resistant *Staphylococcus aureus* Infections in Mice," J. Exp. Med., vol. 207 No. 9, Aug. 30, 2010, pp. 1863-1870.

International Search Report and Written Opinion from PCT/CN2013/088880 dated Sep. 26, 2014.

Kim et al. Nontoxigenic protein A vaccine for methicillin-resistant *Staphylococcus aureus* infections in mice, Journal of Experimental Medicine, Aug. 30, 2010, vol. 207, No. 9, pp. 1863-1870.

Gu et al., "Therapeutic Antibody Drugs on the Control of Methicillin-resistant *Staphylococcus aureus*," China Biotechnology, vol. 32, No. 2, Feb. 15, 2012, pp. 96-99. English Abstract attached.

* cited by examiner

STAPHYLOCOCCUS AUREUS SPA5 MUTANT, COMPOSITION COMPRISING MUTANT AND PREPARATION METHOD AND USE THEREOF

CROSS-REFERENCE TO RELATED APPLICATIONS

This application is a National Phase Application of International Application PCT/CN2013/088880, with an international filing date of Dec. 9, 2013, the entire contents of which is incorporated herein by reference.

FIELD OF THE INVENTION

The present invention relates to the field of biotechnology, and particularly to Staphylococcal protein A (SpA) expressed by *Staphylococcus aureus* (SA), and more particularly, to a mutant protein of SpA and the preparation method thereof, and its use in vaccine formulation.

BACKGROUND OF THE INVENTION

*Staphylococcus aureus* (SA) is also called "flesh-eating bacteria". As a representative of gram-positive bacteria, SA is an important pathogen causing infections in hospitals and communities. SA infection is characterized by acuteness and purulency. Local infection may lead to purulent infections of skins and soft tissues etc, which are unhealed for a long period of time. Systemic infection may result in severe infections such as osteomyelitis, septic arthritis, endocarditis, pneumonia, septicopyemia and the like, and complications. The mortality rate of severe infections and the complications thereof is as high as 20%. Furthermore, exotoxins of *Staphylococcus aureus* will also give rise to fatal systemic infections, such as food poisoning, scalded skin syndrome and toxic shock syndrome etc.

With wide and long-term use of antibiotics, bacterial drug resistance is increasingly severe. As a typical representative, methicillin-resistant *Staphylococcus aureus* (MRSA) has become one of the pathogens with the highest hospital infection rate, such as ICU infection, post-operation infection, infection of burn wounds or infection of war wounds etc, since it was first found in 1961. Additionally, MRSA has also become difficulties in clinical treatment, due to its strong pathogenicity, wide transmission, easy outbreak and epidemicity, and multiple-drug resistance, MRSA is also called "the first super bacteria".

As reported by CDC of the United States, the average annual population of severe MRSA infections is about 90,000 in America, in which about 20,000 patients die. As shown by Report of the National Bacterial Resistance Surveillance of China in 2011: the average clinical detection rate of MRSA is 60%, in which the extensive drug-resistance rate is more than 40%. Currently, MRSA, together with hepatitis B and AIDS, become three major refractory infectious diseases all over the world, and MRSA takes the first place on the list. At present, vancomycin is the last effective medicine for MRSA infections. However, vancomycin-resistant MRSA has already appeared since 1997, and has overspread globally, leading to a challenge of "no effective medicine" for MRSA infections.

Due to the severe challenge of "no effective medicine" for drug-resistant SA infections, "a package plan of 6 policies" has been proposed by WHO in 2011 to address "drug-resistant bacteria", and priority will be given to research and development of novel products for immunological prevention and treatment, such as inventive vaccines in the future. Accordingly, for effectively controlling the spread of drug resistance of SA and wide SA infections in clinical practice, it is strategically and practically important to study the immunological prevention and treatment of SA infections, and to develop safe, effective and novel gene engineering vaccines for SA.

SUMMARY OF THE INVENTION

An object of the present invention is to provide an SpA5 mutant of SA, and a composition comprising the mutant, as a novel candidate for SA vaccine.

In the first aspect of the invention, there is provided an SpA5 protein, wherein the amino acid sequence of the protein is selected from SEQ ID NO. 1-4.

In the second aspect of the invention, there is provided a nucleotide sequence encoding the SpA5 protein of the invention, wherein the nucleotide sequence is selected from SEQ ID NO. 9-12, and a vector and a host comprising the nucleotide sequence.

In the third aspect of the invention, there is provided a method for preparing the SpA5 protein of the invention.

In the fourth aspect of the invention, there is provided a method for fermentation of the host comprising SpA5 to prepare the SpA5 protein.

In the fifth aspect of the invention, there is provided a method for purification of the SpA5 protein of the invention.

In the sixth aspect of the invention, there is provided the use of the SpA5 protein of the invention as an antigen, and the use of the SpA5 protein in preparation of a formulation for detection, prevention or treatment of SA infections.

In the seventh aspect of the invention, there is provided a polyclonal antibody generated by immunization using the SpA5 protein of the invention, and the use of the polyclonal antibody in preparation of a formulation for detection, prevention or treatment of SA infections.

In the eighth aspect of the invention, there is provided a composition or a kit comprising the SpA5 protein of the invention, and preferably, the composition is a vaccine.

In the ninth aspect of the invention, there is provided a method for preparing the composition comprising the SpA5 protein of the invention.

In the tenth aspect of the invention, there is provided the use of the composition comprising the SpA5 protein of the invention in preparation of a formulation for detection, prevention or treatment of SA infections.

In the eleventh aspect of the invention, there is provided a method for detecting the contents of individual antigens in the composition comprising the SpA5 protein of the invention.

In the twelfth aspect of the invention, there is provided a method for detection, prevention or treatment of SA infections, including the use of the SpA5 protein of the invention or the composition comprising the SpA5 protein.

Based on the experiment results, protective immune response can be effectively triggered in a body by using the SpA5 protein of the invention as an antigen or using the composition comprising the SpA5 protein, so as to protect against *Staphylococcus aureus* infection with the advantages such as strong immunogenicity, safety and nontoxicity, high efficacy and quality controllable.

DETAILED DESCRIPTION OF THE INVENTION

Figure 1:
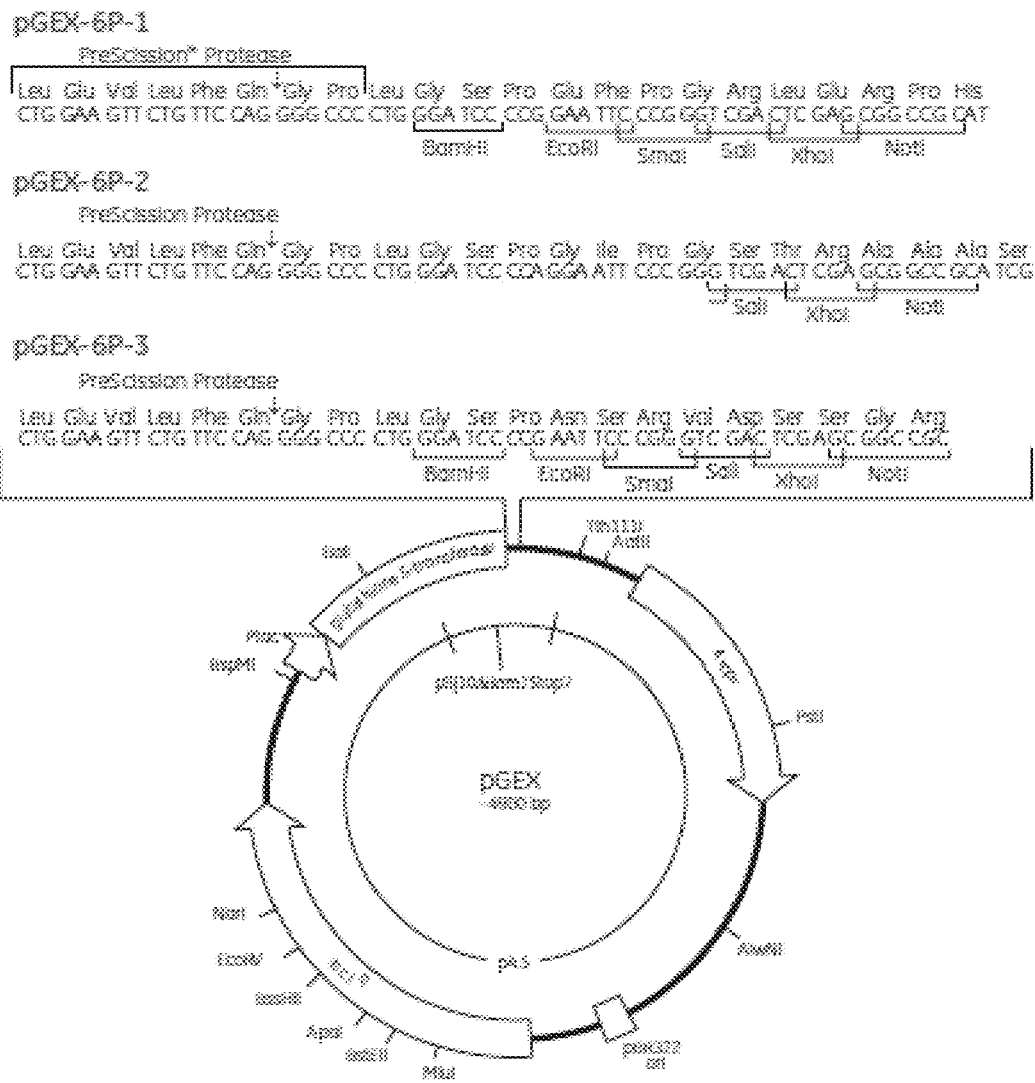
FIG. 1 is the map of pGEX vector.

The present invention will be described in detail with respect to the following particular embodiments, but the invention is not limited thereto.

A. SpA5 Mutant

SpA can be expressed by most clinical SA isolates. SA has a molecular weight of 55 kDa, and locates on the cell wall. The precursor of SpA contains an N-terminal signal peptide and a C-terminal screening signal, allowing SpA covalently bound to the cell wall. The N-terminal segment of the mature peptide contains 5 Ig binding domains consisting of 56-61 amino acid residues, which further wind into 3 α-helix bundles. These domains can bind mammalian IgG, and destroy antibody opsonophagocytosis; the domains also can bind VH3-type B cell receptors, leading to the death of B-cells, followed by breaking down acquired and innate immune response. Accordingly, it is an important choice for the anti-MRSA vaccines to induce anti-SpA antibodies in a body, block immunologic escape mechanism of MRSA. However, the intended objective can not be implemented by using natural SpA as an antigen, due to its binding capacity to antibodies. Accordingly, mutant SpA is demanded, which removes its antibody binding capacity and retains its immunogenicity.

The precursor of SpA protein of ATCC international standard strain MRSA 252 of *Staphylococcus aureus* (named as SpA (252), SEQ ID NO:5) includes 516 amino acids, in which the first 36 amino acids constitute a signal peptide sequence, and the amino acids at position 37-327 form 5 Ig binding domains including EDABC, having totally 291 amino acids (named as SpA (252). Ig binding domain is an active region of SpA, and also the research highlight. In order to obtain highly immunoreactive vaccines, mutation has been performed to Ig binding domains of the SpA from *S. aureus* Newman strain, and a certain effect has been brought about, as described in Kim H K et al. (Nontoxigenic protein A vaccine for methicillin-resistant *Staphylococcus aureus* infections in mice. J Exp Med. 2010 Aug. 30; 207(9):1863-70).

Based on the prior art, Ig binding domains of the SpA protein in ATCC international standard strain of *Staphylococcus aureus* MRSA252 have been cloned and mutated in the present invention. After activity assay, it has been found that the SpA5 protein of the invention has higher activity than that of the SpA mutant protein provided in the reference.

In the present invention, 43Q, 44Q, 96Q, 97Q, 162Q, 163Q, 220Q, 221Q, 278Q, and 279Q of SpA (252) have been replaced by K or R at the same time, and 70D, 71D, 131D, 132D, 189D, 190D, 247D, 248D, 305D, and 306D have been replaced by A or V at the same time, followed by modification, 4 SpA5 proteins, including SpA5 (KKAA) (SEQ ID NO. 1), SpA5 (RRAA) (SEQ ID NO. 2), SpA5 (KKVV) (SEQ ID NO. 3), and SpA5 (RRVV) (SEQ ID NO. 4), have been obtained in the present invention. In these 4 proteins, amino acids at position 6-296 belong to SpA (252), and the first 5 amino acids (GPLGS, SEQ ID NO. 8) come from the modified amino acids of the expression vector, the encoding sequence of which is preferably gggcccctgggatcc (SEQ ID NO. 16).

Accordingly, in the present invention, there are provided nucleotide sequences encoding any one of the SpA5 proteins of SEQ ID NO. 1-4. Based on known amino acid sequences, appropriate nucleotide sequences encoding the amino acid sequences can be designed by the one skilled in the art as desired, and the designed nucleotide sequences also can be expressed.

In a preferable embodiment, the nucleotides sequences are shown in SEQ ID NO. 9-12.

In another aspect, the present invention provides a vector or a host comprising the nucleotide sequences encoding the SpA5 protein of the invention.

The vector can be any vectors that are suitable for protein expression. In preferable embodiments of the invention, the vector is expression vector pGEX or pET series vector, and more preferably, is expression vector pGEX-6P-2. The map of pGEX series vector is shown in FIG. 1.

pGEX-6p-2 vector preferably employed in the present invention has an advantage that a 26 kDa glutathione-S-transferase (GST) is attached, so that the expressed fusion protein contains a GST-tag which facilitates protein purification. As compared with other fusion vectors, pGEX series vector has the following advantages: mild purification conditions, simple process, and no denaturant added, which allow the proteins to retain their conformation and immunogenicity as much as possible after purification.

The host can be any expression cells known to the one skilled in the art, and preferably, is E. coli XL1-Blue.

In another aspect, there is provided a method for preparing the SpA5 protein, in which the method can be chemical synthesis or gene expression. The method for preparing the SpA5 protein of the invention can be completely understood by the one skilled in the art based on the sequence of the SpA5 protein and the common knowledge in the field.

In another aspect, the present invention provides a fermentation process for the SpA5 gene engineering bacteria, which comprises inoculating a certain amount of seed bacteria into the fermentation media containing glycerol and a certain amount of dissolved oxygen, and inducing for a certain period of time by an inductive agent to express the recombinant protein. Preferably, several factors are involved in the process, including the culture media, the inoculation amount of seed bacteria, the amount of glycerol and dissolved oxygen in the media, the type and the concentration of inductive agent, and the temperature and the duration for induction. More preferably, the culture media is animal origin TB, animal origin M9, plant origin TB, and plant origin M9, and preferably, is animal origin TB. The inoculation amount of seed bacteria is in the range from 5% to 15%, and preferably is 10%. The amount of glycerol is from 5 to 15 mL/L medium, and preferably, is 10 mL/L medium. The amount of dissolved oxygen is 25%-65%, and preferably, is 45%. The inductive agent can be lactose or IPTG and preferably, is IPTG The concentration of the inductive agent is 200 µmol/L-1 mmol/L medium, and preferably, is 200 µmol/L medium. The temperature for induction is 16-37° C., and preferably, is 30° C. The duration for induction is 1-6 h, and preferably, is 5 h.

In a particular embodiment of the fermentation process, the basal medium is animal origin TB medium, in which the amount of glycerol is 10 mL/L; at the beginning of fermentation, the seed bacteria is inoculated in a ratio of 10%; during the course of fermentation, the amount of dissolved oxygen is maintained at around 45% all the time; during induction, the temperature is set at 30° C., the concentration of IPTG is 0.2 mM, and the duration for induction is 5 h.

In another aspect, the present invention further provides a method for purification of the SpA5 protein after host bacteria (gene engineering bacteria) fermentation, which comprises 5 sequential steps, including affinity chromatography, cation-exchange chromatography, ammonium sulfate precipitation, desalinization and anion-exchange chromatography. In the purification process, the affinity chromatography includes digestion by Prescission Protease (PP enzyme) after binding by GST affinity chromatography media, and preferably, by GST sepharose 4B media; the media for cation-exchange chromatography is SP HP, Capto MMC, and Phenyl HP, and preferably is SP HP; the media for desalinization is G 25; and the media for anion-exchange chromatography is Q HP.

The equilibrium buffer used for cation-exchange chromatography is 10-20 mM PB, pH 6.5-7.5, and preferably, 20 mM PB, pH 7.0. The elution buffer used for cation-exchange chromatography is 10-20 mM PB+0.3-1.5 M NaCl, pH 6.5-7.5, and preferably, 20 mM PB+1 M NaCl, pH 7.0. Preferably, the elution procedure is a linear gradient of 0-50% elution buffer for 5 column volumes.

The procedure for ammonium sulfate precipitation includes mixing the sample with 3 M $(NH_4)_2SO_4$ in a ratio of 1:2-1.4:1.6 (V/V) at 4° C., followed by stirring for 10 min and centrifugation at 6000 r/min for 20 min; and preferably, the ratio between the sample and ammonium sulfate is 1.4:1.6.

The equilibrium buffer used for the anion-exchange chromatography is 5-15 mM His+0.01-0.05% poloxamer 188+0.9% NaCl, pH 5-7; and preferably, 10 mM His+0.01% poloxamer 188+0.9% NaCl, pH 6.0.

Preferably, the host (gene engineering bacteria) is disrupted before affinity chromatography, so that the protein can be released.

In another aspect, the present invention provides the use of the SpA5 protein in detection, prevention or treatment of SA infections, or in preparation of a formulation for detection, prevention or treatment of SA infections. Preferably, the formulation is a vaccine.

In another aspect, the present invention further provides an antibody produced by the SpA5 protein immunization, in which the antibody is a polyclonal antibody, that can be used for detection, prevention and treatment of SA infection-associated diseases, or used for preparation of corresponding formulations.

In another aspect, the present invention further provides a composition or a kit comprising the SpA5 protein of the invention. The composition can be a reagent or medicine (such as a vaccine) for prevention, detection or treatment of SA infections. The kit can be any types of kits known in the field, such as detection kit or treatment kit, etc.

In another aspect, the present invention provides a method for detection, prevention or treatment of SA infections, including the use of the SpA5 protein of the invention or the composition comprising the SpA5 protein. Preferably, the subject in need of the method is immunized at the following time points: Day 0, Day 14, and Day 21; Day 0, Day 3, and Day 7; Day 0, Day 3, Day 7, and Day 14.

EXAMPLES

All reagents and strains used in Examples were shown as follows. Any chemical reagent whose manufacturer was not specified in Examples of the present application could be purchased from conventional chemical or biological suppliers in the field.

1. Strains

ATCC international standard strain MRSA-252 of *Staphylococcus aureus*, supplied by ATCC, US;

Host strain *Escherichia coli* XL1-blue, a product of Agilent, US.

2. Plasmid

Plasmid pGEX-6p-2, a product of GE Healthcare, US.

3. Reagents

PrimeSTAR HS DNA-polymerase, DNA molecular weight markers, BamH I and Not I restriction enzyme, protein molecular weight markers, and DNA ligase were purchased from TakaRa (Dalian, China);

Plasmid extraction kit and gel recovery kit were purchased from Omega corporation, US;

Rest reagents, including agar powder and Tween-20, were purchased from domestic companies;

MH medium, supplied by Beijing Aoboxing Biotechnology Co., Ltd. (2.0 g powdered beef, 1.5 g soluble starch, and 17.5 g acid hydrolyzed casein), was added into water to a final volume of 1 L, pH 7.4±0.2;

MH plate: agar was added to MH medium with a final concentration of 1.5 g/100 mL;

PBS: potassium dihydrogen phosphate (KH$_2$PO$_4$) 0.2 g (Domestic reagent of analytical grade), disodium hydrogen phosphate (Na$_2$HPO$_4$.12H$_2$O) 2.9 g (Domestic reagent of analytical grade), sodium chloride (NaCl) 8.0 g (Domestic reagent of analytical grade), and potassium chloride (KCl) 0.2 g, were added into water to a final volume of 1000 mL, pH 7.4;

20 mM PB buffer: potassium dihydrogen phosphate (KH$_2$PO$_4$) 0.2 g, disodium hydrogen phosphate (Na$_2$HPO$_4$.12H$_2$O) 2.9 g, and potassium chloride (KCl) 0.2 g, were added into water to a final volume of 1000 mL, pH 7.0;

Ampicillin, and kanamycin (North China Pharmaceutical Co. Ltd.);

5× Loading buffer (250 mM Tris-HCl (pH 6.8), 10% (W/V) SDS, 0.5% (W/V) bromphenol blue, 50% (V/V) glycerol, and 5% (W/V) β-mercaptoethanol];

Glutathione sepharose 4B (GE Healthcare, US);

Aluminum phosphate adjuvant: GENERAL CHEMICAL corporation (US) (20 mg/ml, concentration of element aluminium: 5.3 mg/ml);

Vaccine diluent: 10 mM histidine (Merck corporation, US, pharmaceutical grade), 0.9% NaCl (Sichuan Kelun Corporation, physiological saline for injection) and 0.01% poloxamer 188 (Merck corporation, US, pharmaceutical grade), pH 6.0, pyrogen-free.

Example 1: Sequence Synthesis

Base sequence and amino acid sequence of SpA (SpA (252), SEQ ID NO. 5) were obtained using MRSA252 genome (GI:49240382) as the templet. Based on the preference of E. coli, rare codon analysis and optimization were performed on website: http://people.mbi.ucla.edu/sumchan/caltor.html for the bases in 5 domains, including E, D, A, B, and C (namely, 37aa-327aa of SEQ ID NO.5, referred as SpA5 (252). Point mutation was performed for 4 amino acids in each domain, and the nucleotide sequences encoding the amino acid sequence of position 6-296 of 4 proteins: SpA5 (KKAA), SpA5 (RRAA), SpA5 (KKVV), and SpA5 (RRVV) were synthesized. The nucleotide sequences were separately linked to expression vector pGEX-6P-2 using BamH I and Not I as two cleavage sites. Host XL-1 Blue was then transformed by the vector (performed by Shanghai Generay Biotech Co., Ltd). The corresponding nucleotide sequences of four SpA5 proteins were shown in SEQ ID NO. 9-12.

In the same manner, the nucleotide sequence of SpA5 (252) was synthesized, linked to the expression vector and transformed into the host.

For the convenience of comparison with the SpA mutant which has been reported, the nucleotide sequence encoding the amino acid sequence of SpA5ref (KKAA) (SEQ ID NO. 6) at position 6-301 was synthesized based on the amino acid sequence of SpA5ref reported (Nontoxigenic protein A vaccine for methicillin-resistant *Staphylococcus aureus* infections in mice. Kim H K, Cheng A G, Kim H Y, Missiakas D M, Schneewind O. J Exp Med. 2010 Aug. 30; 207(9):1863-70). The nucleotide sequence was then linked to the expression vector using the above method, and transformed into the host.

In this example, all synthesized genes were inserted into BamH I site, and subsequently transformed into the host. After expressed by the recombinant engineering bacteria and digested by PP enzyme (GE corporation, US) (5 amino acids (GPLGS) of the vector were retained at N-terminus after digestion), proteins used for the following experiments were obtained, including SpA5 (KKAA), SpA5 (RRAA), SpA5 (RRVV), and SpA5 (KKVV) of the present invention, a protein for comparison SpA5wt (sequence shown in SEQ ID NO. 7, namely, the product obtained by linking the nucleotide sequence of SpA5 (252) to vector pGEX-6P-2, transformed into XL-1Blue and expressed, and finally digested by PP enzyme, which had 5 more amino acids GPLGS (SEQ ID NO.8) at N-terminus than SpA5 (252) and SpA5ref (KKAA).

Example 2: Inductive Expression in *Escherichia coli*, Purification and Characterization of Each Protein 1) Inductive Expression of the Target Proteins (1) 100 µL culture solution of each recombinant engineering bacteria was collected and added into 10 mL LB medium containing ampicillin at a concentration of 100 µg/mL, incubated at 37° C. at 80 rpm overnight. 400 µL culture solution incubated overnight was withdrawn and added to 20 mL LB medium containing ampicillin at a concentration of 100 µg/mL, inbucated at 37° C. for 2-3 h at 220 rpm. After OD$_{600nm}$ increased to 0.8-1.0 in the second activation, IPTG was added to a final concentration of 200 µM. The culture was subsequently placed in a shaker at 30° C. for 3 h, and then at 16° C. overnight for inductive expression.

(2) After inductive expression, the bacteria solution was centrifugated at 10000 rpm for 5 min. The supernatant after centrifugation was discarded, and 1 mL PBS was added and mixed well. Then the bacteria were disrupted by ultrasound (power of 300 W) for 10 min (in a cycle of 6 s on and 9 s off). Subsequently, the mixture was centrifugated at 14000×G for 15 min at 4° C. to separate the supernatant from the precipitate.

2) Treatment of the Supernatant

Binding of the supernatant: 20 µL glutathione-sepharose 4B (GE Healthcare, US) was washed with PBS for 3 times, then the prepared supernatant was added, followed by binding at room temperature for 1 h. The mixture was then centrifugated at 14000 rpm for 3 min at 4° C., then was washed by PBS-0.25% Tween 20 twice and by PBS once.

According to manufacturer's recommended instructions, the bound protein was digested using PP enzyme (Prescission protease, GE Healthcare, US) and eluted. The PP enzyme used had a GST-tag, which facilitated its removal. After digestion, the supernatant was collected after centrifugation. 16 µL supernatant was added to 4 µL 5× loading buffer, and boiled for 5 min. The solution was then centrifugated at 14000 rpm for 3 min.

3) 10% SDS-PAGE

Figure 2:
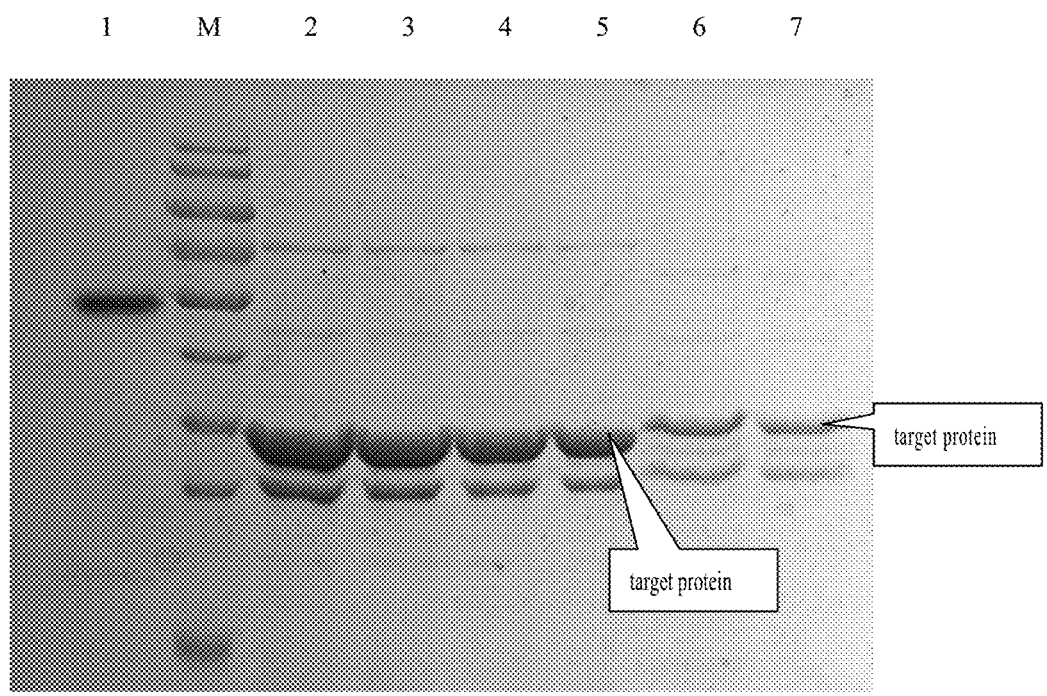
FIG. 2 shows 10% SDS-PAGE analysis of the target proteins inductively expressed in Example 2; Lane 1: SpA (55 KD); M: middle range protein molecular weight markers (170, 130, 100, 70, 55, 40, 35, 25, and 15) KD; Lane 2: SpA5wt (33 KD); Lane 3: SpA5ref (KKAA, 33 KD); Lane 4: SpA5 (KKAA, 33 KD); Lane 5: SpA5 (KKVV, 33 KD); Lane 6: (RRAA, 33 KD); and Lane 7: SpA5 (RRVV, 33 KD).

The electrophoretogram was shown in FIG. 2. Lane 1 illustrated SpA (252) (1.5 µg) purchased from Invitrogen Corporation (US) (REC PROTEIN A10-1100). As shown in FIG. 2, the protein was purified.

Example 3: Fermentation of the Engineering Bacteria

1. Determination of the Conditions for Fermentation

1) Effect of the Medium on the Growth of Engineering Bacteria and the Expression of Target Protein 4 types of culture media were tested by shaking culture using the method as described in Example 2:

Modified TB medium of plant origin (potassium dihydrogen phosphate 2.3 g, disodium hydrogen phosphate dodecahydrate 13 g, glycerol 5 mL, yeast extract 24 g, soybean peptone 12 g, and magnesium sulfate 1 g, adding water to a final volume of 1 L);

Modified TB medium of animal origin (potassium dihydrogen phosphate 2.3 g, disodium hydrogen phosphate dodecahydrate 13 g, glycerol 5 mL, yeast extract 24 g, animal origin tryptone 12 g, and magnesium sulfate 1 g, adding water to a final volume of 1 L);

Plant origin M9-CAA medium (disodium hydrogen phosphate 15.6 g, potassium dihydrogen phosphate 4.3 g, ammonium chloride 1 g, magnesium sulfate 1 g, sodium chloride 0.67 g, glucose 5 g, soybean peptone 3.6 g, plant origin yeast powder 4 g, and acid hydrolyzed casein 6 g, adding water to a final volume of 1 L);

Animal origin M9-CAA medium (disodium hydrogen phosphate 15.6 g, potassium dihydrogen phosphate 4.3 g, ammonium chloride 1 g, magnesium sulfate 1 g, sodium chloride 0.67 g, glucose 5 g, animal tryptone 3.6 g, animal origin yeast powder 4 g, and acid hydrolyzed casein 6 g, adding water to a final volume of 1 L);

SpA5 (KKAA) engineering bacteria were inoculated to an Amp$^+$ (100 µg/mL) LB agar plate, and incubated at 37° C. for 16-20 h. Individual bacterial colonies were picked up and inoculated to 10 mL Amp$^+$LB medium. The suspension was incubated at 37° C. in a shaker shaken at 200 rpm until $OD_{600}$ increased to about 2. The suspension was then inoculated to 4 types of culture media (100 mL each) in a ratio of 1:100, then incubated at 37° C. at 200 rpm for 14 h. Samples were collected at an interval of 2 h to detect $OD_{600}$. The results were shown in FIG. 3.

Figure 3:
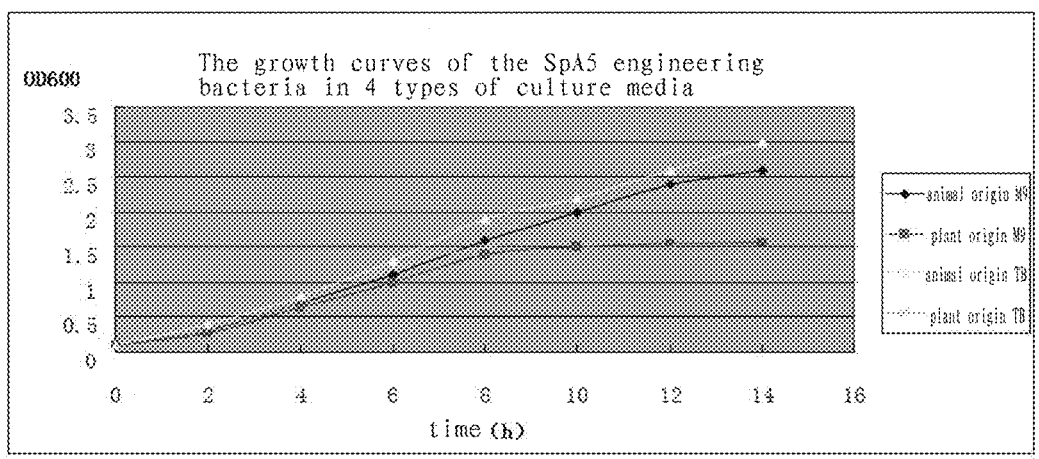
FIG. 3 illustrates the growth curves of the SpA5 engineering bacteria in 4 types of culture media.

As shown in FIG. 3, the growth in the plant origin culture media was poorer than that in the animal origin culture media. In the plant origin culture media, the growth started to slow down at about 8 h, whereas in the animal origin culture media, the growth remained in exponential phase all the time. In another aspect, the growth in the TB medium was better than that in the M9 medium. Thus, the animal origin culture media were selected for the following experiments (animal origin modified TB medium and M9-CAA medium were hereafter referred as TB medium and M9 medium, respectively).

Fresh bacteria solution of the SpA5 engineering bacteria ($OD_{600}$ of about 2) was inoculated to 100 mL TB or M9 medium in a ratio of 1:100 respectively. The culture was then incubated at 37° C. at 200 rpm until $OD_{600}$ increased to about 0.8. Subsequently, 1 mM IPTG was added, and the expression was induced at 25° C. for 12 h. 100 mL bacteria solution was then centrifugated, the supernatant was discarded and the precipitate was weighed: 2.4 g for TB medium and 1.5 g for M9 medium. To the precipitate, PBS was added in a ratio of 1 g:10 mL, then the bacteria were disrupted by ultrasound (power of 300 W) for 10 min (in a cycle of 6 s on and 9 s off). Subsequently, the protein was bound to GST 4B (as detailedly described in Example 4). The result was analyzed by 10% SDS-PAGE, and shown in FIG. 4.

Figure 4:
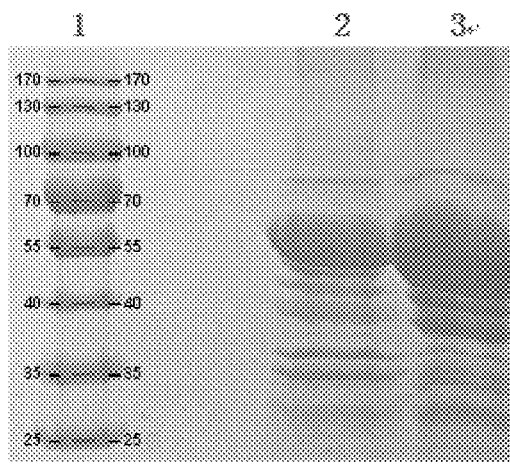
FIG. 4 shows the expression profiles of SpA5 in M9 and TB culture media; Lane 1: protein molecular weight markers; Lane 2: expression profile in M9 culture media; and Lane 3: expression profile in TB culture media.

As shown in FIG. 4, the TB medium was better than the M9 medium in terms of the amount of the expressed target protein. Besides, the TB medium was also more favorable due to the wet weight of bacteria. Thus, the TB medium was selected as the basal medium for the fermentation of the SpA5 engineering bacteria.

2) Effect of IPTG Concentration on the Expression of Target Protein

The effect of different IPTG concentrations on the expression level of target protein was studied. The optimal IPTG concentration was selected after comparison among various final concentrations, including 0.1 mM, 0.2 mM, 0.5 mM, and 1 mM. Fresh bacteria solution of the SpA5 engineering bacteria ($OD_{600}$ of about 2) was inoculated to 4 flasks of TB medium (100 mL each) in a ratio of 1:100, then incubated at 37° C. at 200 rpm until $OD_{600}$ increased to about 0.8. Subsequently, IPTG was added at four different concentrations (1 concentration for 1 flask), and the expression was induced at 25° C. for 12 h. The bacteria solution in each flask was centrifugated separately, and the supernatant was discarded. To the precipitate, PBS was added in a ratio of 1 g:10 mL, then disrupted by ultrasound (power of 300 W) for 10 min (in a cycle of 6 s on and 9 s off). Subsequently, the protein was bound to GST 4B. The result was analyzed by 10% SD S-PAGE, and shown in FIG. 5.

Figure 5:
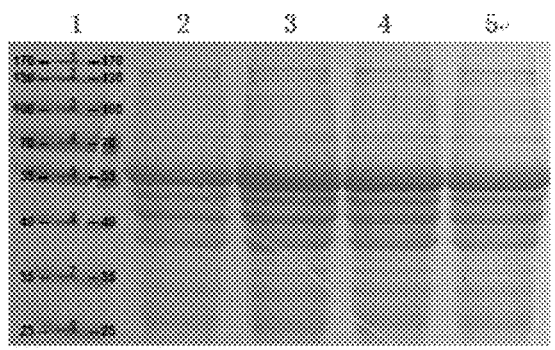
FIG. 5 shows the effect of various IPTG concentrations on the expression of SpA5 protein; Lane 1: protein molecular weight markers; Lane 2: 0.1 mM; Lane 3: 0.2 mM; Lane 4: 0.5 mM; and Lane 5: 1 mM.

As shown in FIG. 5, the expression induced by IPTG at the concentration of 0.2 mM was obviously better than that at 0.1 mM, and was substantially the same as that at 0.5 mM or 1 mM. Thus, 0.2 mM was selected as the final concentration of IPTG for fermentation.

Figure 6:
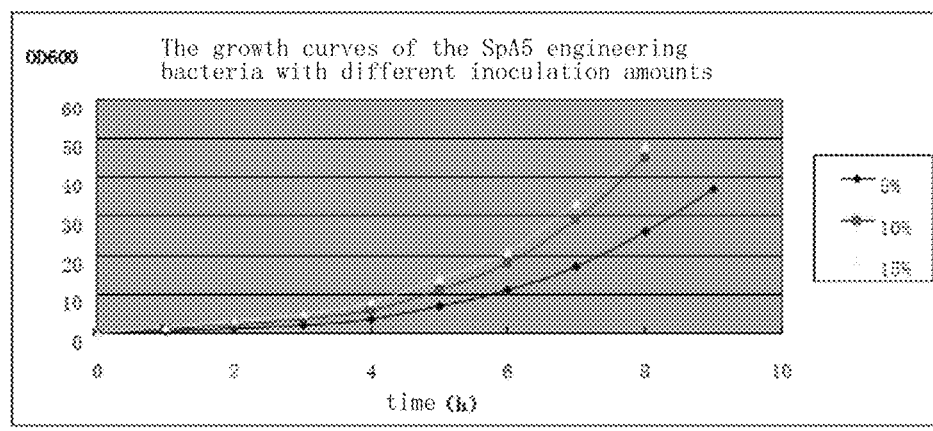
FIG. 6 shows the growth curves of the SpA5 engineering bacteria with different inoculation amounts before induction.

3) Effect of the Inoculation Amount on the Growth of the Engineering Bacteria and the Expression of Target Protein The effect of 3 different inoculation amounts, including 5%, 10%, and 15%, on the fermentation process was studied. The optimal inoculation amount was determined according to the growth curve and the amount of the expressed protein. The seed bacteria ($OD_{600}$ of about 2) was poured into a fermentation tank and begin timing. Samples were collected every one hour for $OD_{600}$ detection until induction is started. The growth curve at the initial stage was plotted for the engineering bacteria (FIG. 6). Based on the plotted curve, the growth rate can be determined. After induction, samples were treated in the same manner as previously described. 10% SDS-PAGE was performed to determine the amount of expressed protein (FIG. 7).

As shown in FIG. 6, the growth rate for the inoculation amount of 5% was the slowest, and its highest $OD_{600}$ was much lower than that obtained for the other 2 inoculation amounts. While for the inoculation amounts of 10% and 15%, no significant difference was observed.

Figure 7:
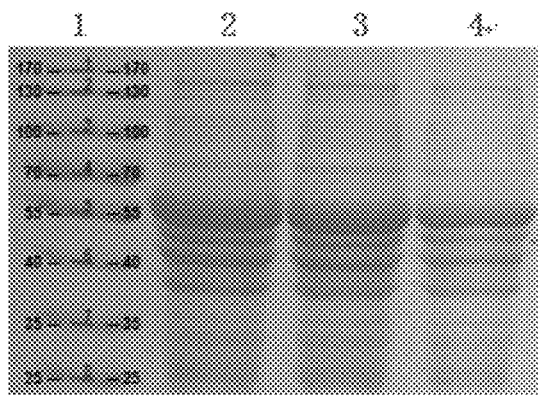
FIG. 7 shows the effect of different inoculation amounts of the SpA5 gene engineering bacteria on the expression profiles; Lane 1: protein molecular weight markers; Lane 2: 5%; Lane 3: 10%; and Lane 4: 15%.

As shown in FIG. 7, the amount of the expressed target protein varied among different inoculation amounts. The largest expression amount was achieved at the inoculation amount of 5%, follow by 10%, with slight difference. The smallest expression amount was seen for the inoculation amount of 15%.

In conclusion, the expression amount for the inoculation amount of 5% was the best, however, the growth rate was slow and the yield of the bacteria was little under this condition. For the inoculation amount of 15%, the expression amount was the smallest, although its growth rate was fast. While for the inoculation amount of 10%, the expression amount was almost the same as that obtained for the inoculation amount of 5%, and the growth rate was also as fast as that for the inoculation amount of 15%. Thus, the inoculation amount of 10% was selected for the fermentation.

Figure 8:
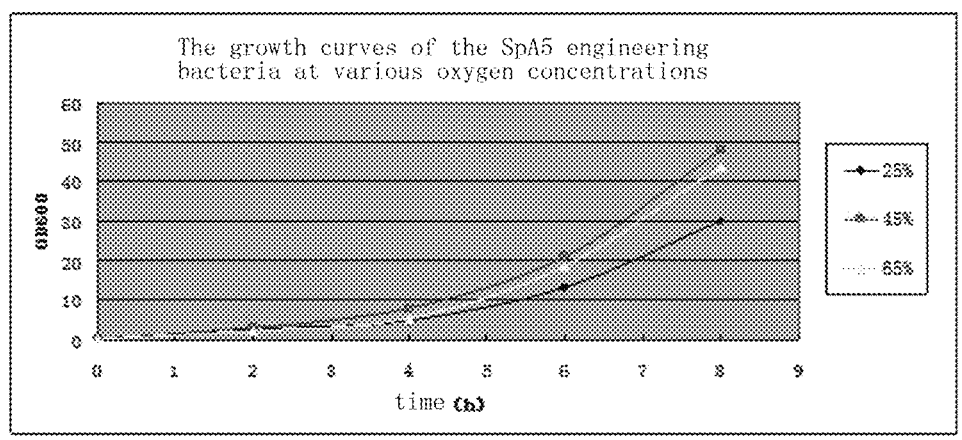
FIG. 8 shows the growth curves of the SpA5 engineering bacteria at various oxygen concentrations.
Figure 9:
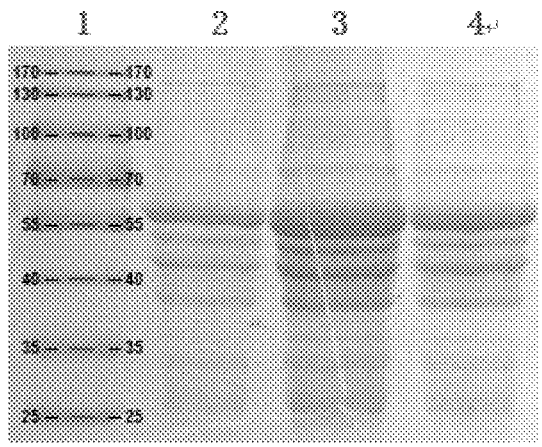
FIG. 9 shows the expression profiles of SpA5 protein at various $pO_2$ concentrations; Lane 1: protein molecular weight markers; Lane 2: 25%; Lane 3: 45%; and Lane 4: 65%.

4) Effect of the Oxygen Concentration on the Growth of the Engineering Bacteria and the Expression of Target Protein The engineering bacteria were a kind of facultative aerobe, so the oxygen concentration was crucial to its growth. Thus, it was important to control the amount of dissolved oxygen during the course of fermentation. In this experiment, the growth of the bacteria (FIG. 8) and the amount of the expressed target protein (FIG. 9) were studied when the dissolved oxygen amount was set at 25%, 45%, or 65%.

It was suggested by the result that the growth of the bacteria was the best at the dissolved oxygen amount of 45%; while for the amount of the expressed protein, the dissolved oxygen amount of 45% was also the best. Thus, the dissolved oxygen amount of 45% was selected for the fermentation process.

5) Determination of the Amount of Glycerol Used

The expression amount of SpA5 varied when induced at different amounts of the bacteria, which were further affected directly by the amount of glycerol in the medium. When the glycerol in the tank was completely consumed, the growth of bacteria will stop, the pH value and the dissolved oxygen amount would increase rapidly in a short period of time, at which time the induction should be started immediately by adding IPTG The amount of glycerol decided the timing of induction directly. The best timing for induction was determined based on the effect of glycerol dosage, including 5 mL/L, 10 mL/L, and 15 mL/L, on the expression of the target protein and the yield of the wet weight of bacteria.

Figure 10:
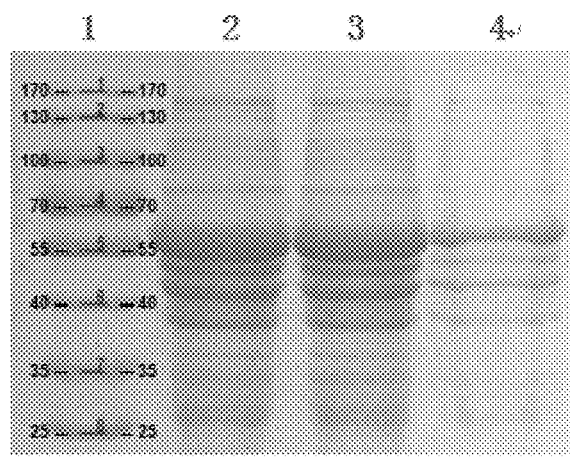
FIG. 10 shows the effect of various glycerol concentrations on the expression of SpA5 protein; Lane 1: protein molecular weight markers; Lane 2: 5 mL/L; Lane 3: 10 mL/L; and Lane 4: 15 mL/L.

FIG. 10 showed the amounts of the expressed target protein at 3 different glycerol dosages. As shown in FIG. 10, the largest expression amount was observed at the glycerol dosage of 5 mL/L, followed by the dosage of 10 mL/L, with slight difference; while the smallest expression amount was observed at the glycerol dosage of 15 mL/L. However, at the glycerol dosage of 5 mL/L, the wet weight of the bacteria was much lower; while for both glycerol dosages of 10 mL/L and 15 mL/L, the wet weights were almost the same. Thus, the glycerol dosage was determined at 10 mL/L.

Figure 11:
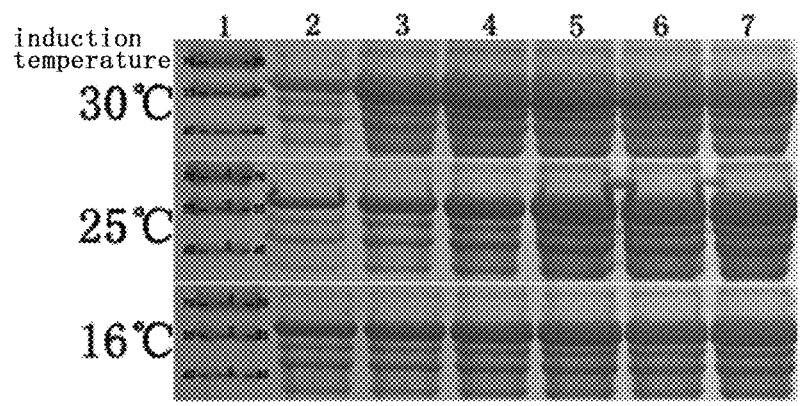
FIG. 11 shows the expression profile of the target protein at different inducing temperatures and for different durations; Lane 1: protein molecular weight markers; Lane 2: duration of 0 h; Lane 3: duration of 2 h; Lane 4: duration of 4 h; Lane 5: duration of 6 h; Lane 6: duration of 8 h; and Lane 7: duration of 10 h.

6) Effect of the Induction Temperature and Duration on the Expression of the Target Protein The expression of the target protein was studied at 3 different induction temperatures, including 30° C., 25° C., and 16° C. Besides, the duration used to achieve the maximal expression amount was also studied. Samples were collected every 2 hours after the induction started, which lasted for 10 h. The collected samples were treated for 10% SDS-PAGE analysis, and the result was shown in FIG. 11.

As shown in the electrophorogram, the highest expression amount was observed at 30° C., with the shortest time used to achieve the highest expression amount. The expression amount varied little during 4 h-6 h. The expression amounts at both 25° C. and 16° C. were worse than that at 30° C., with longer induction time. Thus, the induction temperature and duration were 30° C. and 5 h, respectively.

Based on the above results, the preferable process for fermentation of the SpA5 engineering bacteria of the invention was finally determined:

(1) animal origin TB medium was selected as the basal medium, with the glycerol dosage of 10 mL/L;

(2) the inoculation amount was in a ratio of 10% at the beginning of fermentation;

(3) the dissolved oxygen amount was maintained at around 45% all the time during the course of fermentation;

(4) the induction was carried out at an IPTG concentration of 0.2 mM for 5 h at temperature of 30° C.

2. Scale-Up of the Fermentation Process of Engineering Bacteria

Based on the above optimized conditions, the fermentation process was scaled-up (25 L). The growth curve of the SpA5 engineering bacteria (FIG. 12) and the electrophorogram of the expressed proteins (FIG. 13) were obtained.

Figure 12:
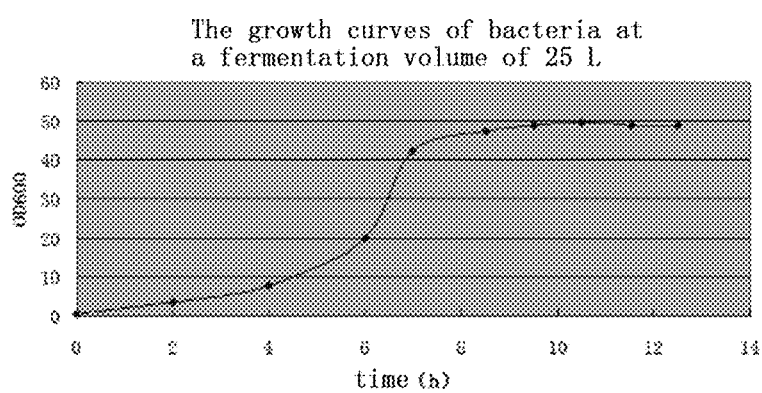
FIG. 12 shows the growth curves of the SpA5 engineering bacteria at a fermentation volume of 25 L.

As shown in FIG. 12, a relatively standard growth curve was observed after scaled-up, with a fast increasing curve at the initial stage and a flat curve at the end stage of induction. The bacterial density ($OD_{600}$) reached 48 at the end of fermentation, with a wet weight of 50 g/L.

Figure 13:
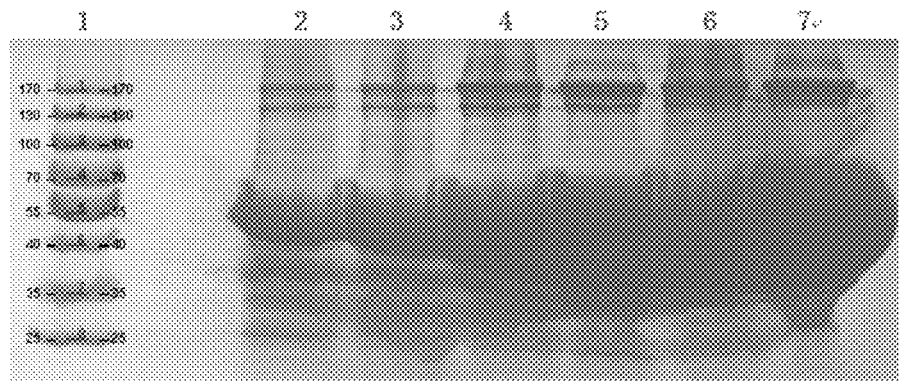
FIG. 13 shows the expression profile of the SpA5 protein by the SpA5 engineering bacteria fermented at the volume of 25 L; Lane 1: protein molecular weight markers; Lane 2: duration of 0 h; Lane 3: duration of 1 h; Lane 4: duration of 2 h; Lane 5: duration of 3 h; Lane 6: duration of 4 h; and Lane 7: duration of 5 h.

As shown in FIG. 13, the expression amount of the target protein increased significantly with extended time, and reached the maximal amount at 5 h.

In conclusion, the scaling-up of the fermentation process was successful for the SpA5 engineering bacteria, as expected. The fermentation process of the present invention was suitable for large-scale industrial production.

The engineering bacteria used in this Example were SpA5 (KKAA). The fermentation process for other engineering bacteria was the same as the engineering bacteria in this Example.

Example 4: Preparation and Purification of the SpA5 Protein

1. Supernatant Prepared from the Disrupted Bacteria

After fermentation, each recombinant engineering bacteria constructed in Example 1 was collected by centrifugation. 200 g-500 g bacteria were mixed well and suspended in 20 mmol/L PB buffer (pH 7.0) in a ratio of 1:10 (w/v), and pre-cooled at 4° C.

High pressure homogenization: after the pipeline of the high pressure homogenizer (AH100B high pressure homogenizer, ATS Industrial System Co. Ltd., Canada) was washed by distilled water, cryogenic recycling system was started to pre-cool the equipment to 1-10° C. for ready use. The pre-cooled bacteria suspension was added to the high pressure homogenizer at a pressure maintained at 730-770 Bar to disrupt the bacteria for 2-5 times. The disrupted bacteria solution was smeared on a slide and stained by crystal violet, then observed by an oil immersion lens. Less than 2 non-disrupted bacteria in each visual field were considered as "complete disruption" (disruption rate >90%).

High speed centrifugation: after disruption, the suspension was loaded into centrifugal barrels equipped for the large high-speed centrifuge (Beckman, US), and centrifugated at 10,000-15,000 g for 15-30 min at 4° C. After centrifugation, the supernatant was collected.

2. Purification Using GST-Sepharose 4B Affinity Chromatography

Figure 14:
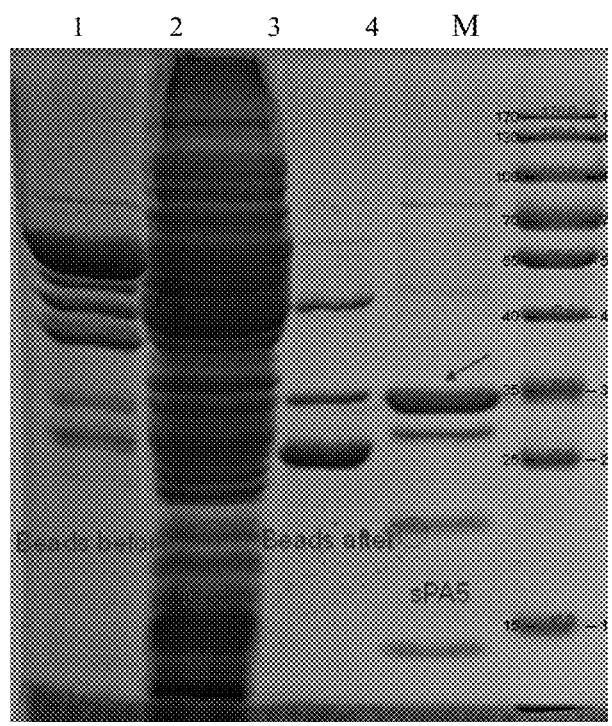
FIG. 14 shows the purification of the target protein by GST-sepharose 4B; Lane M: protein molecular weight markers; Lane 1: GST-SpA5 fusion protein bound with media; Lane 2: flow-through fraction; Lane 3: the media bound by the GST-tag, Prescission Protease (PP) and residue SpA5 after enzyme digestion and elution; and Lane 4: the target protein SpA5 after enzyme digestion and elution.
Figure 15:
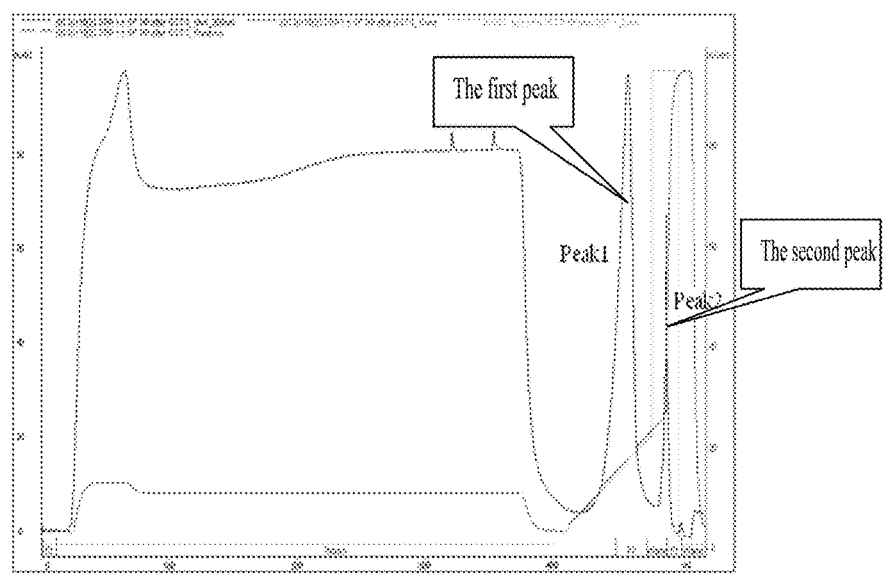
FIG. 15 is the chromatogram illustrating the purification of SpA5 protein on a SP HP column, with two eluting peaks appeared: Peak 1 and Peak 2.
Figure 16:
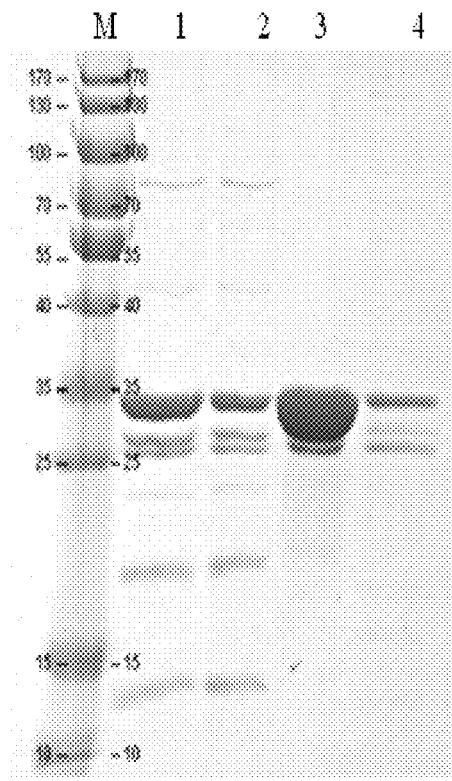
FIG. 16 is the electrophorogram illustrating the purification of SpA5 protein on a SP HP column; Lane M: protein molecular weight markers; Lane 1: sample; Lane 2: flow-through fraction; Lane 3 Peak 1; and Lane 4: Peak 2 (eluted by 1 M NaCl).
Figure 17:
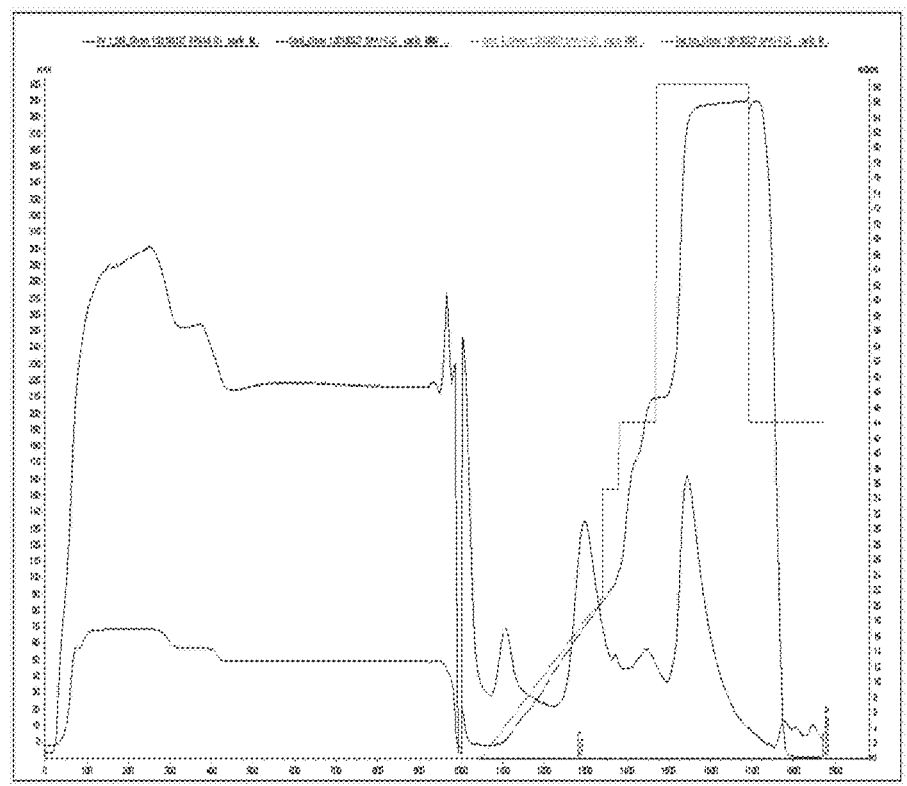
FIG. 17 is the chromatogram illustrating the purification of SpA5 protein on a MMC column.
Figure 18:
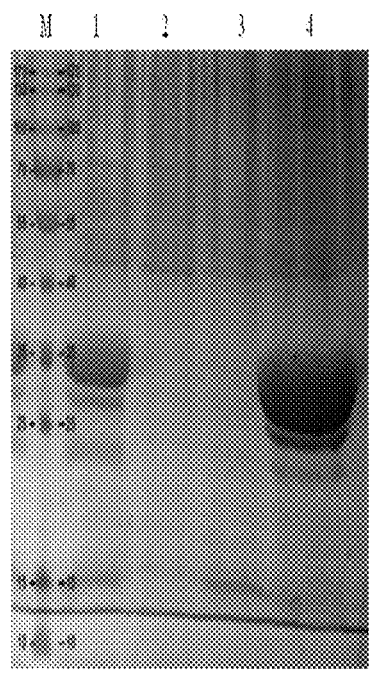
FIG. 18 is an electrophorogram illustrating the purification of SpA5 protein on a MMC column; Lane M: protein molecular weight markers; Lane 1: loading sample; Lane 2: flow-through fraction; Lane 3: fraction eluted by 30% solution B; Lane 4: fraction eluted by 100% solution B.
Figure 19:
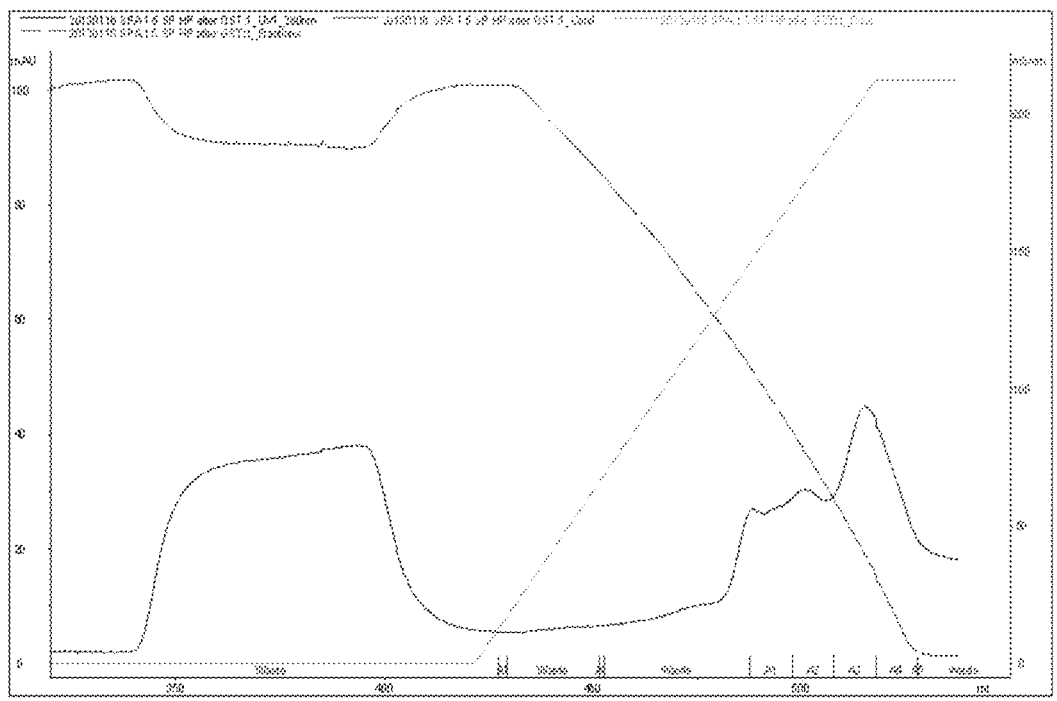
FIG. 19 is a chromatogram illustrating purification of SpA5 protein on a Phenyl HP column.
Figure 20:
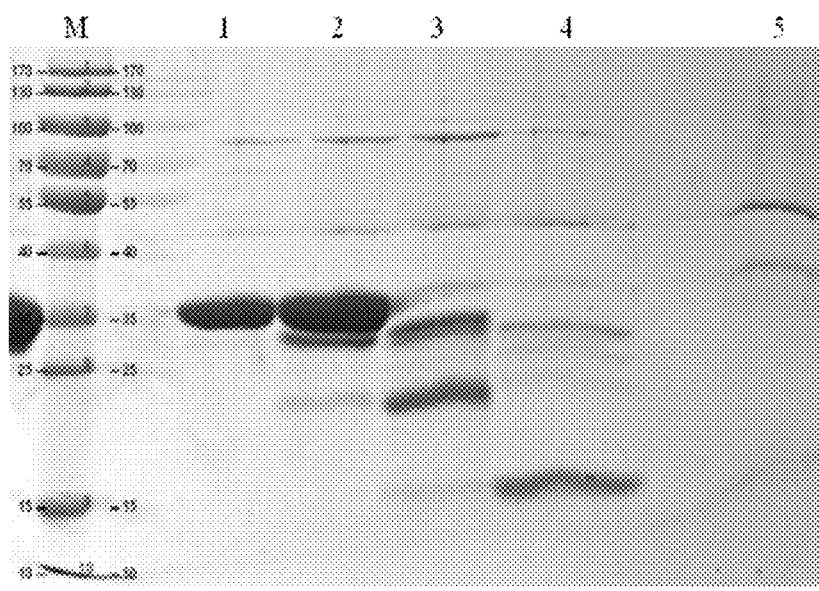
FIG. 20 is an electrophorogram illustrating purification of SpA5 protein on a Phenyl HP column; Lane M: protein molecular weight markers; Lane 1: elution tube A1; Lane 2: elution tube A2; Lane 3 elution tube A3; Lane 4: elution tube A4; and Lane 5: flow-through fraction.

To every 1 L supernatant, 200 mL GST media was added, allowing for binding for more than 4 h at 4-25° C. During this process, vertical rotation or stirring was adopted to promote binding between the target protein and the GST media. The target protein-bound GST media was then washed by PBS for 5 volumes, to remove the protein unbound to the GST-media. Subsequently, to every 100 mL GST media, 20 mL PP enzyme was added. The digestion was carried out at 4-25° C. for more than 2 h. After digestion, the mixture was subjected to suction filtration and the filtrate was collected. The target protein without GST-tag was obtained and subjected to 12% SDS-PAGE analysis. The results were shown in FIG. 14. The result of purification of SpA5 (KKAA) was shown in FIG. 14, which was similar to that for other SpA5 proteins.

3. Purification Using Cation-Exchange Chromatography

The theoretical isoelectric point of each recombinant SpA5 mutant was larger than 8. Accordingly, conventional chromatography media SP HP (strong cation-exchange media), MMC and Phenyl HP media were firstly used for fine purification. Finally, Q HP was used to remove endotoxin after fine purification of SpA5. Fine purification process using chromatography includes:

1) Selection of Chromatography Medias

The purification processes of the SpA5 protein using SP HP, MMC and Phenyl HP medias were compared. The sample used was the SpA5 protein obtained above after crude purification.

Instrument system: AKTA-explorer 100/Avant25 liquid chromatography system (GE)

Medias for chromatography: SP HP, MMC, and Phenyl HP

Column sizes: (1) (Φ) 1.6 cm×(H) 2.5 cm, (2) (Φ) 2.6 cm×(H) 20 cm, and (3) (Φ) 1.6 cm×(H) 2.5 cm;

Packing volume: (1)(3) 5 mL×2, (2) 54 mL;

SP HP buffer: buffer A: 20 mM PB, pH 7.5; buffer B: 20 mM PB+1 M NaCl, pH 7.5;

MMC buffer: buffer A: 20 mM Tris, pH 8.0; buffer B: 20 mM Tris-HCl+1 M NaCl, pH 8.0;

Phenyl HP buffer: buffer A: 20 mM PB+1.5 M $(NH_4)_2SO_4$, pH 6.0; buffer B: 20 mM PB, pH 6.0;

Loading samples: each SpA5 mutant protein after crude purification, adjusted to the pH value identical to that of corresponding buffer A for each media.

SP HP: loading flow rate: 8 mL/min, and elution flow rate: 8 mL/min;

Elution procedure: 0-30% buffer B for 10 column volumes (CV);

MMC: loading flow rate: 12 mL/min, and elution flow rate: 12 mL/min;

Elution procedure: 0-30% buffer B for 7 column volumes (CV);

Phenyl HP: loading flow rate: 8 mL/min, and elution flow rate: 8 mL/min;

Elution procedure: 0-100% buffer B for 10 column volumes (CV);

In each elution procedure, the rest fraction of buffer corresponded to buffer A.

Collection: the target protein samples collected at each elution step were subjected to SDS-PAGE analysis to evaluate the purity.

FIG. 15-20 showed the purification results of SpA5 (KKAA). The results for purifying other SpA5 proteins were consistent with that for SpA5 (KKAA).

As shown in FIG. 15-20, higher purity of the target protein was obtained by SP HP media than MMC and Phenyl HP media, which was more than 90%, demonstrating that favorable purification could be achieved by SP HP media. Based on the above reasons, SP HP media was accordingly selected as media for the first step of purification.

2) Optimization of the Purification Process by Chromatography

Based on determination of using SP HP media in the first purification step, the conditions for purification, mainly including: the conductivity of the loading sample and the elution procedure were optimized in terms of the purity and the yield of SpA5.

Instrument system: AKTA-explorer 100 liquid chromatography system (GE Healthcare)

Media for chromatography: SP HP;

Column size: (Φ) 1.6 cm×(H) 2.5 cm;

Packing volume: 5 mL×2;

Buffer A: 20 mM PB, pH 7.5; buffer B: 20 mM PB+1 M NaCl, pH 7.5;

Loading samples: the SpA5 protein after crude purification, adjusted to the pH 8.0;

Loading flow rate: 8 mL/min, and elution flow rate: 8 mL/min;

Elution procedure: (1) 0-100% B for 10 column volumes (CV); (2) 0-30% B for 10 column volumes (CV); The rest fraction in the eluent was buffer A.

Figure 21:
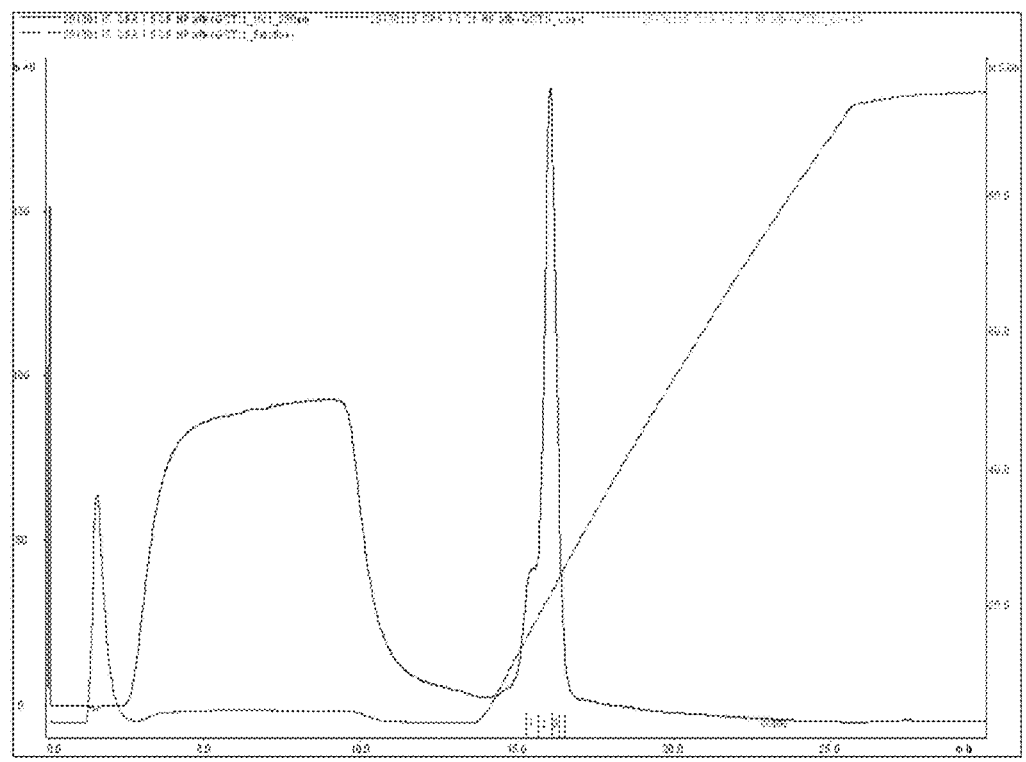
FIG. 21 is a chromatogram illustrating purification of SpA5 protein on a SP HP column (sample conductivity of 4.755 ms/cm).
Figure 22:
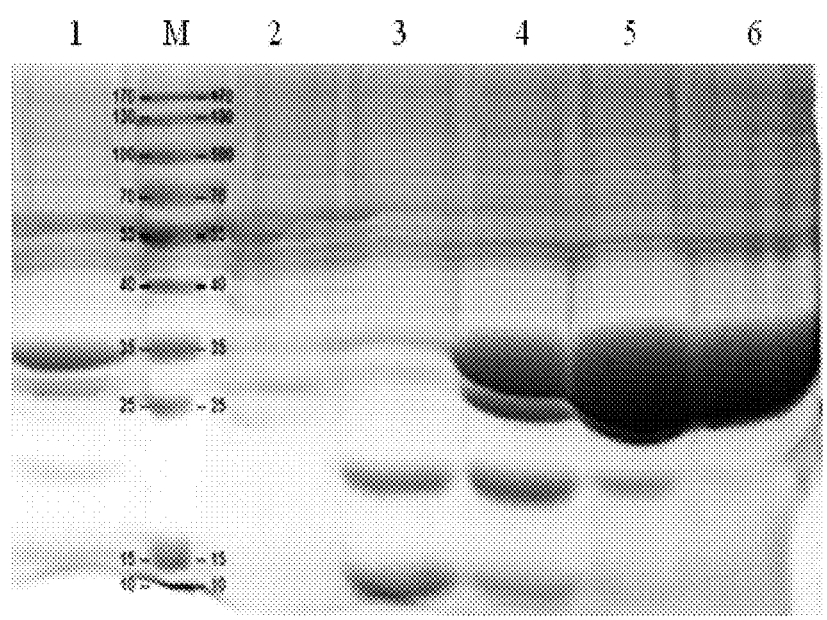
FIG. 22 is an electrophorogram illustrating purification of SpA5 protein on a SP HP column (sample conductivity of 4.755 ms/cm); Lane M: protein molecular weight markers; Lane 1: sample; Lane 2: flow-through fraction; Lane 3: elution tube 1; Lane 4: elution tube 2; Lane 5: elution tube 3; and Lane 6: elution tube 4.
Figure 23:
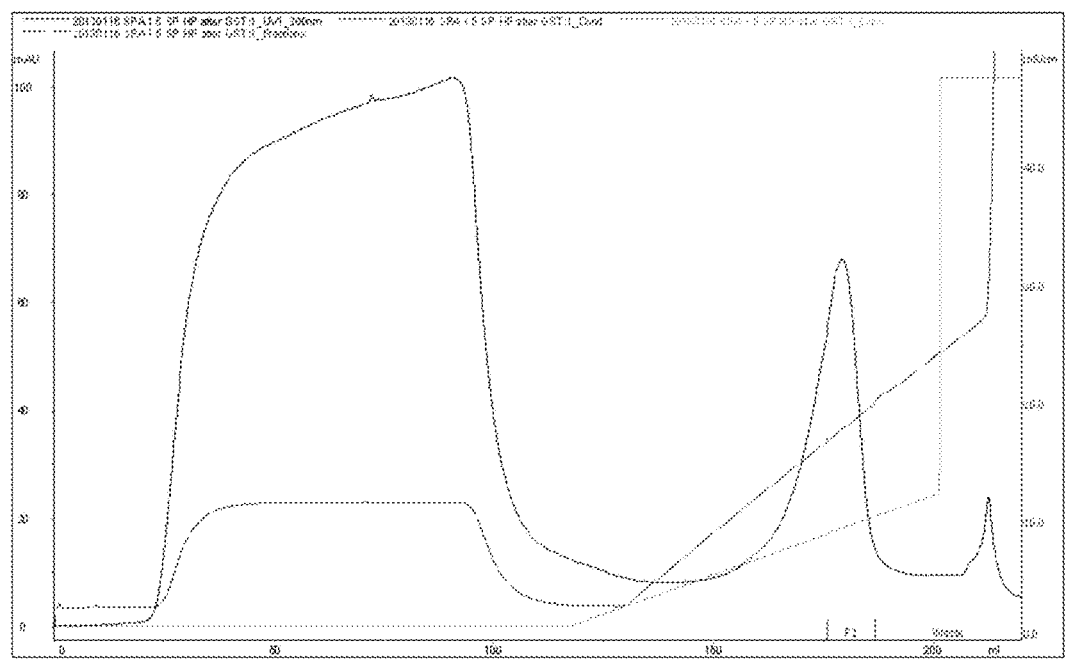
FIG. 23 is a chromatogram illustrating purification of SpA5 protein on a SP HP column (sample conductivity of 11.622 ms/cm).
Figure 24:
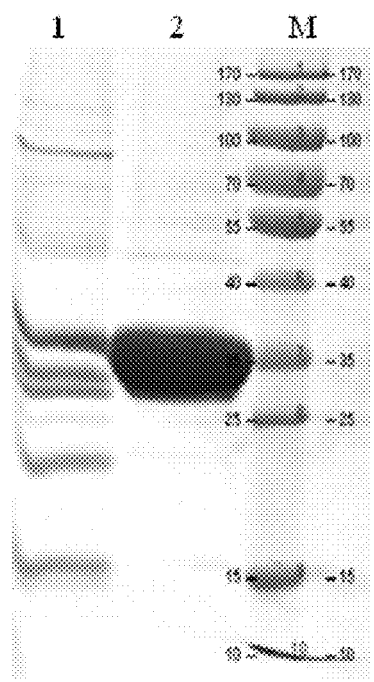
FIG. 24 is an electrophorogram illustrating purification of SpA5 protein on an SP HP column (sample conductivity of 11.622 ms/cm); Lane M: protein molecular weight markers; Lane 1: flow-through fraction; and Lane 2: F2.

As shown in FIG. 21-22, no target protein was observed in the flow-through fraction using the loading sample with low conductivity, and the peak of target protein appeared very early. While as shown in FIG. 23-24, no target protein was obviously seen in the flow-through fraction with increased conductivity of the loading sample. In order to increase the recovery of the target protein, the sample was loaded at low conductivity. Based on the above reasons, the conductivity of the loading sample was about 5 ms/cm, and the elution procedure was 0-50% B, 5 CV.

4. Purification by Ammonium Sulfate Precipitation

After purification by SP HP chromatography, the purity of SpA5 was more than 90%. However, it was still demanded for further purification to remove the band immediately below the target protein as seen in the electrophoretogram. The sample was further purified by ammonium sulfate precipitation to make SpA5 precipitated and leave the impurity protein in the supernatant.

Determination of the Conditions for Ammonium Sulfate Precipitation:

The sample of SpA5 obtained after SP HP purification was mixed with ammonium sulfate in various ratios, stirred, and centrifugated. The supernatant and the precipitate were individually collected, and subjected to SDS-PAGE for purity analysis.

Samples: the SpA5 protein after SP HP purification.

Figure 25:
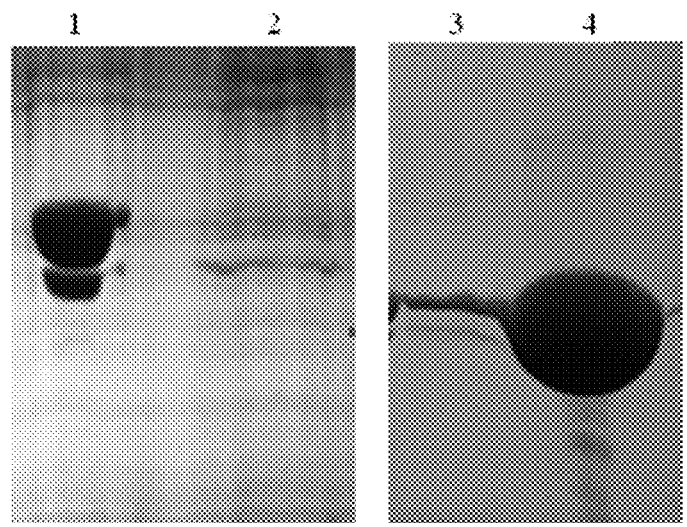
FIG. 25 shows the effect of ammonium sulfate concentration on SpA5 precipitation; Lane 1: the precipitate obtained with 2 M; Lane 2: the supernatant obtained with 2 M; Lane 3: the supernatant obtained with 1.6 M; and Lane 4: the precipitate obtained with 1.6 M.

Ammonium sulfate: 3 M;

Conditions for precipitation: the sample was mixed with 3 M $(NH_4)_2SO_4$ in different ratios, including: 1:2 and 1.4:1.6 (v/v) at 4° C., followed by stirring for 10 min and centrifugation at 6000 r/min for 20 min;

Result analysis: the supernatant and the precipitate after centrifugation were individually collected and subjected to SDS-PAGE to evaluate the removal of impurity protein by ammonium sulfate precipitation at different concentrations (FIG. 25).

FIG. 25 showed the result of SpA5 (KKAA) purification by ammonium sulfate precipitation. The results for the rest SpA5 proteins were consistent with SpA5 (KKAA). As seen from the purity comparison among proteins in FIG. 25, the removal result of impurity protein by mixing the SpA5 (KKAA) sample after SP HP purification with 3 M $(NH_4)_2SO_4$ in a ratio of 1.4:1.6 at 4° C. is the best, the purity of SpA5 was more than 95%. Accordingly, the preferable precipitation conditions of the invention included: mixing the SpA5 sample with 3 M $(NH_4)_2SO_4$ in a ratio of 1.4:1.6 at 4° C., followed by centrifugation and collection of the precipitate of the SpA5 protein.

5. Desalinization

G25 desalinization column was equilibrated by the vaccine diluent, then the sample obtained from the previous purification step was loaded to the column to replace the buffer.

Specifically, the sample obtained from the previous purification step was dissolved in the histidine buffer (histidine (Merck, US, Pharmacuetical grade) 10 mmol/L, poloxamer 188 (Merck, US, Pharmacuetical grade), 0.01% w/v, NaCl 9 g/L (Southwest Pharmacuetical Co., Ltd.), and loaded to a pre-equilibrated XK 50-60 column (GE Healthcare, US) (600 mL Sephadex G 25) connected to the chromatography system (AKTA Explorer 100, GE Healthcare, US). The column was eluted at a flow rate of 20 mL/min for desalinization (removal of $(NH_4)_2SO_4$ and PB).

6. Removal of Endotoxins

Instrument system: AKTA-explorer 100 liquid chromatography system (GE Healthcare);

Media for chromatography: Q HP;
Column sizes: (Φ) 2.6 cm×(H) 20 cm;
Packing volume: 50 mL;
Buffers: buffer A: 10 mM His+0.01% poloxamer 188+ 0.9% NaCl, pH 6.0, free of endotoxin (the vaccine diluent); buffer B: 1 M NaOH;

Loading samples: the sample obtained from the desalinization step, adjusted to the pH value identical to buffer A for ready use.

The column was washed by buffer B (1 mol/L NaOH) in situ for 5 column volumes, and stood for 0.5 h. The system was then equilibrated by the vaccine diluent to pH 6.0, followed by loading the sample to the column. Flow rate: 8 mL/min. The flow-through peak (i.e., the target protein) was collected.

Figure 26:
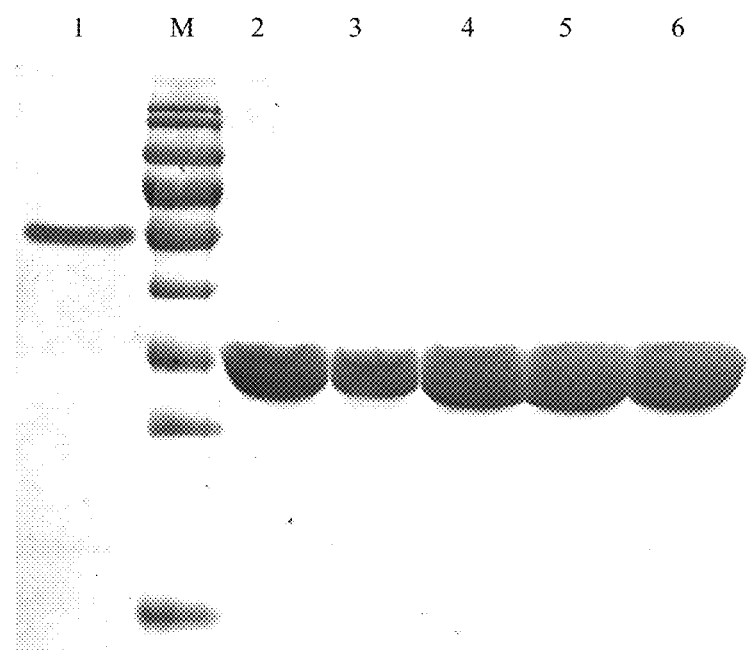
FIG. 26 shows fine purification of SpA mutants; Lane M: protein molecular weight markers; Lane 1: SpA; Lane 2: SpA5ref (KKAA); Lane 3: SpA5 (KKAA); Lane 4: SpA5 (KKVV); Lane 5: SpA5 (RRAA); and Lane 6: SpA5 (RRVV).
Figure 27:
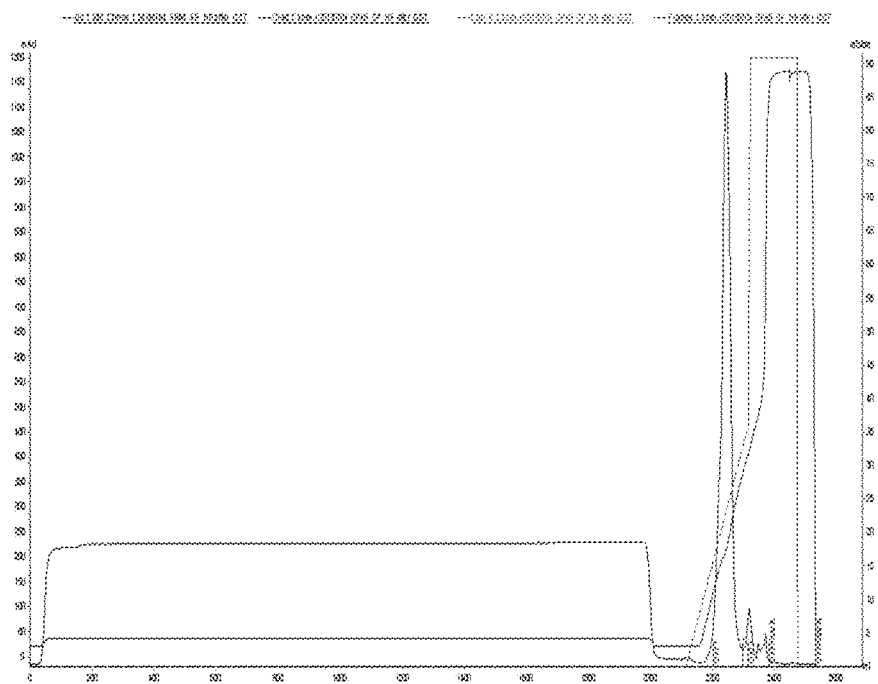
FIG. 27 is a chromatogram illustrating purification of SpA5 protein on a SP HP column (batch I) at a scaled-up level.
Figure 28:
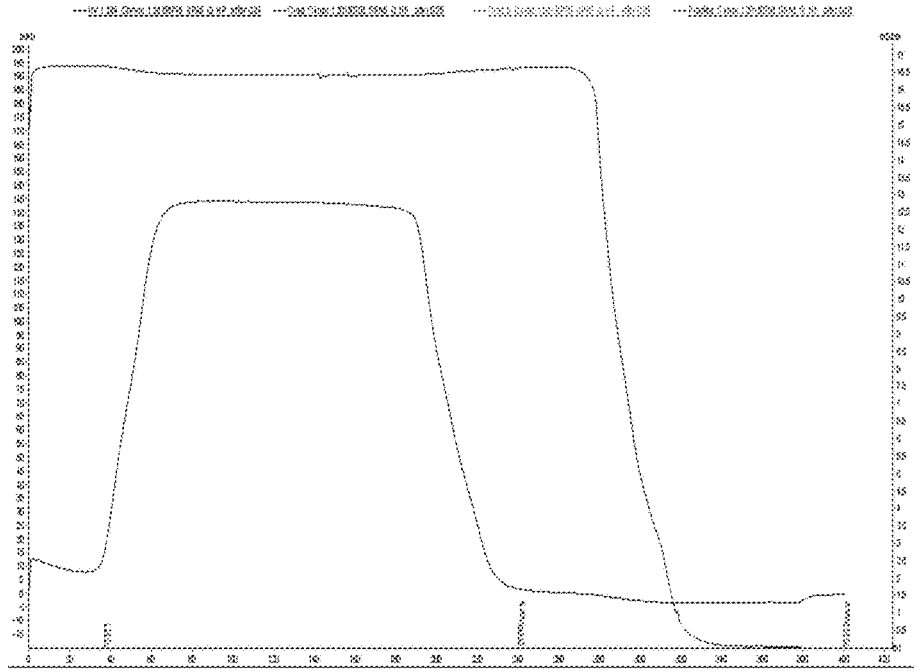
FIG. 28 is a chromatogram illustrating purification of SpA5 protein on a Q HP column (batch I) at a scaled-up level.
Figure 29:
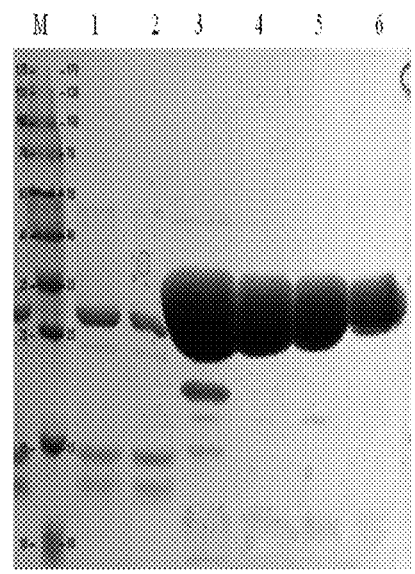
FIG. 29 is an electrophorogram illustrating purification of SpA5 protein at a scaled-up level (batch I); Lane M: protein molecular weight markers; Lane 1: sample before purification; Lane 2: flow-through fraction; Lane 3: eluent from a SP HP column; Lane 4: sample of re-dissolved precipitate obtained with $(NH_4)_2SO_4$; Lane 5: eluent from a G25 column; and Lane 6: flow-through fraction from a Q HP column.
Figure 30:
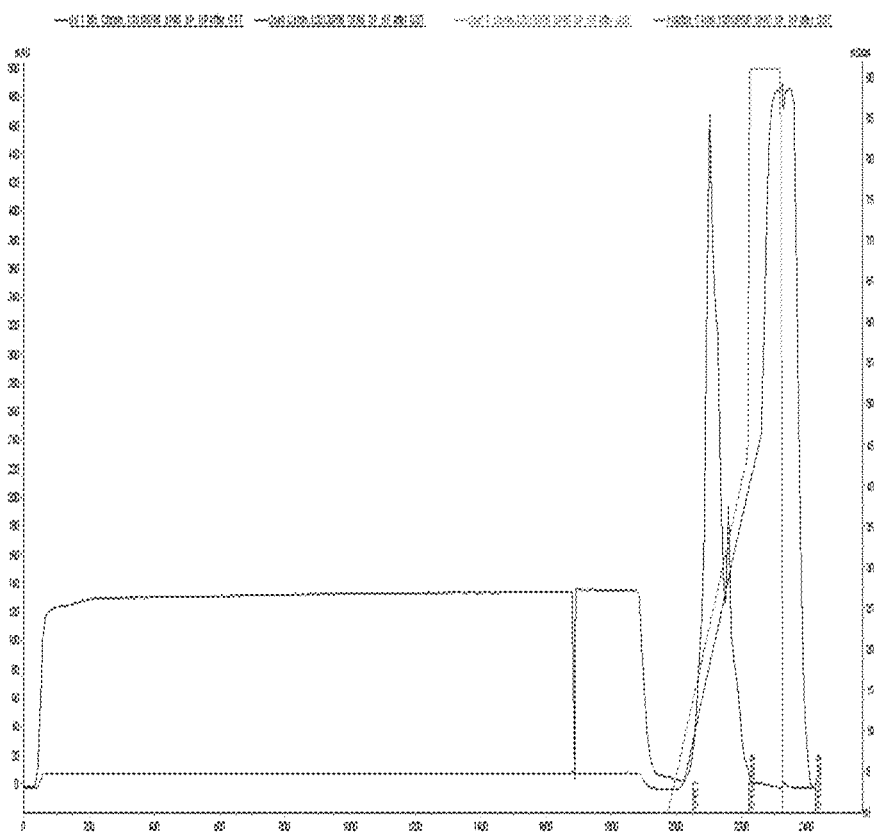
FIG. 30 is a chromatogram illustrating purification of SpA5 protein on a SP HP column (batch II) at a scaled-up level.
Figure 31:
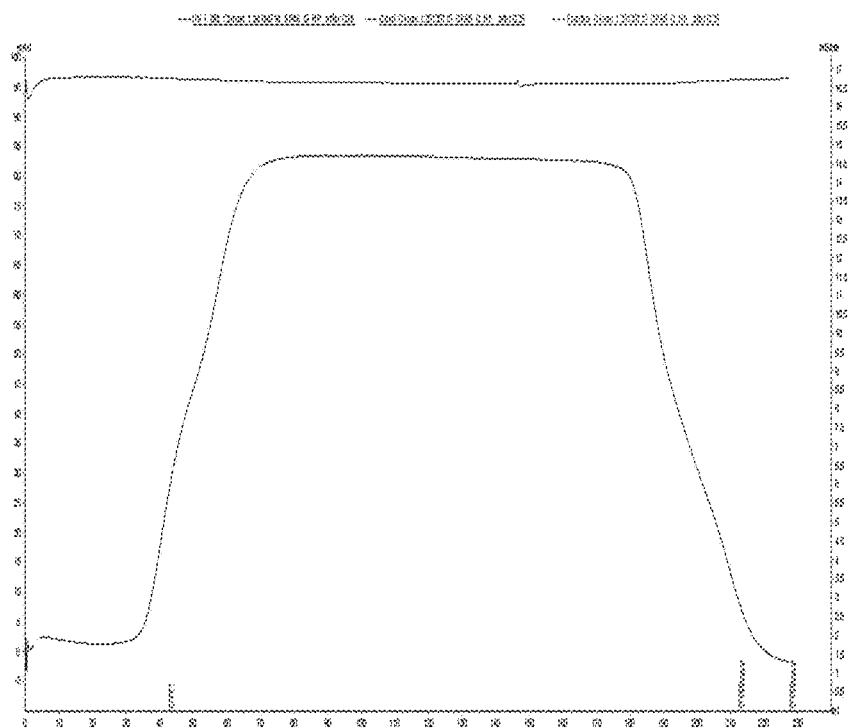
FIG. 31 is a chromatogram illustrating purification of SpA5 protein on a Q HP column (batch II) at a scaled-up level.
Figure 32:
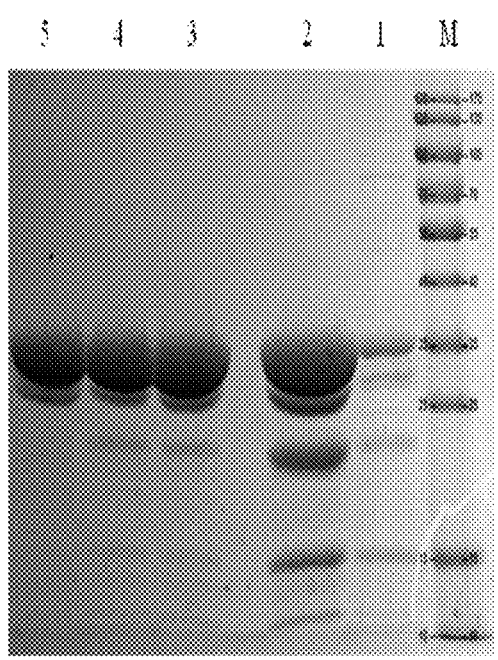
FIG. 32 is an electrophorogram illustrating purification of SpA5 protein at a scaled-up level (batch II); Lane M: protein molecular weight markers; Lane 1: sample before purification; Lane 2: eluent from a SP HP column; Lane 3: sample of re-dissolved precipitate obtained with $(NH_4)_2SO_4$; Lane 4: eluent from a G25 column; and Lane 6: flow-through fraction from a Q HP column.
Figure 33:
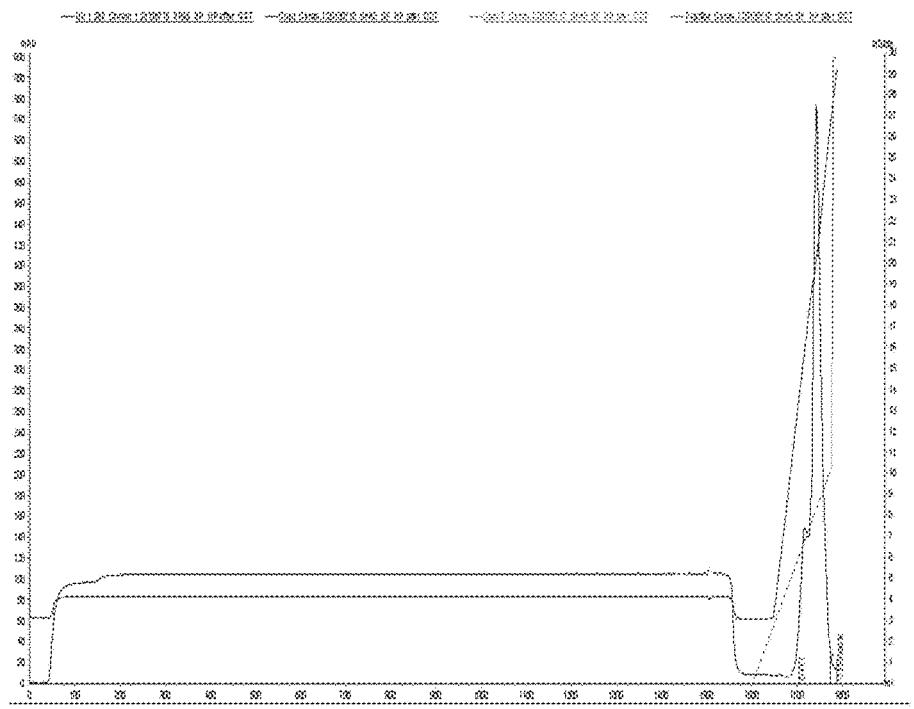
FIG. 33 is a chromatogram illustrating purification of SpA5 protein on a SP HP column (batch III) at a scaled-up level.
Figure 34:
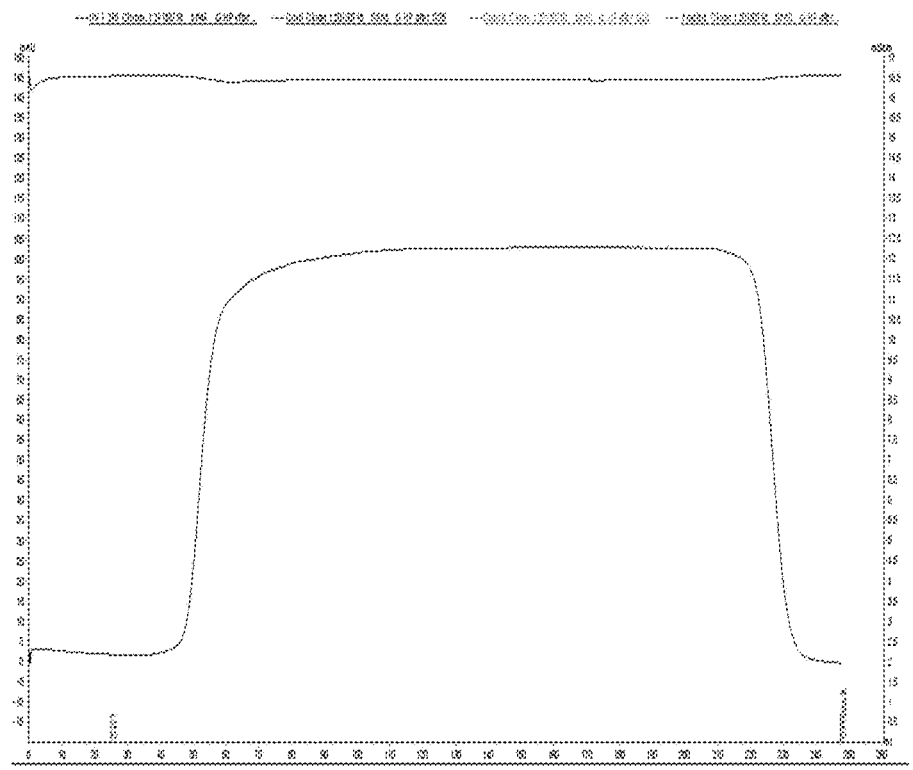
FIG. 34 is a chromatogram illustrating purification of SpA5 protein on a Q HP column (batch III) at a scaled-up level.
Figure 35:
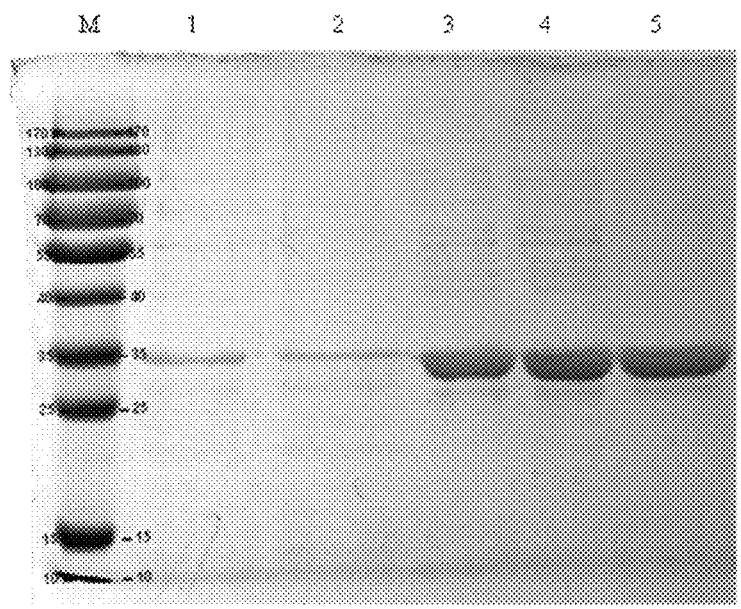
FIG. 35 is an electrophorogram illustrating purification of SpA5 protein at a scaled-up level (batch III); Lane M: protein molecular weight markers; Lane 1: sample before purification; Lane 2: flow-through fraction; Lane 3; eluent from a SP HP column; Lane 4: eluent from a G25 column; and Lane 5: flow-through fraction from a Q HP column.

The sample of the flow-through peak was subjected to 10% SDS-PAGE, as shown in FIG. 26.

7. Scaling-Up

The process was scaled-up based on the conditions determined above: the chromatography column of SP HP was scaled-up to (Φ) 2.6 cm×(H) 20 cm, with a packing volume CV=50 mL; the chromatography column of Q HP was scaled-up to (Φ) 2.6 cm×(H) 20 cm, with a packing volume CV=50 mL. The experiment was repeated for 3 times. The purity and the yield of SpA5 after purification were analyzed by SDS-PAGE. The stability and the repeatability of the process were evaluated after scaling-up.

As shown in FIG. 27-35, there was no obvious change between the scaled-up process and the small-scale test for the purification of the SpA5 protein by SP HP chromatography. After purification, the purity of SpA5 was more than 95%.

8. Purity Detection by HPLC

HPLC instrument: Agilent 1260 (Agilent, US), analytical column: ZorBax SB-300-C3 4.6×150 mm 3.5 micron (Agilent, US).

Mobile phases: A: 0.1% trifluoroacetic acid (Tedia, US), water (18.2 MΩ); B: 0.1% trifluoroacetic acid (Tedia, US), acetonitrile (Tedia, US).

Column temperature: 60° C., flow rate: 0.5 mL/min, and injection volume: 10 μL.

Detection method: 0-30 min: 90% A, 10% B; 30-35 min: 100% B; 35-40 min: 90% A, 10% B; 40-45 min: 90% A, 10% B.

Figure 36:
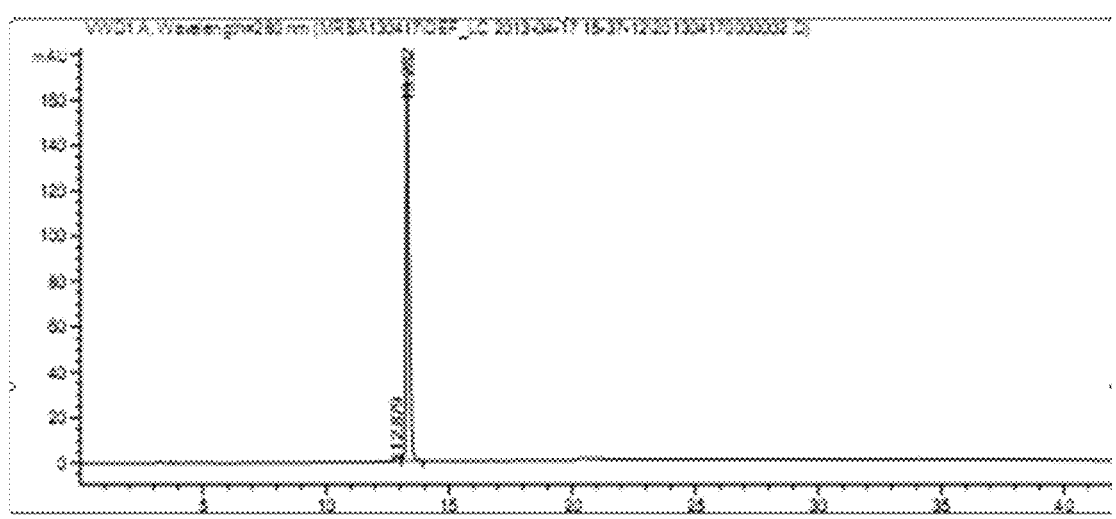
FIG. 36 shows the detection of SpA5 (KKAA) mutant by HPLC; the retention time of the main peak: 13.282 min; and the main peak area ratio: 98.2%.

The results were shown in FIG. 36 and listed in Table 1.

As shown in FIG. 36 and Table 1, there was almost no impurity peak in the sample of the purified SpA5 (KKAA) mutant. The retention time of the main peak was 13.282 min, with the peak area ratio of 98.2%. Similar results were observed for the rest of mutants.

TABLE 1

Detection of peak by HPLC

| Peak No. | Retention time (min) | Type | Peak width (min) | Peak area (mAU * s) | Ratio of Peak area |
|---|---|---|---|---|---|
| 1 | 11.158 |  | 0.0000 | 0.00000 | 0.0000 |
| 2 | 12.879 | BV | 0.1387 | 26.23703 | 1.7774 |
| 3 | 13.282 | VB | 0.1186 | 1449.93225 | 98.2226 |
| 4 | 32.252 |  | 0.0000 | 0.00000 | 0.0000 |

9. N- and C-Terminal Sequencing, Molecular Weight Determination and Amino Acid Composition Analysis of the Proteins The resultant SpA5 mutants (including four SpA5 mutants of the invention and SpA5ref (KKAA) were sequenced by Shanghai Applied Protein Technology Co. Ltd. The results indicated that the sequences of the mutants were consistent with the designed sequences.

Example 5: Determination of the Endotoxin Content

1. The samples of Example 4 were diluted using water for bacterial endotoxin detection (Zhanjiang Bokang Marine Biological Co., Ltd.) to a concentration of 50 μg/mL, and then used for detection. The samples were diluted to 2 folds of the sensitivity (0.25 EU/mL) of the endotoxin detection kit (Zhanjiang Bokang Marine Biological Co., Ltd.).

2. According to Appendix XII E "Method for detection of bacterial endotoxin" in "Pharmacopoeia of the People's Republic of China", 2010, the 3$^{rd}$ edition and the instructions of the kit, positive control solution of endotoxin standards, working solution of test sample, positive control solution of test sample, and detection solution of test sample were prepared.

3. Preparation of Limulus Amoebocyte Lysate (LAL): based on the amount of the test samples and the control samples, LAL was prepared. Before opening the LAL vial, the bottleneck was sterilized by alcohol swab and air-dried. To each vial, 0.1 mL detection water was added, and gently mixed for further use.

4. Sample addition: to the prepared LAL, 0.1 mL of each of the following solutions were added: detection solution of test sample, positive control solution of test sample, positive control solution of endotoxin standards and detection water. The mixture was gently mixed, sealed by parafilm, and then placed in a water bath at 37° C. for 60±2 min, during this period, the samples should not be moved. Detection water was used as a negative control.

5. Detection: LAL was taken out from the water bath carefully, and gently inverted vertically to observe the bottom. Intact gel that did not slide along the wall of test tube was considered as positive, and designated as (+); while broken gel that slided along the wall of test tube was considered as negative, and designated as (−).

6. Results: all mutant protein solutions were negative, with endotoxin content less than 5 EU/ml.

Example 6: Binding Between Each Coated Protein and Human IgG

Figure 37:
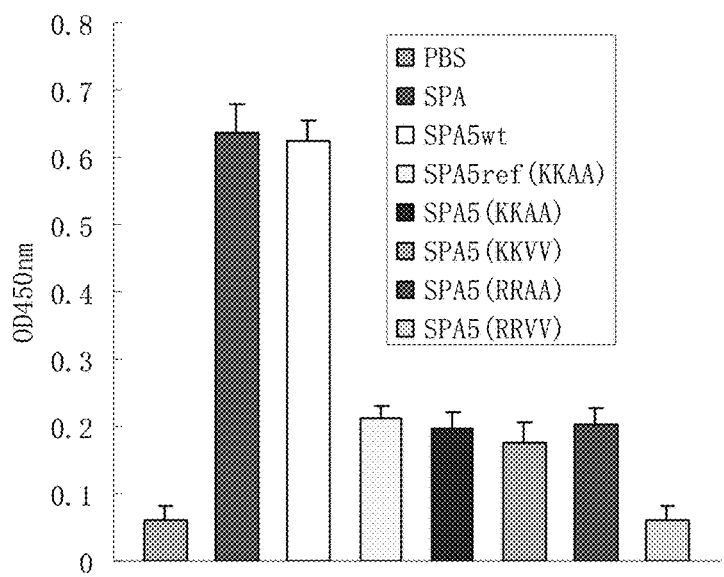
FIG. 37 shows the binding capacities of SpA and each SpA5 protein to human IgG by ELISA (mean value±stdev, n=12).

The resultant proteins were each diluted by 0.1 mol/L carbonate buffer (pH 9.5) to a concentration of 500 ng/ml. A 96-well ELISA plate was then coated by 100 μL of the diluted protein solution at 4° C. over night. The plate was washed by the washing solution (Tris 2.42 g, Tween 20 0.5 mL, adjusted to pH=7.4 by concentrated HCl, adding ddH$_2$O to a total volume of 1000 mL) for 4 times. To each well, 200 μL blocking solution (5% (w/v) skimmed milk powder dissolved in 100 mmol/L TTBS (Tris (pH 7.5), Tween 20 0.1% (v/v), and NaCl 0.9% (w/v)) was added for blocking at 37° C. for 2 h. The liquid was discarded, and the plate was washed for 4 times by the washing solution. 100 μL human IgG-HRP (Beijing Zhongshan Golden Bridge Biotechnology Co. Ltd.) (1:5000) was added and incubated at 37° C. for 60 min. The liquid was discarded, and the plate was washed for 4 times by the washing solution. 100 μL/well freshly prepared developing solution containing OPD was added, and developed at room temperature in dark for 15 min. 50 μL 12.5% H$_2$SO$_4$ was added to stop the reaction. OD$_{450nm}$ was then detected. Higher OD value indicated stronger binding to human IgG, further suggesting that it was not suitable as an antigen candidate. Results were shown in FIG. 37 and listed in Table 2, in which PBS was used as a negative control.

TABLE 2

Binding capacities of SpA and each mutant protein thereof to human IgG detected by ELISA

| Groups | PBS | SpA | SpA5 wt | SpA5Ref (KKAA) | SpA5 (KKAA) | SpA5 (KKVV) | SpA5 (RRAA) | SpA5 (RRVV) |
|---|---|---|---|---|---|---|---|---|
| OD$_{450\ nm}$ | 0.05 | 0.629 | 0.615 | 0.252 | 0.166 | 0.217 | 0.189 | 0.027 |
| | 0.068 | 0.611 | 0.618 | 0.187 | 0.231 | 0.173 | 0.179 | 0.1 |
| | 0.047 | 0.65 | 0.618 | 0.242 | 0.209 | 0.167 | 0.2 | 0.07 |
| | 0.08 | 0.665 | 0.579 | 0.186 | 0.21 | 0.128 | 0.19 | 0.036 |
| | 0.065 | 0.675 | 0.622 | 0.198 | 0.197 | 0.177 | 0.226 | 0.061 |
| | 0.074 | 0.623 | 0.668 | 0.231 | 0.189 | 0.19 | 0.226 | 0.062 |
| | 0.05 | 0.639 | 0.689 | 0.212 | 0.201 | 0.173 | 0.207 | 0.055 |
| | 0.049 | 0.56 | 0.629 | 0.194 | 0.16 | 0.184 | 0.174 | 0.084 |
| | 0.019 | 0.554 | 0.621 | 0.19 | 0.203 | 0.118 | 0.196 | 0.069 |
| | 0.092 | 0.663 | 0.587 | 0.228 | 0.206 | 0.164 | 0.264 | 0.033 |
| | 0.051 | 0.688 | 0.647 | 0.199 | 0.169 | 0.235 | 0.185 | 0.06 |
| | 0.092 | 0.661 | 0.61 | 0.216 | 0.231 | 0.174 | 0.205 | 0.088 |
| Mean value | 0.061 | 0.635 | 0.625 | 0.211 | 0.198 | 0.175 | 0.203 | 0.062 |
| Standard deviation | 0.021 | 0.043 | 0.031 | 0.023 | 0.023 | 0.032 | 0.025 | 0.022 |
| Paired t-test (compared with SpA5ref (KKAA) P | | | | | 0.208 | <0.01 | 0.335 | <0.01 |

As indicated by the results, binding capacities to human IgG of each SpA5 protein of the invention decreased significantly as compared to the wild-type SpA5wt and SpA (252), P<0.01; while SpA5 (RRVV) had already lost its binding capacity to human IgG.

Example 7: Binding Between SpA and Human IgG Blocked by Rabbit Anti-Recombinant Mutant Antibody F(ab)$_2$ Fragments Based on the results of Example 6, SpA5wt had the same binding capacity to human IgG as the intact SpA protein, so that both proteins were not subjected to this experiment.

1) Immunization of Rabbit 1 mL complete Freund's adjuvant (Sigma, US) was added to each of 2 mg SpA5ref (KKAA), SpA5 (KKAA), SpA5 (KKVV), SpA5 (RRAA) and SpA5 (RRVV) (2 mg/ml), and the mixture was fully emulsified. 25 New Zealand big ear rabbits (2.0-2.5 kg, Laboratory Animal Centre, Third Military Medical University) were divided into 5 groups, with 5 rabbits in each group. The rabbits were subcutaneously immunized at multi-site by 2 mL emulsified protein (protein content of 2 mg) on Day 0, Day 14 and Day 28. Serum was collected on the Day 7 after the last immunization.

2) Purification of the Antibodies

After ammonium sulfate precipitation, the rabbit serum was diluted by PBS, and subsequently loaded to a pre-packed Protein G column (GE Healthcare, US) pre-equilibrated by PBS. The column was then washed by PBS, and eluted by a buffer containing 1 mol/L glycine and 0.5 mol/L NaCl (pH 2.5). The eluent was immediately neutralized by 1 mol/L Tris-HCl buffer (pH 8.5) and dialyzed against PBS. The antibody concentration was determined as 3 mg/ml by Lowry method. The antibody was an SpA5 specific antibody, as confirmed by western blot.

3) Preparation of Antibody F(ab)$_2$ Fragments

Figure 38:
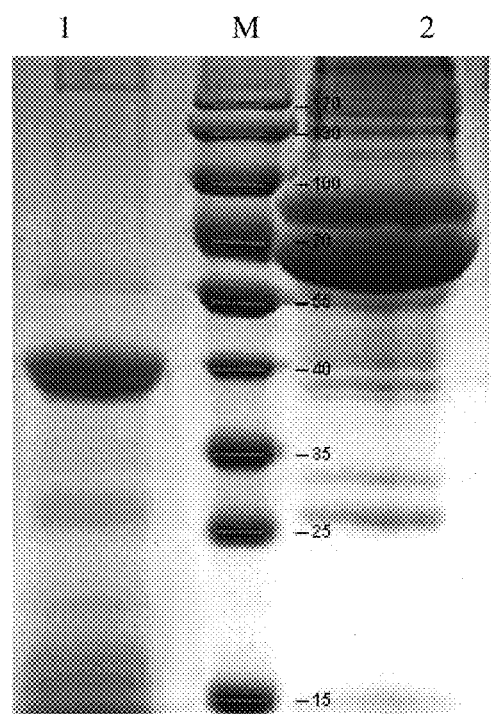
FIG. 38 shows the F(ab)$_2$ fragments after enzyme digestion and purification; Lane 1: F(ab)$_2$; Lane M: protein molecular weight markers; and Lane 2: the antibody.

A 60 IU/ml pepsin (Sigma, US) solution was formulated using an acetate buffer (sodium acetate 18 g, glacial acetic acid 9.8 mL, adding water to dilute to a volume of 1000 mL, pH 4.5). The pepsin solution was then added to the antibodies obtained in the previous step in a ratio of 1:11 (v/v), and maintained at 37° C. for 30 min. The reaction was stopped by adding 1 mol/L Tris-HCl buffer (pH 8.5). Purification by affinity chromatography was conducted using a pre-packed Protein G column as described above. The concentration was 1 mg/ml as detected by Lowry method. The results were shown in FIG. 38.

4) Verification of the Binding Between SpA and Human IgG Blocked by Anti-Recombinant Mutant Antibody F(ab)$_2$ Fragments The SpA5 protein was each diluted by 0.1 mol/L carbonate buffer (pH 9.5) to a concentration of 500 ng/ml. A 96-well ELISA plate was coated by the diluted protein solutions at 4° C. over night. The plate was then washed by the washing solution (Tris 2.42 g, Tween 20 0.5 mL, adjusted to pH=7.4 by concentrated HCl, adding ddH$_2$O to a total volume of 1000 mL) for 4 times. To each well, 200 μL blocking solution (5% (w/v) skimmed milk powder dissolved in 100 mmol/L TTBS (Tris (pH 7.5), Tween 20 0.1% (v/v), and NaCl 0.9% (w/v)) was added for blocking at 37° C. for 2 h. The liquid was discarded, and the plate was washed for 4 times by the washing solution. 100 μL human IgG-HRP (Beijing Zhongshan Golden Bridge Biotechnology Co. Ltd., Beijing) (1:5000) and 100 μL rabbit anti-mutant protein antibody F(ab)$_2$ fragments diluted to a concentration of 100 ng/ml were added to react at 37° C. for 60 min. The liquid was discarded, and the plate was washed for 4 times by the washing solution. 100 μL freshly prepared OPD-containing developing solution was added per well, and developed at room temperature in dark for 15 min. 50 μL 12.5% H$_2$SO$_4$ was then added to stop the reaction.

Figure 39:
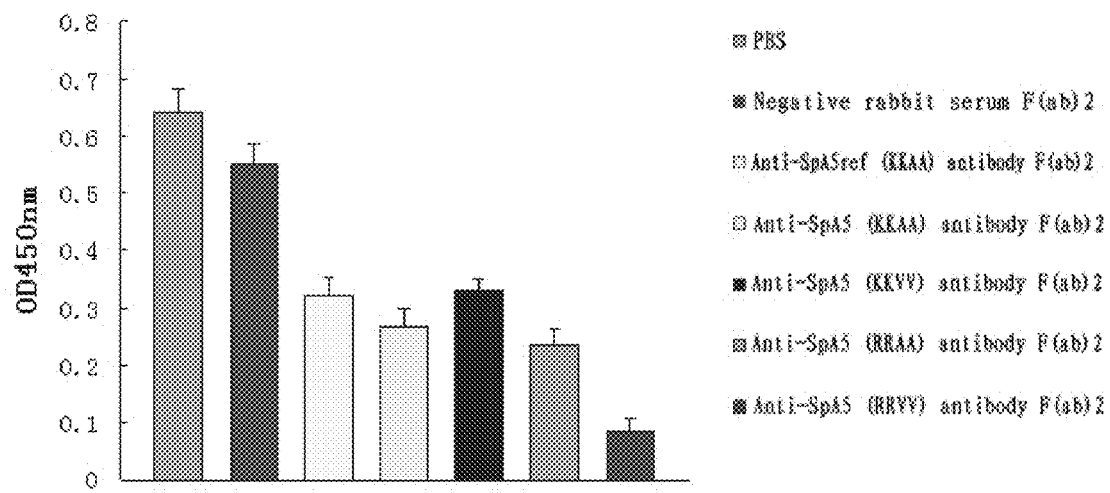
FIG. 39 shows the reduction of binding capacities of SpA to human IgG caused by antibody F(ab)$_2$ fragments produced in the rabbits immunized by each SpA5 protein tested using ELISA (mean value±stdev, n=5).

OD$_{450nm}$ was detected. Higher OD value indicated stronger binding to human IgG further suggesting that it was not suitable as an antigen candidate. The results were listed in table 3 and shown in FIG. 39.

TABLE 3

The ELISA results of binding between SpA and human IgG blocked by anti-recombinant mutant protein antibody F(ab)$_2$ fragments (OD$_{450\ nm}$)

|  |  |  |  |  |  | Ave | stdev | Paired t-test (compared with SpA5ref (KKAA) control) P |
|---|---|---|---|---|---|---|---|---|
| PBS | 0.636 | 0.665 | 0.601 | 0.698 | 0.605 | 0.641 | 0.041 |  |
| Negative rabbit serum F(ab)$_2$ | 0.593 | 0.547 | 0.558 | 0.497 | 0.568 | 0.553 | 0.035 |  |
| Anti-SpA5ref (KKAA) antibody F(ab)$_2$ | 0.289 | 0.363 | 0.293 | 0.345 | 0.313 | 0.321 | 0.032 | — |
| Anti-SpA5 (KKAA) antibody F(ab)$_2$ | 0.226 | 0.305 | 0.244 | 0.293 | 0.267 | 0.267 | 0.033 | <0.01 |
| Anti-SpA5 (KKVV)antibody F(ab)$_2$ | 0.351 | 0.320 | 0.343 | 0.342 | 0.299 | 0.331 | 0.021 | 0.628 |
| Anti-SpA5 (RRAA) antibody F(ab)$_2$ | 0.247 | 0.204 | 0.243 | 0.273 | 0.213 | 0.236 | 0.028 | <0.05 |
| Anti-SpA5 (RRVV) antibody F(ab)$_2$ | 0.102 | 0.068 | 0.075 | 0.115 | 0.067 | 0.085 | 0.022 | <0.01 |

As indicated by the results, the antibodies generated from each SpA5 protein of the invention would effectively bind to SpA, so that the binding capacity of the SpA to human IgG was reduced significantly, in which anti-SpA5 (RRVV) antibody F(ab)$_2$ reduced the most.

Example 8: Inductive Apoptosis of B Cells 1) 64 BALB/c mice (6-week old, body weight of about 16 g, Beijing HFK Bioscience Co., Ltd.) were randomly divided into 7 groups, with 8 mice in each group. The groups were designated as PBS group, SpA group, SpA5wt group and each mutant group.

2) For SpA group, purified SpA was injected I.P. at a dosage of 150 μg/mouse; for SpA5wt group, purified wild-type SpA5wt protein was injected I.P. at a dosage of 150 μg/mouse; for SpA5 mutant group, the purified SpA5 mutant protein was injected I.P. at a dosage of 150 μg/mouse; for PBS group, equal volume of PBS was injected.

3) 4 h later, mice were killed by breaking the neck. The spleens were taken from the mice in each group, and PBS was added. Single cell suspension was then prepared by a 200-mesh screen. Subsequently, the suspension was centrifugated at 1000 rpm for 5 min, and the supernatant was discarded.

4) Erythrocyte lysis solution (BD Biosciences, US) at 4° C. was added to the cell precipitate in a ratio of 1:5 (i.e. 5 mL lysis solution was added to 1 mL cell). The mixture was gently pipetted to homogeneity, and stood at room temperature for 5 min. Subsequently, it was centrifugated at 800-1000 rpm for 5 min, and the red supernatant was discarded and precipitate was then collected, to which Hank's solution (Hyclone, US) or serum-free medium 1640 (Hyclone, US) was added, followed by washing via centrifugation for 3 times. Complete medium 1640 (Hyclone, US) was then added to adjust the cell density to 2×10$^6$ cell/ml.

5) Cell collection: cells were collected directly to an U-shaped 96-well plate. Centrifugation: the U-shaped plate was centrifugated directly on an U-shaped plate rack at 1800 rpm for 5 min. After centrifugation, the supernatant was discarded, and the precipitate was re-suspended by 160 μL staining buffer (PBS+1% fetal bovine serum (GIBCO New Zealand). The suspension was then centrifugated in the same manner as described above; centrifugated in a 1.5 mL Ep tube at 1800 rpm for 5 min in a small centrifuge. After the supernatant was discarded, the precipitate was re-suspended by 1 mL staining buffer, and then centrifugated in the same manner as described above.

6) Flow cytometry staining: during centrifugation, the staining solution of recombinant phycoerythrin coupled anti-mouse CD19 antibody (eBioscience, US) was pre-prepared, and subsequently, diluted to 2-fold dilution as required. The solution was then added at 50 μL/well to the centrifugated wells above, and incubated at 4° C. for 30 min. The precipitate was slightly re-suspended by adding 100 μL staining buffer, and the mixture was centrifugated at 1800 rpm for 5 min. After the supernatant was discarded, 160 μL staining buffer was added for re-suspension. The mixture was then centrifugated at 1800 rpm for 5 min.

7) Detection by a flow cytometer: after the supernatant was discarded, the precipitate was re-suspended by adding 150 μL 1×PBS, and subsequently placed into a detection tube. Flow cytometry BD FACSCanto II was performed according to the procedure.

Figure 40:
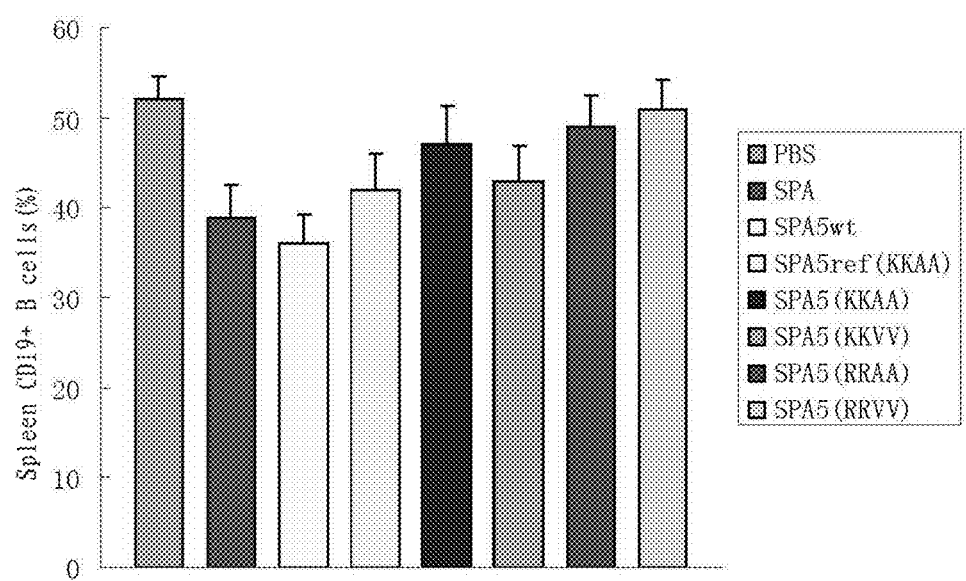
FIG. 40 shows the induced apoptosis of spleen B lymphocytes of the mice after immunization by SpA and each SpA5 protein.

The closer percentage of CD19+ leucocytes to that of the negative control indicated a weaker apoptosis-inducing capacity of the test protein, so that it was more suitable as an antigen candidate. The results were listed in Table 4 and shown in FIG. 40.

TABLE 4

Percentage of CD19+ B-cells

| | | | | | | | | | Mean | stdev | Paired t-test (compared with SpA5ref (KKAA)control) P |
|---|---|---|---|---|---|---|---|---|---|---|---|
| PBS | 54 | 51 | 52 | 48 | 56 | 51 | 50 | 54 | 52 | 2.6 | |
| SpA(252) | 40 | 36 | 42 | 43 | 35 | 43 | 34 | 39 | 39 | 3.6 | |
| SpA5wt | 33 | 39 | 33 | 39 | 34 | 39 | 31 | 40 | 36 | 3.6 | |
| SpA5ref(KKAA) | 36 | 48 | 40 | 44 | 39 | 45 | 39 | 45 | 42 | 4.1 | — |
| SpA5(KKAA) | 42 | 52 | 53 | 41 | 47 | 46 | 48 | 47 | 47 | 4.2 | <0.05 |
| SpA5(KKVV) | 41 | 47 | 49 | 38 | 39 | 45 | 42 | 43 | 43 | 3.8 | 0.558 |
| SpA5(RRAA) | 44 | 53 | 50 | 48 | 51 | 53 | 45 | 48 | 49 | 3.4 | <0.01 |
| SpA5(RRVV) | 54 | 52 | 47 | 53 | 47 | 53 | 48 | 54 | 51 | 3.1 | <0.01 |

As indicated by the results, apoptosis of mouse spleen B lymphocytes could be induced by both SpA (252) and SpA5wt, whereas for all mutant proteins, apoptosis could not be induced (Mean±stdev, n=8).

Based on the Examples above, the expression amount and the binding capacity to human IgG of each SpA5 protein of the invention, the capacity of the anti-SpA5 mutant antibody F(ab)$_2$ fragment to block the binding between SpA and human IgG and their B-cell apoptosis-inducing capacity were compared with those of SpA5ref (KKAA). The results were listed in Table 5.

TABLE 5

Summary of the properties of each SpA5 mutant

| | SpA5 (KKAA) | SpA5 (KKVV) | SpA5 (RRAA) | SpA5 (RRVV) |
|---|---|---|---|---|
| Expression amount | No difference | No difference | Relatively lower | Relatively lower |
| Binding capacity to human IgG | No difference | lower | No difference | Very significantly lower |
| Capacity to block binding between SpA and human IgG by antibody F(ab)$_2$ fragment | Very significantly higher | No difference | Significantly higher | Very significantly higher |
| B-cell apoptosis-inducing capacity | Significantly lower | No difference | Very significantly lower | Very significantly lower |

Example 9: Preparation of the SpA5 Vaccine

Aluminum phosphate adjuvant was an imported product with original packaging from GENERAL CHEMICAL corporation (US) (concentration of element aluminium: 5.3-5.4 mg/ml);

1. Preparation of *Staphylococcus aureus* Recombinant SpA5 Vaccine (1) Exact 800 μL aluminum phosphate adjuvant was measured out and placed into a formulation bottle. Subsequently, 2200 μL vaccine diluent (histidine 10 mM, NaCl 0.9%, poloxamer 188 0.01%, pH 6.0) was measured out and added to the bottle to a final volume of 3000 μL. The solution was then fully mixed.

(2) Each SpA5 protein was diluted to a concentration of 300 μg/3000 μL by the vaccine diluent, and fully mixed;

(3) The diluted adjuvant solution was added with the diluted protein solution of the same volume to a formulation bottle. The mixture was then suspended vertically or stirred horizontally at the temperature in the range from 4 to 37° C. After adsorption for 1 h, the vaccine was prepared.

2. Adsorption Homogeneity and Completeness of the Recombinant Antigen Proteins in the *Staphylococcus aureus* Vaccine by the Aluminum Phosphate Adjuvant as Characterized by 12% SDS-PAGE (1) 1 mL vaccine formulation as described above was centrifugated at 6000 rpm for 5 min at 4° C. The supernatant after centrifugation was carefully taken out, from which 40 μL sample was withdrawn.

(2) The dissociation solution (1 M Na$_2$CO$_3$) was added of the same volume as the supernatant withdrawn, and suspended vertically at room temperature for 1 h. Subsequently, 40 μL suspension was sampled.

(3) Protein solution free of the aluminum phosphate adjuvant was prepared according to the method described above in 1, in which the volume of the aluminum phosphate solution was substituted by the vaccine diluent. After fully mixed, 40 μL sample was collected.

(4) To the sample collected, 10 μL 5× loading buffer was added. The mixture was then heated at 100° C. for 5 min. After cooling down, the samples were centrifugated instantly. 10 μL samples were loaded to the gel.

Figure 41:
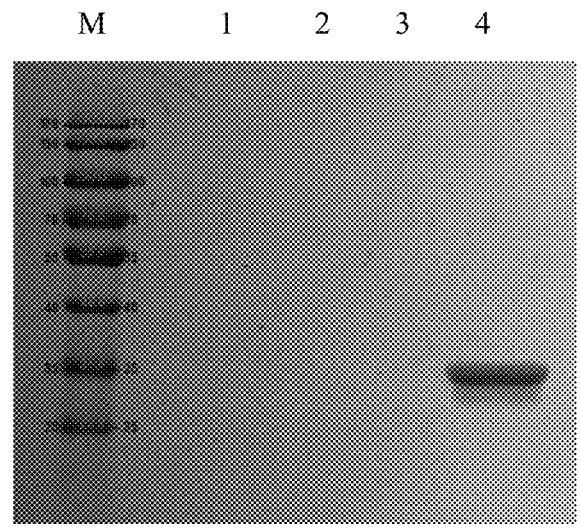
FIG. 41 shows 12% SDS-PAGE analysis before and after SpA5 adsorption by aluminum phosphate; Lane 1: the supernatant obtained by centrifugation after adsorption by aluminum phosphate: SpA5ref (KKAA); Lane 2: the supernatant obtained by centrifugation after adsorption by aluminum phosphate: SpA5 (KKAA); Lane 3: the supernatant obtained by centrifugation after adsorption by aluminum phosphate: SpA5 (RRVV); and Lane 4: protein solution (using SpA5 (KKAA) as a control).

(5) The procedure for 12% SDS-PAGE included initially running at 80 v for 20 min, and then at 180 v for 40 min. After running, the gel was stained in a Coomassie staining solution under shaking, followed by destaining in a destaining solution under shaking. The gel was observed in an imaging system. The results were shown in FIG. 41, which indicated that the proteins could be fully adsorbed by the aluminum phosphate adjuvant.

Example 10: Establishment of a Standard Curve for Quantitative Analysis of the *Staphylococcus aureus* Strain (International Standard Strain MRSA-252) Used for Infection The strain was inoculated to an MH agar plate, and incubated at 37° C. for 24 h. Single colony was individually picked up from the plate, inoculated to MH liquid medium, and incubated at 37° C. in a shaker for 6 h. Subsequently, bacteria were collected by centrifugation at 6000 rpm for 10 min, and washed twice by physiological saline. The bacteria solution was diluted to 10- and 1.25-fold, respectively. The absorbance at 600 nm ($OD_{600}$) was detected by an ultraviolet spectrometry for each bacteria solution. 100 μL diluted bacteria solution was smeared on an MH agar plate, and incubated at 37° C. for 24 h, followed by colony counting. Based on the colony numbers on each plate and the $OD_{600}$ values for bacteria solution, a standard curve was established.

Results: the equation for the standard curve was Y=2.3065X+0.0051 ($10^9$ CFU/ml), with a correlation coefficient of 0.9999.

Example 11: Establishment of a Septicopyemia Animal Model

1. MRSA-252 was inoculated to an MH agar plate, and incubated at 37° C. for 24 h. Single colony was individually picked up from the plate, inoculated to MH liquid medium, and incubated at 37° C. in a shaker for 6 h and the bacteria were collected. Based on the standard curve, the bacteria were quantified, and the bacteria solution was diluted (or concentrated) to various concentrations, including $2.0\times10^{10}$ CFU/mL, $1.5\times10^{10}$ CFU/mL, $1.25\times10^{10}$ CFU/mL, and $1.0\times10^{10}$ CFU/mL. Subsequently, BALB/C mice (6-8 weeks old, body weight of 18-20 g) were systemically infected by the bacteria solutions of various concentrations through tail intravenous injection (100 μL/animal). The physiological saline was used as a control. After observed for 7 days, the death rate was determined for each group.

2. The amount of colonized bacteria was detected by colony counting every 24 h after infection (until Day 7 after infection): 3 mice were randomly selected from each of the infection groups and control group, from which 0.5-1 mL blood sample was taken by eyeball enucleation. 20 μL blood sample was diluted 10 folds in 180 μL heparin for bacteria counting. 50 μL sample was smeared on an agar plate, and incubated at 37° C. for 24 h for clone counting. The mice were killed after blood sample collection. After sterilization by soaking in 75% aqueous alcohol solution, the limbs of mice were fixed. Subsequently, the mice were dissected and the spleen, kidney, and liver were taken out, and placed in 2 mL sterile PBS. The organs were homogenized in a clean glass homogenizer, and 1 mL homogenate was each diluted in a ratio of 1:10, 1:100, or 1:1000. 100 μL of each dilution was gently smeared on solid medium, and incubated at 37° C. for 24 h for colony counting. The results were listed in Table 6.

TABLE 6

Minimum lethal dose and sub-lethal dose of MRSA-252

| MRSA-252 dose for infection | Number of mice | Number of the mice died at various times | | | | | | | | Total number of dead mice | Mortality rate (%) |
| --- | --- | --- | --- | --- | --- | --- | --- | --- | --- | --- | --- |
| | | 12 h | 24 h | 48 h | 72 h | 96 d | 120 d | 6 d | 7 d | | |
| $2.0\times10^9$ CFU | 30 | 30 | 0 | 0 | 0 | 0 | 0 | 0 | 0 | 30 | 100 |
| $1.5\times10^9$ CFU | 30 | 0 | 3 | 24 | 3 | 0 | 0 | 0 | 0 | 30 | 100 |
| $1.25\times10^9$ CFU | 30 | 0 | 0 | 24 | 0 | 3 | 3 | 0 | 0 | 30 | 100 |
| $1.0\times10^9$ CFU | 30 | 0 | 0 | 3 | 3 | 6 | 9 | 0 | 0 | 21 | 70 |

In the dosage group of $2.0\times10^9$ CFU, the mortality rate was 100% within 12 hours (h); in the dosage group of $1.5\times10^9$ CFU, the mortality rate was 90% within 48 h, and 100% within 72 h; in the dosage group of $1.25\times10^9$ CFU, the mortality rate was 80% within 48 h, 90% within 96 h, and 100% within 120 h; in the dosage group of $1.0\times10^9$ CFU, the mortality rate was 10% within 48 h, 20% within 72 h, and 70% with in 7 days (d). Accordingly, the minimum lethal dose of MRSA-252 was $1.25\times10^9$ CFU, and the sub-lethal dose was $1.0$-$1.25\times10^9$ CFU.

3. Colonization counts in blood and various organs in the BALB/C mouse infected by MRSA-252

A peak value of bacteria was attained in blood at 48 h after infection, with maximal colonization counts of $8.0\times10^9$ CFU/ml. The amount of bacteria in blood started to decrease from 72 h, and no bacterium was detected at 96 h. The peak values of bacteria colonized in spleen, kidney, and liver were all reached at 72 h after infection, with maximal colonization counts of $8.0\times10^9$ CFU/ml. In control group, the colonization counts in blood, spleen, kidney, and liver were all 0.

In the results above, the survival rate of mice and colonization counts of bacteria in blood, and major organs, including spleen, kidney, and liver were evaluated in an animal model, which provided a basis for successful development of single subunit vaccine and multi-subunit fusion vaccine of SA, and for researches on the pathogenesis of SA infections.

Example 12: The Effect of SpA5 as an Antigen Determined by Immune Protection Against Challenging in Animals 1. According to the method of Example 9, SpA5ref (KKAA), SpA5 (KKAA) and SpA5 (RRVV) were prepared into vaccines.

2. Experiment animals and group division

Female BALB/C mice of 6-week old were used (Beijing HFK Bioscience Co., Ltd.). The animals were divided into 5 groups, including vaccine diluent group, aluminum phosphate adjuvant control group, SpA5ref (KKAA) group, SpA5 (KKAA) group and SpA5 (RRVV) group, with 30 mice in each group.

3. Immunization was performed by quadriceps femoris injection of each vaccine for 3 times (Day 0, 14, and 21) at a dosage of 30 μg/100 μL.

4. The procedure of challenging: after the last immunization, viable MRSA-252 was injected via caudal vein at a lethal dose on Day 14 for challenging test. The amount of bacteria suspension was $1.25 \times 10^9$ CFU (determined based on the results listed in Table 6) for each BALB/C mouse. After observed for 10 days, the survival rate was calculated for each group.

5. The results were listed in Table 7.

TABLE 7

Protective capacity against challenging after immunization by each SpA5 mutant protein

| Groups | Number of survival animals after 10 days | Survival rate |
|---|---|---|
| Vaccine diluent | 4 | 13% |
| AlPO$_4$ | 6 | 20% |
| SpA5(KKAA) | 11 | 37% |
| SpA5(RRVV) | 12 | 40% |
| SpA5ref(KKAA) | 10 | 33% |

As indicated by the results listed in the Table above, favorable protective effects of SpA5 (KKAA) and SpA5 (RRVV) were observed for the animals.

B. Method for Detecting SpA5-Specific IgG

The SpA5 protein of the invention had strong immunogenicity, and could used as an antigen candidate for the *Staphylococcus aureus* vaccine. However, SpA5 was still able to partially bind the Fc fragment of mammalian IgG resulting in difficulties in detecting SpA5 antigen specific IgG As indicated by previous results of serum detection in the animals immunized by SpA5, the inventors found that the plate coated by the mutant SpA5 protein reacted with the serum in negative control group, and presented a weakly positive result, due to non-specific binding between SpA5 and the Fc fragment of IgG in the serum.

On such a basis, it was intended to provide a detection method for SpA5 specific antibody without non-specific interference.

Some parts of peptide chains of the immunoglobulin could be easily hydrolyzed by proteases into different fragments. As one of the most used proteolytic enzymes, pepsin was used to hydrolyze IgG into one F(ab')$_2$ fragment and some small fragments pFc'. F(ab')$_2$ was a divalent structure composed of 2 Fab fragments and a hinge region, which retained its biological activity of binding to corresponding antigens, and avoided the side effect of the immunogenicity of Fc fragment. After hydrolysis by pepsin, pFc' was finally degraded and lost its biological activity. Based on the techniques above, the SpA5 antigen specific IgG antibodies were detected in the serum of different animals immunized by the recombinant *Staphylococcus aureus* vaccines. At present, no related research has been reported yet.

In this section, the present invention provided a method for detecting the SpA5 antigen specific IgG antibody. Using this method, non-specific binding between SpA5 and the Fc fragment of IgG antibody was avoided, so that the SpA5 antigen specific IgG antibodies could be detected in various species after immunization by the vaccines. This method provided a basis for researches on the antigenicity, immunogenicity and immunoprotection of SpA5.

In the first aspect, the method for detecting the SpA5 antigen specific IgG antibody of the invention comprised: 1) obtaining the serum of the animal immunized by the SpA5 protein, and digesting the antibody in the serum by pepsin to obtain F(ab')$_2$ fragments of the antibody; 2) detecting the SpA5 specific F(ab')$_2$ fragment IgG antibody by ELISA.

Specific steps of the method were as follows:

1) Antibody preparation: the blood samples collected after immunization of animals by the SpA5 protein were placed at 4° C. for 2 h, and then centrifugated at 8000 rpm/min for 10 min at 4° C. The supernatant serum was withdrawn, and stored at −20° C. for further use.

2) Preparation of the digestion solution: to 0.1-0.2 M sodium acetate solution, pepsin was added to a final activity of 30-150 IU/mL, and preferably, 60 IU/mL. The pH value was adjusted to 4.0-4.6.

3) the serum obtained in step 1) was diluted 10 folds by the digestion solution prepared in step 2). After fully mixed, digestion was performed in a water bath at 37° C. for 6 h. During digestion, the mixture was shaken to mix well for 5-10 min at an interval of 1 h. In this step, an F(ab')$_2$ fragment and some small fragments pFc' were obtained after digestion of antibody by pepsin, avoiding the interference of the Fc fragment.

4) SpA5 specific F(ab')$_2$ fragment IgG antibody titer was detected by ELISA using the purified SpA5 protein; preferably, an ELISA plate was coated by the SpA5 protein at a concentration of 2 μg/ml. Subsequently, after the digested sample in step 3) was diluted by the antibody diluent in a ratio of 1:2000, the SpA5 specific F(ab')$_2$ fragment IgG antibody titer was detected by a series of fold-dilutions.

In another aspect, the present invention provides a kit for detection of the SpA5 antigen specific IgG antibody, which comprises: enzyme digestion buffer, pepsin, and reagents for ELISA. Preferably, the enzyme digestion buffer was 0.1-0.2 M sodium acetate solution; and preferably, the reagents for ELISA includes: coating solution, antibody diluent, washing solution, blocking solution and stopping solution. The reagents required for ELISA could easily determined by the one skilled in the art based on common skills in the field.

In the present invention, in order to obtain the antibody titer in the serum, the SpA5 specific IgG antibody in the serum of the animal immunized by the SpA5 vaccine was detected using digestion by pepsin and ELISA test. In this method, the specificity was enhanced by excluding the interference of non-specific binding between SpA and the Fc fragment of antibody. Meanwhile, the method had advantages of simple operation and good repeatability. Additionally, the method was verified by the antibody detection in the serums among various species (BALB/C mouse, SD rat, and New Zealand big ear white rabbit). The method could be used for researches on immunogenicity and antigenicity of the recombinant *Staphylococcus aureus* vaccines.

The materials and primary reagents used in this section were as follows:

1. Experiment Animals

BALB/C mice (Beijing HFK Bioscience Co., Ltd.), SD rats (Beijing Charles River Laboratories. Inc.) and New Zealand big ear white rabbits (Laboratory Animal Center, Third Military Medical University).

2. Materials

SpA5 (KKAA) (30 μg/600 μL) vaccine formulation.

3. Primary Reagents

Glycine and pepsin were purchased from Shanghai Sangon Biotech. Inc. Ordinary and F(ab')$_2$ fragment goat anti-mouse, rat and rabbit IgG secondary antibodies were supplied by Shanghai Hengdailao Commerce Co., Ltd. Soluble substrate solutions of individual component were obtained from an agent in Chongqing of Tiangen Biotech (Beijing) Co., Ltd. Sodium chloride, potassium dihydrogen phosphate, disodium hydrogen phosphate dodecahydrate, and Polysorbate 20 were obtained from Sinopharm Chemical Reagent Co. Ltd. Potassium chloride was purchased from Chengdu Kelong Chemical Reagent Factory. PBS buffer was from Beijing Zhongshan Golden Bridge Biotechnology Co. Ltd.

4. Preparation of Reagents 1) enzyme digestion solution: to 0.1-0.2 M sodium acetate solution, pepsin was added to a final activity of 60 IU/mL, and the pH value was adjusted to 4.0-4.6.

2) Reagents for ELISA

① Coating solution: 1.6 g $Na_2CO_3$ and 2.9 g $NaHCO_3$ were weighed on a electronic balance, and the pH value was adjusted to 9.6, distilled water was added to a final volume of 1000 mL.

② Antibody diluent: 8 g NaCl, 0.2 g $KH_2PO_4$, 2.9 g $Na_2HPO_4.12H_2O$, 0.2 g KCl were weighed on a electronic balance, 0.5 mL Tween 20, and the pH value was adjusted to 7.4, distilled water was added to a final volume of 1000 mL.

③ Washing solution: 0.05% Tween 20-PBS (pH 7.4)

1 bag of 1000 mL/bag PBS was dissolved in 1000 mL pure water, followed by adding 0.5 mL Tween 20.

④ Blocking solution (freshly prepared)

BSA was added in a ratio of 1% to 20 mL antibody diluent, and stored at 4° C. for further use.

⑤ Stopping solution (2 mol/L sulphuric acid solution)

22.2 mL concentrated sulfuric acid was added to 177.8 mL dd$H_2O$.

Example 13: Animal Immunization and Preparation of Immunized Serum

1) Group division of animals: the animals were randomly divided into immunization group by vaccine and control group. The groups were listed in Table 8.

TABLE 8

Group division of experiment animals for immunogenicity investigation

| Animal species | Immunization group by vaccine | Control group |
| --- | --- | --- |
| BALB/C mouse | 10 | 10 |
| SD rat | 5 | 5 |
| New Zealand big ear white rabbit | 2 | 2 |

2) Immunization of the experiment animals: for immunization group, the animals were immunized by intramuscular injection of a dose of SpA5 (KKAA) (600 μL) per animal; for control group, physiological saline of the same volume was used. The procedure included immunization for 3 times on Day 0, Day 14 and Day 21.

3) Blood collection: blood was collected on Day 14 after the last immunization. The blood sample was collected by eyeball enucleation for mice, via caudal vein for rats, and via auricular vein for rabbits. The blood was incubated at 4° C. for 2 h, and then centrifugated at 8000 rpm for 10 min. Subsequently, the serum was separated and stored at −20° C. for further use.

Example 14: Digestion of Antibodies in the Serum by Pepsin

20 μL serum obtained in Example 13 was added to 180 μL enzyme digestion solution. After fully mixed, the serum was digested in a water bath at 37° C. for 6 h. During digestion, the mixture was shaken to mix well for 5 min at an interval of 1 h.

Example 15: Detection of Specific Anti-SpA5 (KKAA) Antibody

Methods

1) Coating: purified SpA5 (KKAA) protein was diluted to 2 μg/mL by the coating solution. An ELISA plate was then coated at a concentration of 100 μL/well. After fully shaken for homogeneity, the plate was placed in a refrigerator at 4° C. overnight or at 37° C. for 2 h.

2) Blocking: the plate was washed by the washing solution (4 times, each 300 μL). For each washing, the plate was shaken for 30 s and the washing solution was pipetted for 2.5 s. The ELISA strip was blocked by the blocking solution at 200 μL/well, and placed in a refrigerator at 4° C. overnight or at 37° C. for 2 h.

3) Addition of the primary antibody: the plate was washed by the washing solution (4 times, each 300 μL). For each washing, the plate was shaken for 30 s and the washing solution was pipetted for 2.5 s. The serum digested above was diluted by 200 folds to 1:2000. Subsequently, a series of 7 2-fold dilutions were obtained using the antibody diluent. The resulting dilutions were homogenously mixed by shaking. The diluted samples were added to an ELISA plate at 100 μL/well, and incubated at 37° C. for 40 min.

4) Addition of the secondary antibody: the plate was washed by the washing solution (4 times, each 300 μL). For each washing, the plate was shaken for 30 s and the washing solution was pipetted for 2.5 s. Goat anti-mouse, rat and rabbit IgG F(ab')$_2$ fragment secondary antibody labeled by HRP was diluted by the antibody diluent to 1:10000. The dilutions were added at 100 μL/well to the plate, homogenously mixed by shaking, and incubated at 37° C. for 40 min. Meanwhile, common goat anti-mouse, rat and rabbit IgG secondary antibodies were used as a control.

5) Developing: the plate was washed by the washing solution (4 times, each 300 μL). For each washing, the plate was shaken for 30 s and the washing solution was pipetted for 2.5 s. The developing solution was added at 100 μL/well. The mixture was then developed in dark for 5-10 min.

6) Termination of the reaction: after developing, 2 mol/L $H_2SO_4$ was added at 50 μL/well to stop the reaction. OD values for each well were detected at 492 nm by a microplate reader.

7) Statistical analysis: $A_{sample}/A_{negative} > 2.1$ was regarded as positive standard. The maximal dilution was determined for each specific antibody in the serum. A histogram was plotted using the geometric mean titer.

Figure 42:
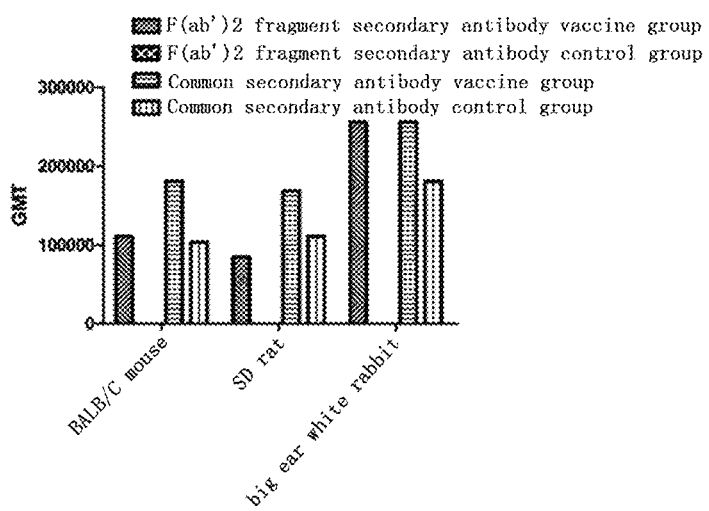
FIG. 42 is a graph showing the geometric mean antibody titer in the serum of the animal in each group.

Results:

As shown in Table 9, the ELISA results indicated that: the results of immunization by vaccine group and control group are similar when a common IgG secondary antibody was used in the detection, since SpA5 (KKAA) comprised an IgG binding domain, which non-specifically bound to the Fc fragment of the mammalian IgG antibody, there was no significant difference. When goat anti-mouse, rat and rabbit IgG F(ab')$_2$ fragment secondary antibody was used, negative results were observed for all samples in control group, so that non-specific interference was avoided. By using this method, the actual level of SpA5 (KKAA) specific IgG antibody in the serum can be detected more precisely, with higher specificity. In order to analyze the results, a histogram was plotted using the geometric mean titer (GMT) of the antibody detected in the serum of mice in individual experiment groups of various species, as shown in FIG. 42.

TABLE 9

Detection of the specific antibody titer in the serum of various animals immunized by SpA

| | Immunization by vaccine group | | | | Control group | | |
|---|---|---|---|---|---|---|---|
| Animal species | No. | F(ab')$_2$ fragment secondary antibody | Common secondary antibody | Animal species | No. | F(ab')$_2$ fragment secondary antibody | Common secondary antibody |
| BALB/C mouse | 1 | 1:64000 | 1:128000 | BALB/C mouse | 1 | — | 1:128000 |
| BALB/C mouse | 2 | 1:128000 | 1:128000 | BALB/C mouse | 2 | — | 1:64000 |
| BALB/C mouse | 3 | 1:128000 | 1:256000 | BALB/C mouse | 3 | — | 1:128000 |
| BALB/C mouse | 4 | 1:64000 | 1:128000 | BALB/C mouse | 4 | — | 1:128000 |
| BALB/C mouse | 5 | 1:128000 | 1:256000 | BALB/C mouse | 5 | — | 1:64000 |
| BALB/C mouse | 6 | 1:128000 | 1:256000 | BALB/C mouse | 6 | — | 1:128000 |
| BALB/C mouse | 7 | 1:256000 | 1:256000 | BALB/C mouse | 7 | — | 1:128000 |
| BALB/C mouse | 8 | 1:128000 | 1:128000 | BALB/C mouse | 8 | — | 1:128000 |
| BALB/C mouse | 9 | 1:128000 | 1:256000 | BALB/C mouse | 9 | — | 1:128000 |
| BALB/C mouse | 10 | 1:64000 | 1:128000 | BALB/C mouse | 10 | — | 1:64000 |
| SD rat | 1 | 1:128000 | 1:256000 | SD rat | 1 | — | 1:128000 |
| SD rat | 2 | 1:64000 | 1:128000 | SD rat | 2 | — | 1:128000 |
| SD rat | 3 | 1:128000 | 1:128000 | SD rat | 3 | — | 1:128000 |
| SD rat | 4 | 1:128000 | 1:256000 | SD rat | 4 | — | 1:128000 |
| SD rat | 5 | 1:32000 | 1:128000 | SD rat | 5 | — | 1:64000 |
| big ear white rabbit | 1 | 1:256000 | 1:256000 | big ear white rabbit | 1 | — | 1:128000 |
| big ear white rabbit | 2 | 1:256000 | 1:256000 | big ear white rabbit | 2 | — | 1:256000 |

Based on the Examples above, related detection kits can be easily prepared by the one skilled in the art by using the detection method provided herein according to the knowledge in the field, for evaluation of the specific antibody level after immunized by the SpA5 mutant protein and for assessment of the immunoprotective effects.

C. Vaccine Formulations and the Preparation Methods Thereof

The vaccine formulations of the invention were based on the SpA5 proteins of the invention, and HI, MntC and mSEB proteins.

In one embodiment, the vaccine formulations of the invention includes the SpA5 proteins; and in another embodiment, the vaccine formulations of the invention includes the SpA5 proteins, and one or more of MntC, mSEB and HI proteins.

Preferably, the sequence of the SpA5 protein was selected from any one of SEQ ID NO. 1-4; the sequence of MntC protein was shown in SEQ ID NO. 13; the sequence of mSEB protein was shown in SEQ ID NO. 14; and the sequence of HI protein was shown in SEQ ID NO. 15. More preferably, in the vaccine formulations of the invention, the SpA5 protein was SpA5 (KKAA) or SpA5 (RRVV).

In a preferable embodiment, the antigen in the vaccine formulations of the invention consists of SpA5, MntC, mSEB and HI proteins. The concentration of each antigen was in the range from 10-100 μg/ml, and preferably, was 50 μg/ml.

Preferably, the vaccine formulations further comprises an adjuvant, and preferably, the adjuvant was an aluminium adjuvant, such as aluminum phosphate or aluminium hydroxide. The reagents used to prepare the vaccine formulations could be easily determined by the one skilled in the art.

The vaccine formulations above contains a plurality of antigens screened from 2742 open reading frames (ORFs) in the whole genome of *Staphylococcus aureus* by the inventors through reverse vaccinology, high-throughput immunodominant antigenome, highly efficient expression and purification of soluble protein and through a large number of experiments for evaluating the immunoprotective effects on animals, wherein the screened antigens has strong antigenicity, favorable specificity and conservation, and good protective effects. The antigens includes: α-hemolysin (Hla), iron-regulated surface determinant protein B (IsdB), *Staphylococcus aureus* protein A (SpA), enterotoxin B (SEB), and manganese ion-binding protein C (MntC). These antigens plays an important role in key points of *Staphylococcus aureus* infection and immunologic escape. In the present invention, the recombinant *Staphylococcus aureus* vaccines containing the antigens above and the compositions thereof were successfully prepared, based on structure analysis, molecular fusion, selection of multiple components, and optimization components compatibility. Invasion by *Staphylococcus aureus* infections can be effectively protected against by the vaccines, since they blocked the metabolic pathway of *Staphylococcus aureus*, inhibited adhesion and colonization, controlled the diffusion of toxins, and destroyed immunologic escape.

Due to complex antigen components in the vaccines of the invention, and varied properties of each antigen, it was difficult to prepare a single component vaccine formulation directly using one antigen. The method for preparing a single component vaccine formulation was complicated, with undesired immune effect, so it was not suitable for industrial production. Besides, the adsorption rate by the aluminium adjuvant varied among different antigens, and the homogeneity in adsorption was also different, so that higher dosage was usually desired for vaccination, while the immunoprotective effects were often not desired. Additionally, the physicochemical properties of the aluminium adjuvant might change during preparation, resulting in ineffective immunization by the vaccine formulations.

Principal problems includes: (1) no unified evaluation criteria for the mixing ratio between the antigen and the element aluminium in the prior art, in which extremely high content of element aluminium was used to obtain a higher adsorption rate, which was harmful to the health of patients, went against related requirements of WHO and in "Guidelines for Preclinical Research on Preventive Vaccines", and furthermore, did not conform to the trend in pharmaceutical industry. (2) The existing procedure for vaccine formulation was in an order of diluting the antigens and the adjuvants separately, adsorbing, mixing and subpackaging, which was feasible for formulating a single antigen component, but not for multi-component formulations, due to enhanced difficulties and costs with increased number of antigen components. (3) To address the problems above, a method, in which the diluted adjuvant was directly added to the antigen, was proposed, however, the adsorption homogeneity could not be guaranteed for multi-component formulation by this method. (4) There was no scientific and rigorous evaluation system in the field of formulation; in the prior art, only the preparation method for the adjuvant was focused, while the formulation process was often neglected; for the evaluation indices, attentions were usually paid to the adsorption rate, while other indices were generally ignored, such as the adsorption mode, the adsorption efficiency, the adsorption homogeneity and the detection methods thereof, and the stability of various parameters in the formulation process etc. (5) For the histidine solution at present, the applicability was still restricted for the proteins of different properties, although parameters, such as histidine concentration and pH value etc., were investigated; while in some vaccine formulation processes, solubilizing agents, such as Tween, were added, it had already been less used in the FDA approved medicines due to problems such as potential safety hazard, and unfortunately no novel solubilizing agent was reported yet. (6) In conventional formulation processes, horizontal mixing mode was usually used for adsorption, and innovation and development in techniques and equipments were still demanded.

Accordingly, there was a demand to improve and innovate the process related to the vaccine formulation processes at present, so that key bottlenecks in the process of vaccine formulation could be efficiently settled, such as the adsorption rate of antigen protein, the adsorption homogeneity of multiple antigen components, the stability, the reasonable and effective adsorption mode, making the vaccine formulation process (especially for multi-component vaccine formulation) simpler, more stable and more efficient, with reduced production costs.

Thus, in another aspect, the present invention provided a method for preparing a multi-component vaccine, which comprises diluting the aluminium adjuvant and the vaccine antigen protein separately, followed by mixing and/or adsorbing, specifically includes:

Method 1: individual vaccine antigen proteins were diluted by the vaccine diluent separately, and then each mixed with the aluminum phosphate adjuvant of an equal volume diluted by the vaccine diluent, and adsorbed. Subsequently, the protein solutions were mixed homogenously and subpackaged.

(1) According to the concentration of element aluminium (5.3 mg/ml) in the aluminum phosphate adjuvant solution and the final concentration of element aluminium (0.71 mg/ml) in the finished vaccine product, the required volume of aluminum phosphate adjuvant solution was calculated, exactly taken out, and added to a formulation bottle. Vaccine diluent was then added to 50% of the final volume of the vaccine formulation. The mixture was sufficiently mixed.

(2) The final concentration of the recombinant *Staphylococcus aureus* vaccine antigen proteins was 0.2 mg/ml, and the final concentration of an individual recombinant *Staphylococcus aureus* vaccine antigen protein was 0.05 mg/ml. According to the volume required, the amount of each protein was calculated. Exact volume of the individual recombinant *Staphylococcus aureus* vaccine antigen protein solution was then added to a formulation bottle. Vaccine diluent was then added to 12.5% of the final volume of the vaccine formulation. The mixture was sufficiently mixed.

(3) Each diluted individual antigen protein solution and the diluted adjuvant solution of the same volume were added to subpackage bottles. The mixture was suspended vertically at 14 rpm for adsorption for 1 h at ambient temperature controlled in the range from 4-37° C.

(4) After adsorption, the formulation was prepared by fully mixing 4 antigen protein solutions.

Method 2: individual vaccine antigen proteins were diluted by the vaccine diluent separately, and then each mixed with the diluted aluminum phosphate adjuvant of an equal volume. Subsequently, the protein solutions were mixed and adsorbed all together, and then subpackaged.

(1) According to the concentration of element aluminium (5.3 mg/ml) in the aluminum phosphate adjuvant solution and the final concentration of element aluminium (0.71 mg/ml) in the finished vaccine product, the required volume of aluminum phosphate adjuvant solution was calculated, exactly taken out, and added to a formulation bottle. Vaccine diluent was then added to 50% of the final volume of the vaccine formulation. The mixture was sufficiently mixed.

(2) The final concentration of the recombinant *Staphylococcus aureus* vaccine antigen proteins was 0.2 mg/ml, and the final concentration of an individual recombinant *Staphylococcus aureus* vaccine antigen protein was 0.05 mg/ml. According to the volume required, the amount of each protein was calculated. Exact volumes of individual recombinant *Staphylococcus aureus* vaccine antigen protein solutions were then added to formulation bottles. Vaccine diluent was then added to 12.5% of the final volume of the vaccine formulation. The mixture was sufficiently mixed.

(3) Each diluted individual antigen protein solution and the diluted adjuvant solution of the same volume were added to subpackage bottles. Subsequently, 4 antigen protein solutions were mixed, and suspended vertically at 14 rpm for adsorption for 1 h at ambient temperature controlled in the range from 4-37° C.

Method 3: multiple vaccine antigen proteins were mixed and diluted by the vaccine diluent. After fully mixed, the solution was then mixed with the diluted aluminum phosphate adjuvant solution of an equal volume. After adsorption, the solution was subpackaged.

(1) According to the concentration of element aluminium (5.3 mg/ml) in the aluminum phosphate adjuvant solution and the final concentration of element aluminium (0.71 mg/ml) in the finished vaccine product, the required volume of aluminum phosphate adjuvant solution was calculated, exactly taken out, and added to a formulation bottle. Vaccine diluent was then added to 50% of the final volume of the vaccine formulation. The mixture was sufficiently mixed.

(2) The final concentration of the recombinant *Staphylococcus aureus* vaccine antigen proteins was 0.2 mg/ml, and the final concentration of an individual recombinant *Staphylococcus aureus* vaccine antigen protein was 0.05 mg/ml. According to the volume required, the amount of each protein was calculated. Exact volumes of 4 required recombinant *Staphylococcus aureus* vaccine antigen protein solutions were then added to a formulation bottle. Vaccine diluent was then added to 50% of the final volume of the vaccine formulation. The mixture was sufficiently mixed.

(3) The above diluted antigen protein solution and the diluted adjuvant solution were added to a subpackge bottle. The mixture was suspended vertically at 14 rpm for adsorption for 1 h at ambient temperature controlled in the range from 4-37° C.

Preferably, the vertical suspension could be substituted by horizontal suspension.

Preferably, the ratio between the diluted aluminum phosphate adjuvant solution and the diluted antigen protein solution was 1:1.

Preferably, the aluminum phosphate adjuvant could be substituted by aluminium hydroxide adjuvant.

Preferably, the mass ratio between the antigen protein and the element aluminium was 1:1.98, at which the adsorption rate could reach 90%-100%.

Preferably, the vaccine diluent used was histidine buffer, which consists of histidine (preferably, at concentration of 10 mmol/L), poloxamer 188 (preferably, 0.02%), and sodium chloride (preferably, at concentration of 0.9%), at a preferable pH value of 6.0.

The vaccine formulation prepared according to the method of the invention was stable for more than 8 weeks at the temperature ranged from 4° C. to 37° C.

The advantages of the method provided herein includes:

(1) Based on the problems such as lack of or defective evaluation system for formulation in the prior art, existing verification indices have been optimized in the present invention, besides the conventional parameter adsorption rate, indices including the weight ratio of components, the adsorption efficiency, the stability, the homogeneity and the detection methods thereof etc, and the stability of the parameters mentioned, have been proposed; and a set of evaluation system for formulation process was established, mainly based on the indices including the adsorption rate, the adsorption efficiency, the weight ratio of components, the homogeneity, and the stability, so that the formulation process could be scientifically, precisely and rapidly evaluated (note: the adsorption efficiency refers to the minimum time used to achieve the target indices, such as the adsorption rate, and the homogeneity etc).

(2) By using the weight ratio of components, the adsorption efficiency and amount of element aluminium could be exactly and scientifically described; for an adsorption rate of 90%-100%, the weight ratio between the antigen and the element aluminium was 1:1.98, far less than presently reported ratio of 1:45, suggesting that the amount of element aluminium could be effectively reduced for adsorbing the same amount of protein, which was beneficial to the health of patients, and met the requirements of WHO and in "Guidelines for Preclinical Research on Preventive Vaccines".

(3) Difficulties and costs could be effectively reduced for multi-antigen component vaccine formulation by using the particular formulation process of the invention.

(4) The homogeneity and stability of the formulation could be guaranteed by using the particular formulation process of the invention.

(5) For the vaccine diluent, various parameters for the histidine buffer system were optimized in the present invention, and preferably, poloxamer 188 was selected as the solubilizing agent, which extended the applicability and reduced the risk of side effect of vaccine diluent.

(6) For the existing formulation modes and equipments, vertical suspension mode and corresponding equipment were originally proposed for the adsorption in the present invention, and an utility model patent was applied for the equipment (issued patent No. 201220314436.4).

Based on the above analysis, the existing formulation process was optimized and improved by a variety of improvements and innovations, which reduced the process steps, decreased the costs and improved the production efficiency. By investigating the component processing step, improving the adsorption mode and changing the composition of the vaccine diluent, the adsorption rate of antigen protein and the weight ratio were improved, which ensured the adsorption homogeneity of each component in the vaccine, and prevented the physicochemical properties of the aluminium adjuvant from changing during formulation, also reduced the amount of element aluminium, improved production efficiency and reduced costs. In this invention, the evaluation indices were improved, and new indices and their detection methods were proposed. Besides, a set of scientific and rigorous evaluation system for formulation was established, filling the gap in this field.

The antigen proteins and various reagents used in this section were listed as follows:

1. Antigen Proteins

Recombinant *Staphylococcus aureus* vaccine antigen proteins were supplied by Chongqing Yuanlun Biotechnology Co., Ltd, and Third Military Medical University of Chinese People's Liberation Army. The antigen proteins included SpA5 (KKAA) of the invention, and HI, mSEB and MntC protein.

2. Reagents

The reagents and equipments, such as SDS-PAGE, and HPLC, etc., were provided by Chongqing Yuanlun Biotechnology Co., Ltd.

The vaccine diluent: 10 mM histidine (Merck corporation, US, pharmaceutical grade), 0.9% NaCl (Sichuan Kelun company, physiological saline for injection) and 0.01% poloxamer 188 (Merck corporation, US, pharmaceutical grade), pH 6.0, pyrogen-free.

PBS: potassium dihydrogen phosphate ($KH_2PO_4$) 0.2 g (domestic reagent of analytical grade), disodium hydrogen phosphate ($Na_2HPO_4.12H_2O$) 2.9 g (domestic reagent of analytical grade), sodium chloride (NaCl) 8.0 g (domestic reagent of analytical grade), and potassium chloride (KCl) 0.2 g, adding water to a final volume of 1000 mL, pH 7.4;

Aluminum phosphate adjuvant (concentration of element aluminium: 5.3 mg/ml) was an imported product with original packaging from GENERAL CHEMICAL corporation, US.

3. Equipments

Large-scale vertically suspending instrument used for vaccine formulation was of independent intellectual property rights, and manufactured by Shanghai Geshi Corporation.

Example 16: Formulation of 4-Component Recombinant *Staphylococcus aureus* Vaccine (1920 mL)

(1) 256 mL aluminum phosphate adjuvant was added to a formulation bottle, to which 704 mL vaccine diluent was added to obtain a final volume of 960 mL. The mixture was fully mixed.

(2) The final concentration of the recombinant *Staphylococcus aureus* vaccine antigen protein was 0.2 mg/ml, and the final concentration of an individual recombinant *Staphylococcus aureus* vaccine antigen protein was 0.05 mg/ml. Accordingly, based on the initial concentration of each antigen protein, the amount of each protein was taken out. The volume required for HI protein was 96 mL, to which 144 mL vaccine diluent was added; the volume required for SpA5 (KKAA) was 48 mL, to which 192 mL vaccine diluent was added; the volume required for mSEB protein was 60 mL, to which 180 mL vaccine diluent was added; and the volume required for MntC protein was 60 mL, to which 180 mL vaccine diluent was added. The mixtures of each protein and corresponding diluent were added to respective formulation bottles, and mixed sufficiently.

(3) Diluted individual antigen protein solutions were each added to the diluted adjuvant solution of the same volume in individual subpackage bottles; the mixture was suspended vertically at 14 rpm for adsorption for 1 h at ambient temperature controlled in the range from 4-37° C.

(4) After adsorption, vaccine formulation was prepared by fully mixing all 4 protein solutions.

Example 17: Formulation of 4-Component Recombinant *Staphylococcus aureus* Vaccine (1200 mL)

(1) 160 mL aluminum phosphate adjuvant was added to a formulation bottle, to which 440 mL vaccine diluent was added to obtain a final volume of 600 mL. The mixture was fully mixed.

(2) The final concentration of the recombinant *Staphylococcus aureus* vaccine antigen protein was 0.2 mg/ml, and the final concentration of an individual recombinant *Staphylococcus aureus* vaccine antigen protein was 0.05 mg/ml. Accordingly, based on the required amount, corresponding protein solutions were taken out. The volume required for HI protein was 60 mL, to which 90 mL vaccine diluent was added; the volume required for SpA5 (KKAA) was 30 mL, to which 120 mL vaccine diluent was added; the volume required for mSEB protein was 37.5 mL, to which 112.5 mL vaccine diluent was added; and the volume required for MntC protein was 37.5 mL, to which 112.5 mL vaccine diluent was added. The mixtures of each protein and corresponding diluent were added to respective formulation bottles, and mixed sufficiently.

(3) Diluted individual antigen protein solutions were each added to the diluted adjuvant solution of the same volume in individual subpackage bottles. Subsequently, 4 antigen solutions were mixed, and vertically suspended at 14 rpm for adsorption for 1 h at ambient temperature controlled in the range from 4-37° C.

Example 18: Formulation of 4-Component Recombinant *Staphylococcus aureus* Vaccine (600 mL)

(1) 80 mL aluminum phosphate adjuvant required was added to a formulation bottle, to which 220 mL vaccine diluent was added to a final volume of 300 mL. The mixture was fully mixed.

(2) The final concentration of the recombinant *Staphylococcus aureus* vaccine antigen protein was 0.2 mg/ml, and the final concentration of an individual recombinant *Staphylococcus aureus* vaccine antigen protein was 0.05 mg/ml. Accordingly, based on the initial concentration of each protein, the amount of each protein required was calculated. The volume required was 30 mL for HI protein, 15 mL for SpA5 (KKAA), 18.75 mL for mSEB protein, and 18.75 mL for MntC protein. All 4 proteins were added to a formulation bottle, to which 217.5 mL vaccine diluent was added to a final volume of 300 mL. The mixture was mixed sufficiently.

(3) The diluted antigen protein solution and the diluted adjuvant solution of the same volume were added to a subpackage bottle. The mixture was suspended vertically at 14 rpm for adsorption for 1 h at ambient temperature controlled in the range from 4-37° C.

Example 19: Adsorption Homogeneity and Completeness of the Antigen Proteins in the Recombinant *Staphylococcus aureus* Vaccine by the Aluminum Phosphate Adjuvant Characterized by SDS-PAGE (1) 1 mL sample was each collected from the vaccine formulations of Example 16-18, and centrifugated at 6000 rpm for 5 min at 4° C. The supernatant was carefully withdrawn, from which 40 µl sample was collected.

(2) The dissociation solution (1 M $Na_2CO_3$) of the same volume as the supernatant was added to the precipitate. The precipitate was re-suspended, and vertically suspended at room temperature for 1 h. 40 µl sample was collected.

(3) According to the formulation method of Example 18, a protein solution free of the aluminum phosphate adjuvant was prepared, in which the volume for aluminum phosphate was supplemented by the vaccine diluent. After fully mixed, 40 µl sample was collected;

(4) To the sample collected, 10 µl 5× loading buffer was added. The mixture was heated at 100° C. for 5 min. After cooling down, the samples were centrifugated instantly, and 10 µl samples were loaded to the gel.

Figure 43:
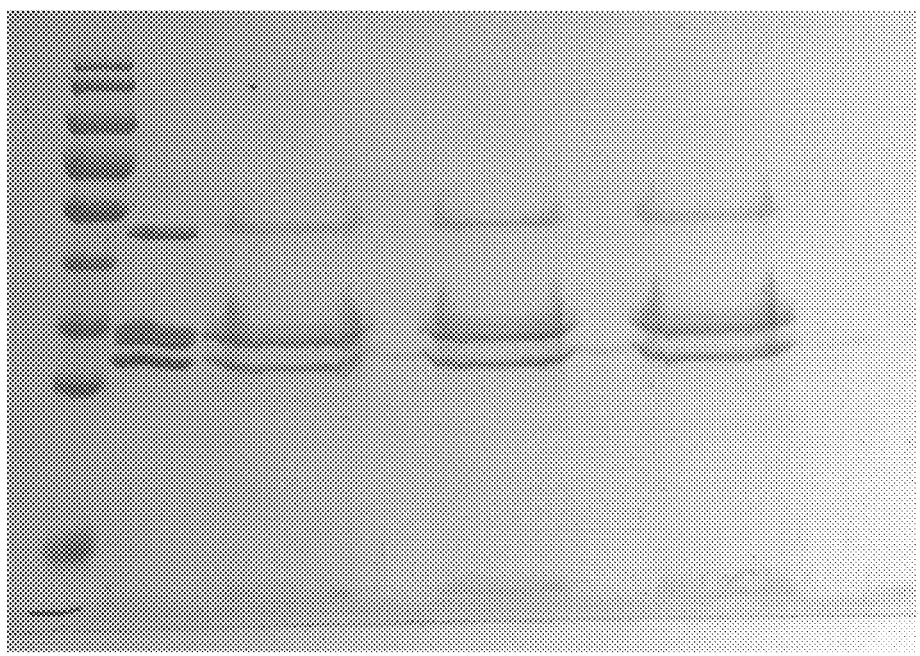
FIG. 43 shows SDS-PAGE analysis of the samples of Example 19; Lane M: protein molecular weight markers; Lane 1: protein solution (free of aluminum phosphate adjuvant) formulated of the same concentration in Example 19; Lane 2: the sample obtained from the semi-finished product in Example 16 after centrifugation and dissociation; Lane 3: the sample obtained from the supernatant of the semi-finished product in Example 16 after centrifugation; Lane 4: the sample obtained from the semi-finished product in Example 17 after centrifugation and dissociation; Lane 5: the sample obtained from the supernatant of the semi-finished product in Example 17 after centrifugation; Lane 6: the sample obtained from the semi-finished product in Example 18 after centrifugation and dissociation; and Lane 7: the sample obtained from the supernatant of the semi-finished product in Example 18 after centrifugation.

(5) The procedure for 12% SDS-PAGE included initially running at 80 v for 20 min, and then at 180 v for 40 min. After running, the gel was stained in Coomassie staining solution under shaking, followed by destained in destaining solution under shaking. The gel was observed in an imaging system. The results were shown in FIG. 43, which indicated that the proteins could be fully adsorbed by the aluminum phosphate adjuvant in all 3 methods, and no significant difference was observed for adsorption. However, both methods 2 and 3 were simpler than method 1. If method 1 was employed to prepare a multi-antigen vaccine, the equipments for adsorption and mixing were required for each antigen, and could not be shared, so that the total number of equipments used was much more than that for both methods 2 and 3.

Example 20: Studies on the Weight Ratio Between the Components of the Recombinant *Staphylococcus aureus* Vaccine (1) 720 µl aluminum phosphate adjuvant solution (concentration of element aluminium: 5.3 mg/ml) was added to a formulation bottle, into which 6.48 mL vaccine diluent was added and fully mixed. The mixture was divided into 12 aliquots (600 µl for each aliquot, containing 60 µl aluminum phosphate and 318 µg element aluminium).

(2) Based on dose escalation of each antigen used, 3 groups, including 80 µg dose group, 120 µg dose group, and 160 µg dose group, were divided for each antigen, and there were totally 12 groups for all 4 antigens. The volume required for each protein was calculated according to its concentration, taken out and added to corresponding bottles, to which the vaccine diluent was added to a final volume of 600 µl.

(3) The diluted individual antigen protein solutions were each added to the diluted adjuvant solution of the same volume in individual subpackage bottles. The mixture was suspended vertically at 14 rpm for adsorption for 1 h at ambient temperature controlled in the range from 4-37° C.

Example 21: The Weight Ratio Between the Components of the Recombinant *Staphylococcus aureus* Vaccine Characterized by SDS-PAGE (1) 12 samples from Example 20 were centrifugated at 6000 rpm for 5 min at 4° C. The supernatant was carefully withdrawn, from which 40 µl sample was collected.

(2) According to the formulation method of Example 20, a protein solution free of the aluminum phosphate adjuvant was prepared, in which the volume for aluminum phosphate was supplemented by the vaccine diluent. After fully mixed, 40 µl sample was collected.

(3) To the sample collected, 10 µl 5× loading buffer was added. The mixture was heated at 100° C. for 5 min. After cooling down, the samples were centrifugated instantly, and 10 µl samples were loaded to the gel.

Figure 44:
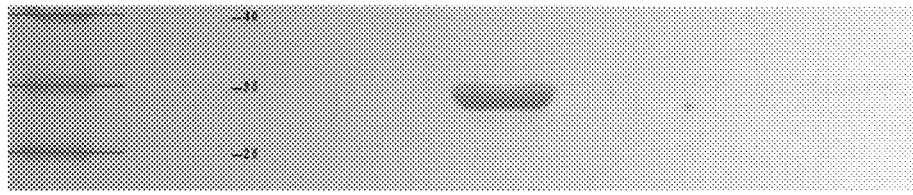
FIG. 44 shows SDS-PAGE analysis of the samples of Example 21; Lane M: protein molecular weight markers; Lane 1: 80 μg HI protein sample; Lane 2: 120 μg HI protein sample; Lane 3: 160 μg HI protein sample; Lane 4: SpA5 (KKAA) free of adjuvant; Lane 5: 80 μg SpA5 (KKAA); Lane 6: 120 μg SpA5 (KKAA); and Lane 7: 160 μg SpA5 (KKAA).
Figure 45:
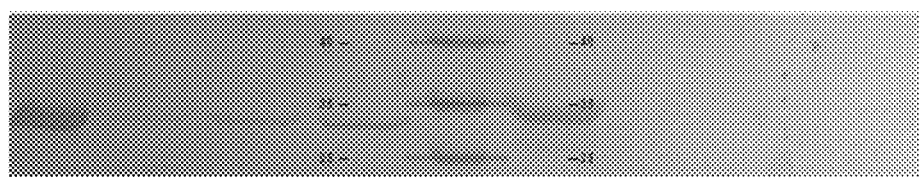
FIG. 45 shows SDS-PAGE analysis of the samples of Example 21; Lane M: protein molecular weight markers; Lane 1: mSEB protein free of adjuvant; Lane 2: 80 μg mSEB protein; Lane 3: 80 μg mSEB protein; Lane 4: 160 μg mSEB protein; Lane 5: MntC protein free of adjuvant; Lane 6: 80 μg MntC protein; Lane 7: 120 μg MntC protein; and Lane 8: 160 μg MntC protein.

(4) The procedure for 12% SD S-PAGE included initially running at 80 v for 20 min, and then at 180 v for 40 min. After running, the gel was stained in Coomassie staining solution under shaking, followed by destained in destaining solution under shaking. The gel was observed in an imaging system. The results were shown in FIGS. 44 and 45, which indicated that for HI, SpA5 (KKAA) and MntC, 100% adsorption of 160 µg protein could be achieved by 318 µg element aluminium, i.e., the weight ratio between the protein and element aluminium was 1:1.9875 for 100% adsorption; while for mSEB, 100% adsorption of 80 µg protein and 90% adsorption of 160 µg protein could be achieved by 318 µg element aluminium, i.e., the weight ratio between the protein and element aluminium was 1:3.975 for 100% adsorption, and 1:1.9875 for 90% adsorption. Accordingly, it was believed that for the recombinant *Staphylococcus aureus* vaccine antigen protein, 90-100% adsorption could be achieved at the weight ratio of 1:1.9875 between the protein and element aluminium.

Meanwhile, it should also be pointed out that if only the volume was described while the weight was neglected, i.e., the ratio was not defined, the ratio between the protein and element aluminium would be much lower, even lower than 1:1.

Example 22: Homogeneity of the Recombinant *Staphylococcus aureus* Vaccine Characterized by SDS-PAGE (1) 6 samples were randomly collected from the solution in Example 18 after complete adsorption and mixing well. The sampling location and time were completely random. For each sample, 1 mL was collected.

(2) The sample was centrifugated at 6000 rpm for 5 min at 4° C. The supernatant was carefully withdrawn, from which 40 µl sample was collected.

(3) The dissociation solution of the same volume as the supernatant was added to the precipitate. The precipitate was re-suspended, and vertically suspended at room temperature for 1 h. 40 µl sample was collected.

(4) To the sample collected, 10 µl 5× loading buffer was added. The mixture was heated at 100° C. for 5 min. After cooling down, the samples were centrifugated instantly, and 10 µl samples were loaded to the gel.

Figure 46:
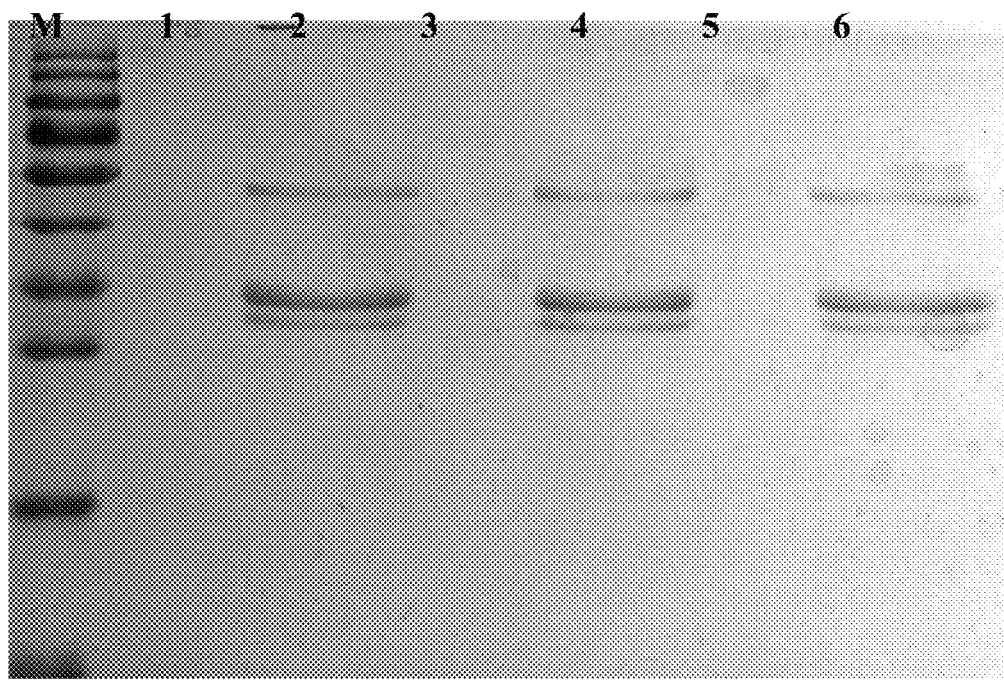
FIG. 46 shows SDS-PAGE analysis of the samples of Example 22; Lane M: protein molecular weight markers; Lane 1: randomly collected sample 1—the supernatant after centrifugation; Lane 2: randomly collected sample 1—dissociated precipitate after centrifugation; Lane 3: randomly collected sample 2—the supernatant after centrifugation; Lane 4: randomly collected sample 2—dissociated precipitate after centrifugation; Lane 5: randomly collected sample 3—the supernatant after centrifugation; and Lane 6: randomly collected sample 3—dissociated precipitate after centrifugation.
Figure 47:
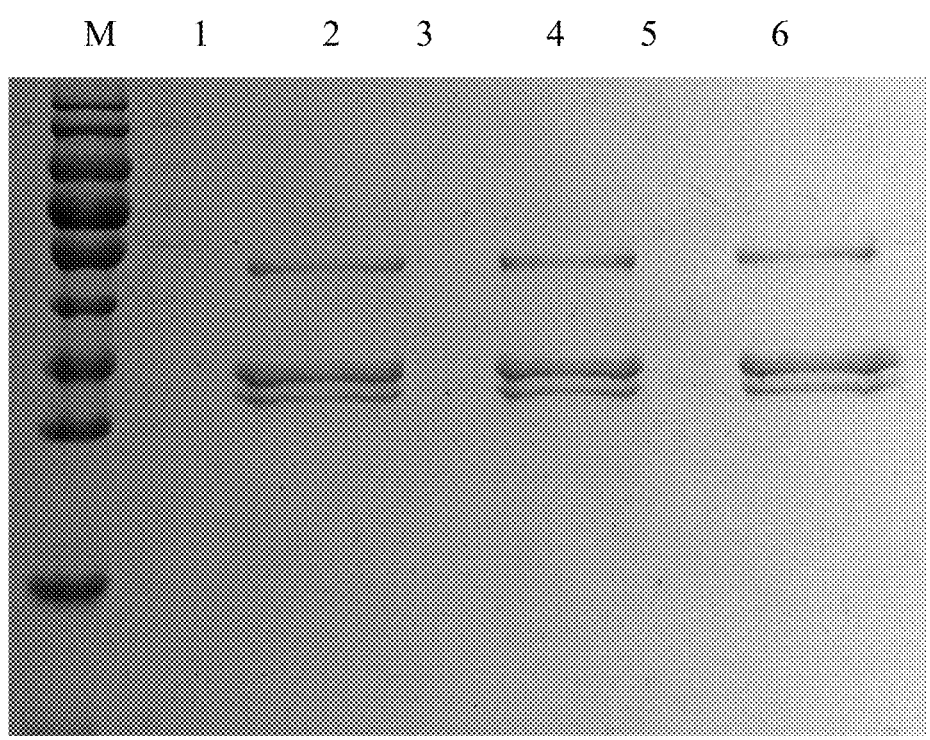
FIG. 47 shows SDS-PAGE analysis of the samples of Example 22; Lane M: protein molecular weight markers; Lane 1: randomly collected sample 4—the supernatant after centrifugation; Lane 2: randomly collected sample 4—dissociated precipitate after centrifugation; Lane 3: randomly collected sample 5—the supernatant after centrifugation; Lane 4: randomly collected sample 5—dissociated precipitate after centrifugation; Lane 5: randomly collected sample 6—the supernatant after centrifugation; and Lane 6: randomly collected sample 6—dissociated precipitate after centrifugation.

(5) The procedure for 12% SDS-PAGE included initially running at 80 v for 20 min, and then at 180 v for 40 min. After running, the gel was stained in Coomassie staining solution under shaking, followed by destained in destaining solution under shaking. The gel was observed in an imaging system. The results were shown in FIGS. 46 and 47, which indicated that no band was seen for the supernatant of the sample after centrifugation, whereas the positions, grayscale values and areas of the bands were all identical for the precipitate after dissociation, suggesting that the amounts and types of antigen proteins adsorbed by the adjuvant at each random sampling point were totally the same, i.e., the homogeneity was obtained for the adsorption in formulation process.

Example 23: Adsorption Rate and Efficiency for the Recombinant *Staphylococcus aureus* Vaccine Antigen Protein Formulation (1) 1.2 mL aluminum phosphate adjuvant solution (concentration of element aluminium: 5.3 mg/ml) was added to a formulation bottle, into which 10.8 mL vaccine diluent was added and fully mixed. The mixture was divided into 20 aliquots (600 µl for each aliquot, containing 60 µl aluminum phosphate and 318 µg element aluminium).

(2) There were 20 groups divided, including 0.5 h, 1 h, 2 h, 4 h, and 8 h group for each antigen, based on the doubled adsorption durations for each antigen protein. According to the concentrations, the required volumes were calculated for each protein, and added to corresponding bottles, into which the vaccine diluent was added to a final volume of 600 µl.

(3) The diluted individual antigen protein solutions were each added to the diluted adjuvant solution of the same volume in individual subpackage bottles. The mixture was suspended vertically at 14 rpm for adsorption for a specified duration. The samples were treated after adsorption at ambient temperature controlled in the range from 4-37° C.

Example 24: Adsorption Rate and Efficiency for the Recombinant *Staphylococcus aureus* Vaccine Formulation Characterized by SDS-PAG (1) 20 samples of Example 23 were centrifugated at 6000 rpm for 5 min at 4° C. The supernatant was carefully withdrawn, from which 40 µl sample was collected.

(2) To the sample collected, 10 µl 5× loading buffer was added. The mixture was heated at 100° C. for 5 min. After cooling down, the samples were centrifugated instantly, and 10 µl samples were loaded to the gel.

Figure 48:
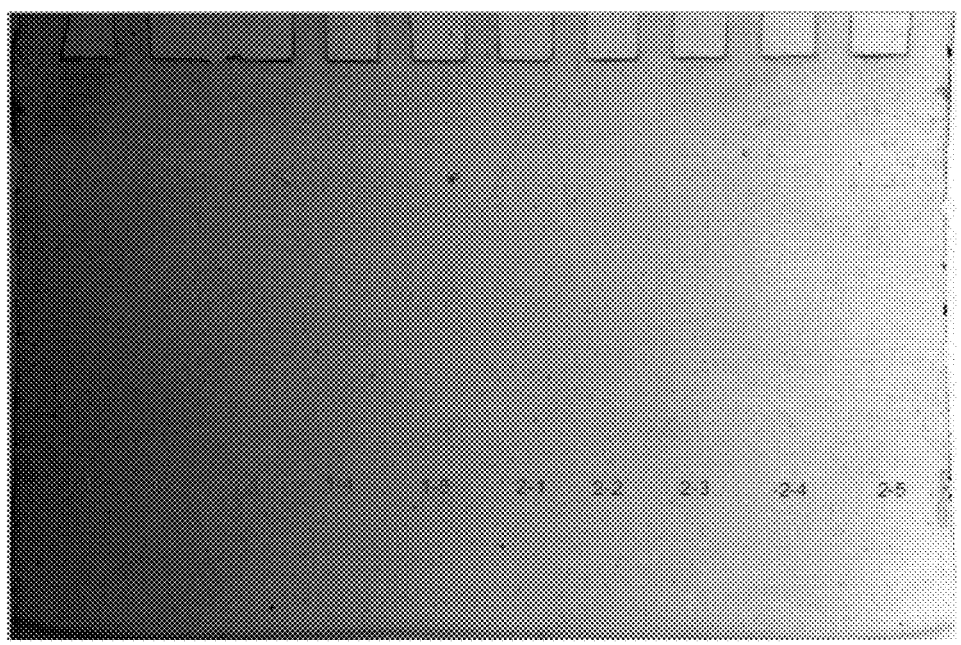
FIG. 48 shows SDS-PAGE analysis of the samples of Example 24; Lane 1: the supernatant obtained by centrifugation after 0.5 h adsorption of HI protein; Lane 2: the supernatant obtained by centrifugation after 1 h adsorption of HI protein; Lane 3: the supernatant obtained by centrifugation after 2 h adsorption of HI protein; Lane 4: the supernatant obtained by centrifugation after 4 h adsorption of HI protein; Lane 5: the supernatant obtained by centrifugation after 8 h adsorption of HI protein; Lane 6: supernatant obtained by centrifugation after 0.5 h adsorption of SpA5 (KKAA); Lane 7: the supernatant obtained by centrifugation after 1 h adsorption of SpA5 (KKAA); Lane 8: the supernatant obtained by centrifugation after 2 h adsorption of SpA5 (KKAA); Lane 9: the supernatant obtained by centrifugation after 4 h adsorption of SpA5 (KKAA); and Lane 10: the supernatant obtained by centrifugation after 8 h adsorption of SpA5 (KKAA).
Figure 49:
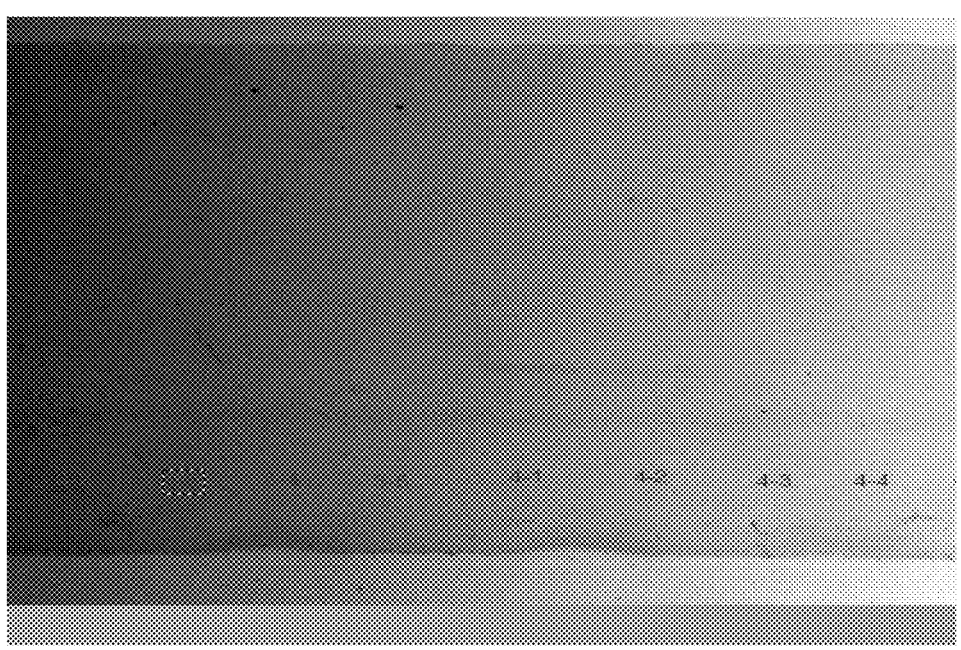
FIG. 49 shows SDS-PAGE analysis of the samples of Example 24; Lane 1: the supernatant obtained by centrifugation after 1 h adsorption of MntC protein; Lane 2: the supernatant obtained by centrifugation after 2 h adsorption of MntC protein; Lane 3: the supernatant obtained by centrifugation after 4 h adsorption of MntC protein; Lane 4: the supernatant obtained by centrifugation after 8 h adsorption of MntC protein; Lane 5: the supernatant obtained by centrifugation after 1 h adsorption of mSEB protein; Lane 6: the supernatant obtained by centrifugation after 2 h adsorption of mSEB protein; Lane 7: the supernatant obtained by centrifugation after 4 h adsorption of mSEB protein; and Lane 8: the supernatant obtained by centrifugation after 8 h adsorption of mSEB protein.

(3) The procedure for 12% SDS-PAGE included initially running at 80 v for 20 min, and then at 180 v for 40 min. After running, the gel was stained in Coomassie staining solution under shaking, followed by destained in destaining solution under shaking. The gel was observed in an imaging system. The results were shown in FIGS. 48 and 49, which indicated that for the recombinant *Staphylococcus aureus* vaccine antigen protein, 100% adsorption could be achieved within 2 h, and more than 90% adsorption within 1 h, i.e., 90-100% adsorption of the recombinant *Staphylococcus aureus* vaccine antigen protein could be achieved within 1 h.

Example 25: Stability of the Recombinant *Staphylococcus aureus* Vaccine Characterized by SDS-PAGE (1) The solution of Example 18 after adsorption and mixing well was divided into 1 mL aliquots, and then encapsulated into 2 mL aseptic penicillin vials. The vial was subsequently sealed by a cap and stored at 37° C.

(2) 3 vials were randomly taken out every 4 weeks. The samples were centrifugated at 6000 rpm for 5 min at 4° C. The supernatant was carefully withdrawn, from which 40 µl sample was collected.

(3) The dissociation solution of the same volume as the supernatant was added to the precipitate. The precipitate was re-suspended, and vertically suspended at room temperature for 1 h. 40 µl sample was collected.

(4) To the sample collected, 10 µl 5× loading buffer was added. The mixture was heated at 100° C. for 5 min. After cooling down, the samples were centrifugated instantly, and 10 µl samples were loaded to the gel.

Figure 50:
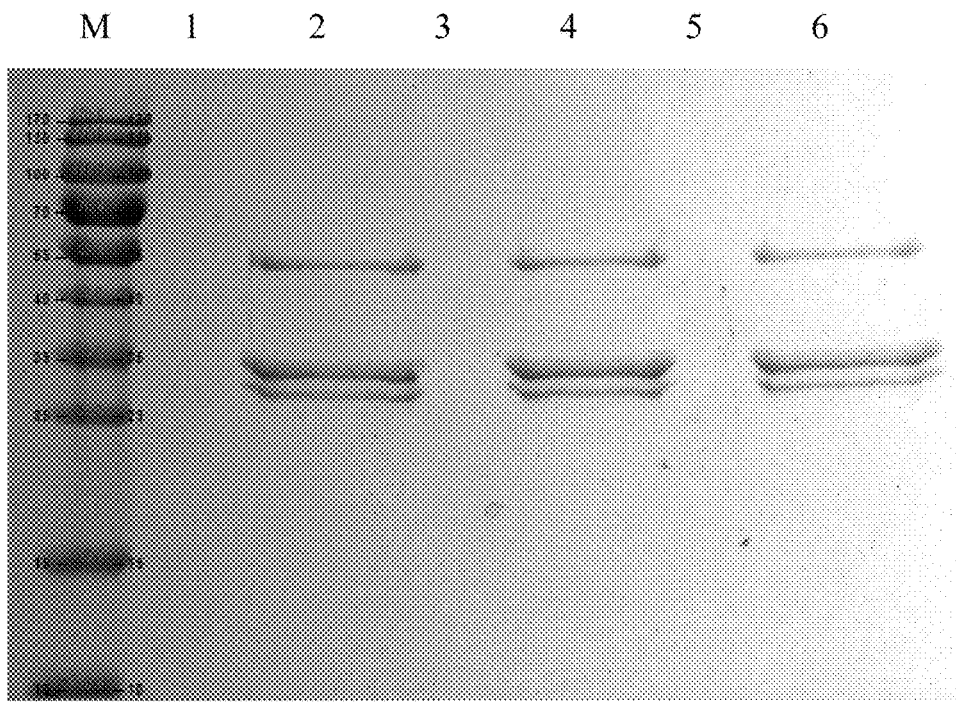
FIG. 50 shows SDS-PAGE analysis of the samples in Example 25 stored for 4 weeks; Lane M: protein molecular weight markers; Lane 1: randomly collected sample 1—the supernatant after centrifugation; Lane 2: randomly collected sample 1—dissociated precipitate after centrifugation; Lane 3: randomly collected sample 2—the supernatant after centrifugation; Lane 4: randomly collected sample 2—dissociated precipitate after centrifugation; Lane 5: randomly collected sample 3—the supernatant after centrifugation; and Lane 6: randomly collected sample 3—dissociated precipitate after centrifugation.
Figure 51:
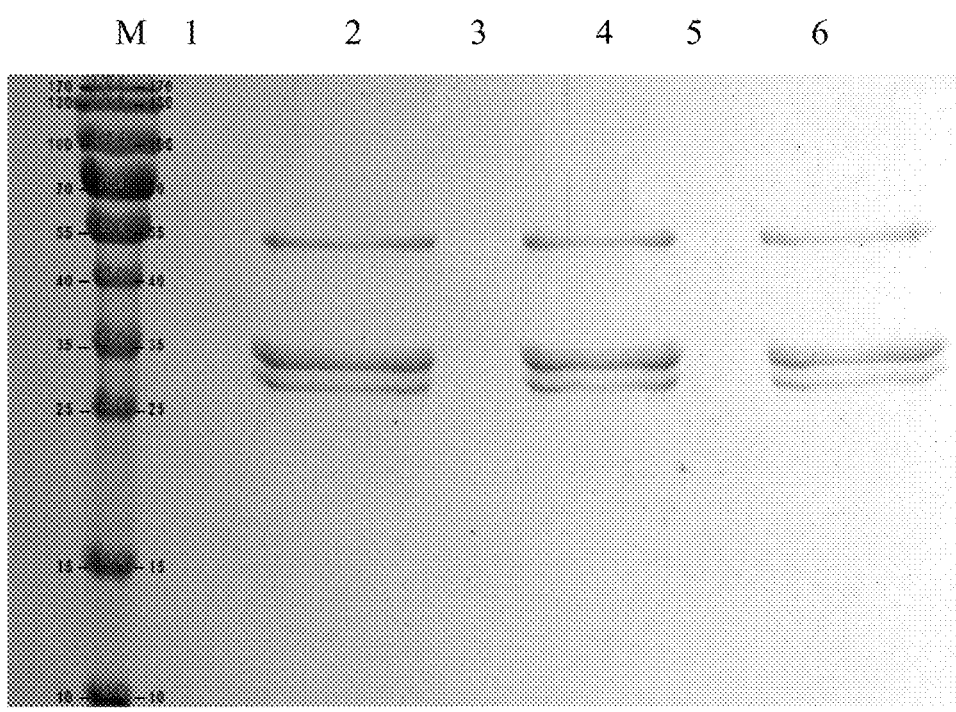
FIG. 51 shows SDS-PAGE analysis of the samples in Example 25 stored for 8 weeks; Lane M: protein molecular weight markers; Lane 1: randomly collected sample 1—the supernatant after centrifugation; Lane 2: randomly collected sample 1—dissociated precipitate after centrifugation; Lane 3: randomly collected sample 2—the supernatant after centrifugation; Lane 4: randomly collected sample 2—dissociated precipitate after centrifugation; Lane 5: randomly collected sample 3—the supernatant after centrifugation; and Lane 6: randomly collected sample 3—dissociated precipitate after centrifugation.
Figure 52:
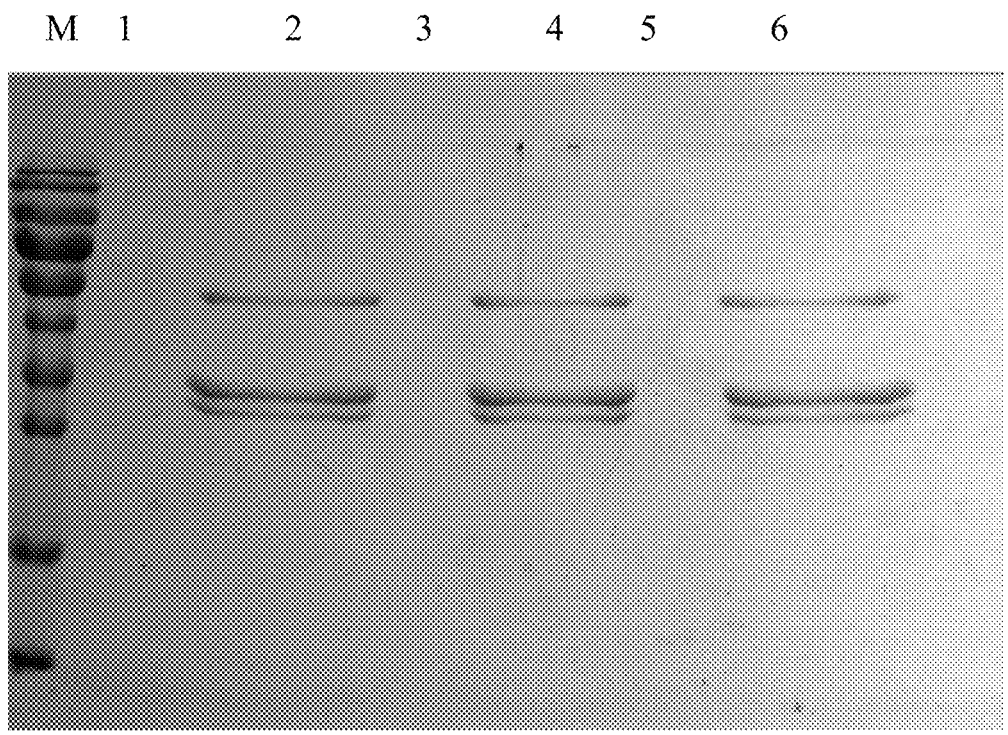
FIG. 52 shows SDS-PAGE analysis of the samples in Example 25 stored for 12 weeks; Lane M: protein molecular weight markers; Lane 1: randomly collected sample 1—the supernatant after centrifugation; Lane 2: randomly collected sample 1—dissociated precipitate after centrifugation; Lane 3: randomly collected sample 2—the supernatant after centrifugation; Lane 4: randomly collected sample 2—dissociated precipitate after centrifugation; Lane 5: randomly collected sample 3—the supernatant after centrifugation; and Lane 6: randomly collected sample 3—dissociated precipitate after centrifugation.

(5) The procedure for 12% SDS-PAGE included initially running at 80 v for 20 min, and then at 180 v for 40 min. After running, the gel was stained in Coomassie staining solution under shaking, followed by destained in destaining solution under shaking. The gel was observed in an imaging system. The results were shown in FIGS. 50, 51 and 52, which indicated that no band was seen for the supernatant of the sample after centrifugation, whereas the positions, grayscale values and areas of the bands were all identical for the precipitate after dissociation, suggesting that the amounts and types of antigen proteins adsorbed by the adjuvant at each random sampling point were totally the same. The results further confirmed the homogeneity of the formulation. Besides, it also demonstrated the stability of the formulation, including the stability of the adsorption rate, the homogeneity and the antigen protein.

As demonstrated by the results, the formulation of the invention was stable for at least 12 weeks under accelerated temperature condition (37° C.), which further confirmed the effectiveness and stability of the formulation process.

Example 26: Immunization Potency and Protection Effect Against Challenging for the Vaccines of Various Components Multi-component vaccines were prepared using SpA5 (KKAA) as the antigen candidate, in monovalent, bivalent, trivalent and tetravalent combination with HI, MntC, and mSEB. The antibody titer was evaluated after further immunization of mice. ELISA was performed for the serum, and the results were listed in Table 10.

Protection against challenging was tested (the processes for immunization and protection against challenging were as described in Example 12). 6 rounds of experiments were carried out from V34 to V39, in which there were 20 Balb/C mice (6-week old, Beijing HFK Bioscience Co., Ltd.) in each group. Immunization was performed by intramuscular injection, with a protein content of 30 µg for each component. The procedure of challenging test was as follows: immunization was performed by quadriceps femoris injection (Day 0, 14 and 21) of each vaccine for 3 times; after the last immunization, viable *Staphylococcus aureus* MRSA-252 was injected via caudal vein at a fatal dose on Day 14 for the challenging test. The amount of bacteria suspension was $1.25 \times 10^9$ CFU for each BALB/C mouse. After observed for 10 days, the survival rate was calculated for each group. The results were listed in table 11.

TABLE 10

The antibody titers in the mice after immunization by various proteins and their combinations as detected by ELISA

| | Groups | | Antibody titer × $10^5$ | | | | | | |
| --- | --- | --- | --- | --- | --- | --- | --- | --- | --- |
| | | | V34 | V35 | V36 | V37 | V38 | V39 | Average |
| Control | Vaccine diluent | | 0.001 | 0.001 | 0.001 | 0.001 | 0.001 | 0.001 | 0.001 |
| | AlPO₄ | | 0.001 | 0.001 | 0.001 | 0.001 | 0.001 | 0.001 | 0.001 |
| Monovalent | HI | | 1.28 | 1.28 | 1.11 | 1.28 | 1.19 | 1.28 | 1.24 |
| | mSEB | | 1.11 | 1.28 | 1.04 | 1.19 | 1.04 | 1.11 | 1.13 |
| | SpA5 | | 0.84 | 0.79 | 0.74 | 0.84 | 0.69 | 0.79 | 0.78 |
| | MntC | | 1.28 | 1.28 | 1.28 | 1.28 | 1.28 | 1.28 | 1.28 |
| Bivalent | HI + mSEB | HI | 1.11 | 1.04 | 0.97 | 0.91 | 0.97 | 1.19 | 1.03 |
| | | mSEB | 1.19 | 1.11 | 1.04 | 1.19 | 0.97 | 1.04 | 1.09 |
| | HI + SpA5 | HI | 1.11 | 1.04 | 1.11 | 0.91 | 0.97 | 1.11 | 1.04 |
| | | SpA5 | 0.49 | 0.45 | 0.52 | 0.49 | 0.60 | 0.56 | 0.52 |
| | HI + MntC | HI | 1.11 | 1.19 | 1.11 | 0.92 | 1.04 | 0.97 | 1.06 |
| | | MntC | 1.28 | 1.28 | 1.28 | 1.28 | 1.28 | 1.28 | 1.28 |
| | mSEB + SpA5 | mSEB | 0.91 | 1.19 | 1.04 | 0.97 | 1.19 | 1.11 | 1.07 |
| | | SpA5 | 0.52 | 0.56 | 0.64 | 0.52 | 0.60 | 0.56 | 0.57 |
| | mSEB + MntC | mSEB | 1.19 | 1.10 | 1.02 | 0.94 | 1.10 | 1.02 | 1.06 |
| | | MntC | 1.28 | 1.28 | 1.28 | 1.28 | 1.28 | 1.28 | 1.28 |
| | SpA5 + MntC | SpA5 | 0.49 | 0.52 | 0.56 | 0.49 | 0.64 | 0.60 | 0.55 |
| | | MntC | 1.28 | 1.28 | 1.28 | 1.28 | 1.28 | 1.28 | 1.28 |
| Trivalent | HI + mSEB + SpA5 | HI | 0.97 | 1.11 | 0.91 | 1.04 | 1.19 | 0.97 | 1.03 |
| | | mSEB | 1.04 | 0.97 | 1.04 | 0.91 | 0.84 | 1.04 | 0.97 |
| | | SpA5 | 0.55 | 0.56 | 0.52 | 0.52 | 0.49 | 0.52 | 0.53 |
| | HI + mSEB + MntC | HI | 1.11 | 0.91 | 0.91 | 1.11 | 0.97 | 1.04 | 1.01 |
| | | mSEB | 0.85 | 0.8 | 0.91 | 0.74 | 0.69 | 0.74 | 0.79 |
| | | MntC | 1.28 | 1.28 | 1.28 | 1.28 | 1.28 | 1.28 | 1.28 |
| | HI + SpA5 + MntC | HI | 0.69 | 0.79 | 0.64 | 0.69 | 0.60 | 0.74 | 0.69 |
| | | SpA5 | 0.24 | 0.26 | 0.30 | 0.26 | 0.28 | 0.24 | 0.26 |
| | | MntC | 1.28 | 1.28 | 1.28 | 1.28 | 1.28 | 1.28 | 1.28 |

TABLE 10-continued

The antibody titers in the mice after immunization by various proteins and their combinations as detected by ELISA

| Groups | | | Antibody titer × 10⁵ | | | | | | |
|---|---|---|---|---|---|---|---|---|---|
| | | | V34 | V35 | V36 | V37 | V38 | V39 | Average |
| Tetravalent | mSEB + SpA5 + MntC | mSEB | 0.91 | 0.84 | 0.79 | 1.04 | 0.84 | 0.79 | 0.87 |
| | | SpA5 | 0.24 | 0.23 | 0.24 | 0.20 | 0.21 | 0.23 | 0.23 |
| | | MntC | 1.28 | 1.28 | 1.28 | 1.28 | 1.28 | 1.28 | 1.28 |
| | HI + SpA5 + mSEB + MntC | HI | 0.79 | 0.74 | 0.79 | 0.84 | 0.79 | 0.69 | 0.77 |
| | | Spa5 | 0.23 | 0.20 | 0.23 | 0.21 | 0.21 | 0.20 | 0.21 |
| | | mSEB | 0.37 | 0.34 | 0.37 | 0.34 | 0.37 | 0.32 | 0.35 |
| | | MntC | 1.28 | 1.28 | 1.28 | 1.28 | 1.28 | 1.28 | 1.28 |

TABLE 11

Evaluation on the protection effects against challenging in the mice after immunization by various vaccines

| | Groups | Survival rate (%) | | | | | | |
|---|---|---|---|---|---|---|---|---|
| | | V34 | V35 | V36 | V37 | V38 | V39 | Average |
| Control | Vaccine diluent | 0% | 10% | 10% | 20% | 10% | 30% | 13.3% |
| | AlPO₄ | 30% | 40% | 50% | 30% | 30% | 30% | 35% |
| Monovalent | HI | 30% | 30% | 40% | 30% | 30% | 30% | 31.7% |
| | mSEB | 30% | 11.1% | 30% | 30% | 30% | 30% | 26.9% |
| | SpA5 | 70% | 20% | 30% | 30% | 40% | 30% | 36.7% |
| | MntC | 60% | 10% | 30% | 30% | 40% | 30% | 33.3% |
| Bivalence | HI + mSEB | 50% | 37.5% | 30% | 60% | 80% | 90% | 57.9% |
| | HI + SpA5 | 50% | 40% | 50% | 60% | 80% | 80% | 60% |
| | HI + MntC | 60% | 50% | 25% | 80% | 90% | 100% | 67.5% |
| | mSEB + SpA5 | 70% | 90% | 60% | 80% | 100% | 60% | 76.7% |
| | mSEB + MntC | 70% | 70% | 70% | 70% | 100% | 90% | 78.3% |
| | SpA5 + MntC | 70% | 70% | 80% | 70% | 60% | 90% | 73.3% |
| Trivalent | HI + mSEB + SpA5 | 70% | 100% | 77.8% | 70% | 80% | 80% | 79.6% |
| | HI + mSEB + MntC | 70% | 60% | 50% | 80% | 70% | 100% | 71.7% |
| | HI + SpA5 + MntC | 70% | 80% | 88.9% | 70% | 60% | 60% | 71.5% |
| | mSEB + SpA5 + MntC | 80% | 70% | 90% | 80% | 70% | 90% | 80% |
| Tetravalent | HI + SpA5 + mSEB + MntC | 90% | 80% | 90% | 90% | 90% | 90% | 88.3% |

It was indicated by the results that the best protection effect was observed for SpA5 (KKAA) in the monovalent groups; and in the bivalent groups, the survival rates were greatly enhanced in the groups containing SpA5; while in the trivalent groups containing SpA5 (mSEB+SpA5+MntC), the protection effect was further enhanced; and the immunoprotective effect on the challenged animals of the tetravalent group containing SpA5 was the best among all groups.

Example 27: Optimization of the Animal Immunization Procedure

In order to make the recombinant *Staphylococcus aureus* vaccine more suitable for clinical practice, the immunization procedure was optimized for the finally determined vaccine components HI+MntC+mSEB+SpA5 (30 μg for each component) as listed in the table below.

The animals were used as described in Example 12. For each vaccine, the groups for the immunization procedure were divided into the diluted vaccine protein groups and the experiment groups, with 30 animals in each group. The immunization procedure was listed in Table 12.

TABLE 12

Immunization procedure

| | Times for immunization | | |
|---|---|---|---|
| | 3 | 2 | 1 |
| Immunization procedure (Day) | 0, 3, 7 | 0, 7<br>0, 3 | 0 |

Protection effect against challenging was listed in Table 13.

TABLE 13

Protection effect against challenging on animals using various immunization procedures

| Immunization | Number of survival animals after 10 days | | Survival rate | |
|---|---|---|---|---|
| procedure | Vaccine diluent | Vaccine | Vaccine diluent | Vaccine |
| 0, 3, 7 | 0 | 29 | 0 | 97% |
| 0, 7 | 0 | 27 | 0 | 90% |
| 0, 3 | 0 | 26 | 0 | 87% |
| 0 | 0 | 21 | 0 | 70% |

As indicated by the results, the best protection effect on the animals after challenging was obtained by the immunization procedure on Day 0, 3 and 7, which was also suitable for clinical application. By this experiment, the effectiveness of the 4-component recombinant *Staphylococcus aureus* vaccine was further confirmed.

Example 28: Acute Toxicity Test on Mice

The test was performed by JOINN Laboratories (Suzhou), Inc., similarly hereinafter.
1) Test Samples, Adjuvant Control and Negative Control
(1) Test Samples
Name: recombinant *Staphylococcus aureus* vaccine
Concentration/content: total content of antigens: 120 μg/0.6 mL, containing 30 μg/0.6 mL HI; 30 μg/0.6 mL SpA5; 30 μg/0.6 mL MntC; and 30 μg/0.6 mL mSEB.
(2) Adjuvant Control
Name: adjuvant control for the recombinant *Staphylococcus aureus* vaccine
Supplier: Chongqing Yuanlun Biotechnology Co., Ltd.
Lot Number: 20130516
Content of aluminium: 0.72 mg/ml.
(3) Negative Control Name: Sodium Chloride Injection
Manufacturer: Jiangsu Yabang Shengyuan Pharmaceutical Co., Ltd.
Lot Number: 12120104.
2) Experiment Animals: ICR Mice (SPF Grade, JOINN Laboratories (Suzhou), Inc.)
Number: 40 mice (20 mice in each group, with half male and half female mice)
Administration frequency: single administration
Route of administration: intramuscular injection
Dosage: 10 mL/kg

TABLE 14

Group division and administration scheme for the acute toxicity test

| Groups | | Dosage a (dose/mouse) | Volume b (mL/mouse) | Number of the animal | |
|---|---|---|---|---|---|
| | | | | Male | Female |
| 1 | Negative control group | 0 | 0.6 | 10 | 10 |
| 2 | Test sample group | 1 | 0.6 | 10 | 10 |

Note:
the total content of antigen administered in the test sample groups was 6000 μg/kg, which was 3000 folds of the intended dosage for clinical practice.

Figure 53:
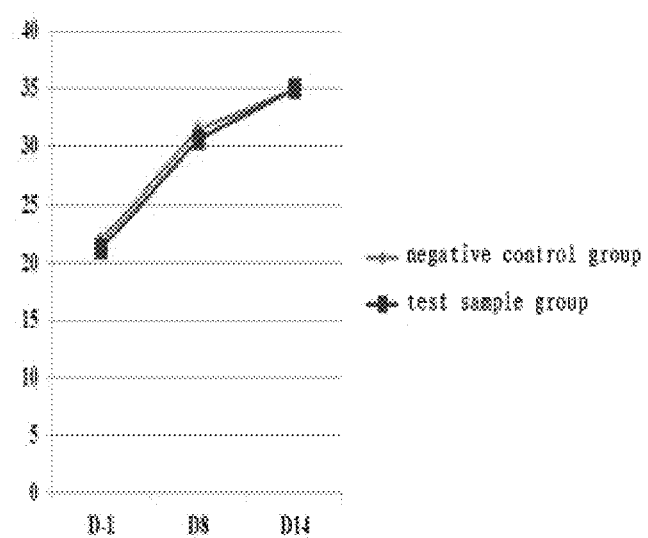
FIG. 53 illustrates the change of body weight of the male animals in each group at various time points.
Figure 54:
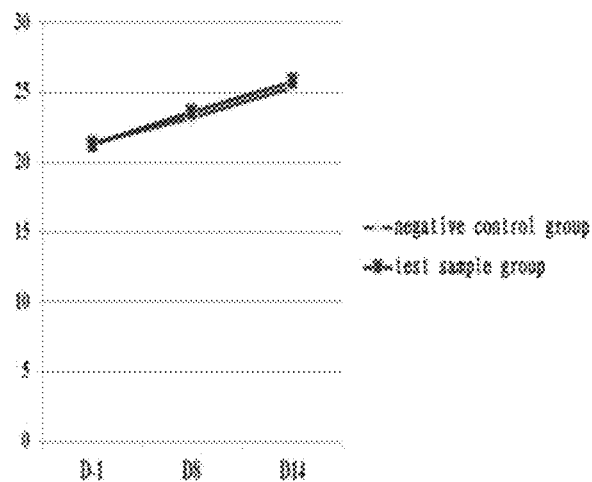
FIG. 54 illustrates the change of body weight of the female animals in each group at various time points.

3) Test Results
During test, no dead or dying animal was observed in each group. No abnormal reaction was observed in clinical in the animals of each group. As compared with the animals of the same gender at the same time in the negative control group, no administration-related toxicologically regular change was observed for the body weight and the food intake in the animals in each group. The results were shown in FIGS. 53 and 54.
Pathological examination: after euthanasia, no significant administration-related abnormal change was observed for all animals during general observation; gross anatomy was performed to all animals, in which swelling was seen in the uterus (bilateral) of only 2 female mice in the negative control group, which was just normal physiologically periodic change.

Example 29: Systemic Active Anaphylaxis of Guinea Pig

1) The test samples, adjuvant control and negative control were the same as described in Example 28.
Positive control
Name: human serum albumin
Lot Number: 201206043
Manufacturer: Shanghai Institute of Biological Products Co., Ltd.
Reason for selection: the product was a known positive sensitizer for guinea pigs
2) Experiment Methods
Animals: Hartley guinea pigs (SPF grade, Beijing Charles River Laboratories. Inc.)
Quantity: 24 guinea pigs (6 guinea pigs in each group, with half male and half female mice)
Route of administration: intramuscular injection for sensitization, and foot intravenous injection for stimulation.

TABLE 15

Group division and administration scheme

| | Groups | Male | Female | Sensitization (i.m) | Stimulation (i.v.) |
|---|---|---|---|---|---|
| 1 | Negative control group | 1-3 | 4-6 | Once every other day for totally 3 times | 14 days after the last sensitization |
| 2 | Positive control group | 7-9 | 10-12 | Once every other day for totally 3 times | 14 days after the last sensitization |
| 3 | Low dosage group of the test sample | 13-15 | 16-18 | Once every other day for totally 3 times | 14 days after the last sensitization |
| 4 | High dosage group of the test sample | 19-21 | 22-24 | Once every other day for totally 3 times | 14 days after the last sensitization |

TABLE 16

Intended dosages

| Groups | | Sensitization (i.m)a | | Stimulation (i.v.)b | |
|---|---|---|---|---|---|
| | | Administration dosage | Volume | Dosage | Volume |
| 1 | Negative control group | — | 0.6 mL/animal | — | 1.2 mL/animal |
| 2 | Positive control group | 18 mg/animal | 0.6 mL/animal | 36 mg/animal | 1.2 mL/animal |
| 3 | Test samples Low dosage group | 0.1 dose/animal | 0.06 mL/animal | 0.2 dose/animal | 0.12 mL/animal |
| 4 | Test samples High dosage group | 1 dose/animal | 0.6 mL/animal | 2 dose/animal | 1.2 mL/animal |

Note:
the dosages of the test samples for sensitization were 30 µg/kg and 300 µg/kg, respectively, in low and high dosage groups, corresponding to 15 and 150 folds of the intended clinical dosage.

3) Results: during sensitization, no abnormal reaction was observed in all animals.

TABLE 17

Summary of allergic reactions in animals in each group after stimulation

| Groups | Number of the animals | Number of the animals suffering allergy at different levels | | | | |
|---|---|---|---|---|---|---|
| | | Negative | Weakly positive | Positive | Strongly positive | Extremely strongly positive |
| Negative control group | 6 | 6 | 0 | 0 | 0 | 0 |
| Positive control group | 6 | 0 | 0 | 0 | 5 | 1 |
| Low dosage group of the test sample | 6 | 0 | 0 | 0 | 1 | 5 |
| High dosage group of the test sample | 6 | 0 | 0 | 0 | 0 | 6 |

Under the test conditions, the recombinant *Staphylococcus aureus* vaccine was intramuscularly injected for sensitization at a dosage of 0.1 dose/animal (corresponding to 15 folds of the intended clinical dosage) and 1 dose/animal (corresponding to 150 folds of the intended clinical dosage) (the total content of proteins in 1 dose was 120 µg), and intravenously injected at a dosage of 0.2 dose/animal and 2 dose/animal for stimulation, so that immediate allergy could be resulted in guinea pigs. The results were consistent with the features of allergy in the guinea pig caused by a common purified protein vaccine (such as tetanus vaccine, and diphtheria vaccine etc.).

Example 30: Toxicity Test of 4-Week Repeated Intramuscular Injection to SD Rats and 4-Week Recovery 1) The test samples, adjuvant control and negative control were the same as described in Example 28.

2) Experiment Methods

Animals: SD rats (SPF grade, Beijing Charles River Laboratories. Inc.)

Route of administration: intramuscular injection

Administration frequency and period: administration once on D1, D15, D22 and D29, for totally 4 times.

TABLE 18

Experiment scheme:

| Groups | Dosage a (dose/animal) | Volume b (mL/animal) | Number of the animals/gender c | No. Male | No. Female |
|---|---|---|---|---|---|
| Main test groups | | | | | |
| 1 Negative control group | 0 | 1.8 | 10 + 5 | 13-2331~13-2345 | 13-2346~13-2360 |
| 2 Adjuvant control group | 3 | 1.8 | 10 + 5 | 13-2361~13-2375 | 13-2376~13-2390 |
| 3 Low dosage group of the test sample | 0.3 | 0.18 | 10 + 5 | 13-2391~13-2405 | 13-2406~13-2420 |
| 4 Middle dosage group of the test sample | 1 | 0.6 | 10 + 5 | 13-2421~13-2435 | 13-2436~13-2450 |
| 5 High dosage group of the test sample | 3 | 1.8 | 10 + 5 | 13-2451~13-2465 | 13-2466~13-2480 |
| Satellite groups d | | | | | |
| 6 Negative control group | 0 | 1.8 | 5 | 13-2481~13-2485 | 13-2486~13-2490 |
| 7 Low dosage group of the test sample | 0.3 | 0.18 | 5 | 13-2491~13-2495 | 13-2496~13-2500 |

TABLE 18-continued

Experiment scheme:

| Groups | Dosage a (dose/animal) | Volume b (mL/animal) | Number of the animals/gender c | No. Male | Female |
|---|---|---|---|---|---|
| 8 Middle dosage group of the test sample | 1 | 0.6 | 5 | 13-2501~13-2505 | 13-2506~13-2510 |
| 9 High dosage group of the test sample | 3 | 1.8 | 5 | 13-2511~13-2515 | 13-2516~13-2520 | a. The intended clinical dosage was 0.6 mL/dose/time/person, and the dosage unit for rats was "dose/animal". 1 dose corresponded to 1 clinical inoculation dosage.
b. The volume in the Table above was a theoretical administration volume, and the actual administration volume was kept in the original recording.
c. The first 10 animals/gender/group were used for anatomy after administration for 4 weeks (D32), and the last 5 animals/gender/group were used for anatomy after 4-week recovery(D57).
d. The blood samples were collected from the animals in the satellite groups only for antibody and cytokine assays. Other data were stored in the source materials, and not presented in the report.

3) Test Results

TABLE 19

Clinical observation (D1-D32)

| Gender | Groups | Dosage (dose/animal) | n | Sclerosis | umbilicus regionupheaval |
|---|---|---|---|---|---|
| ♂ | 1 | 0 | 15 | 0 | 0 |
|  | 2 | 3 | 15 | 9 | 0 |
|  | 3 | 0.3 | 15 | 3 | 0 |
|  | 4 | 1 | 15 | 14 | 1 |
|  | 5 | 3 | 15 | 15 | 0 |
| ♀ | 1 | 0 | 15 | 0 | 0 |
|  | 2 | 3 | 15 | 4 | 0 |
|  | 3 | 0.3 | 15 | 1 | 0 |
|  | 4 | 1 | 15 | 4 | 0 |
|  | 5 | 3 | 15 | 12 | 0 |

Group 1: negative control group;
Group 2: adjuvant control group;
Group 3: low dosage group of the test sample;
Group 4: middle dosage group of the test sample; and
Group 5: high dosage group of the test sample

TABLE 20

Clinical observation on the animas (D32-D57)

| Gender | Groups | Dosage (dose/animal) | n | Sclerosis | umbilicus region upheaval |
|---|---|---|---|---|---|
| ♂ | 1 | 0 | 15 | 0 | 0 |
|  | 2 | 3 | 15 | 9 | 0 |
|  | 3 | 0.3 | 15 | 3 | 0 |
|  | 4 | 1 | 15 | 14 | 1 |
|  | 5 | 3 | 15 | 15 | 0 |
| ♀ | 1 | 0 | 15 | 0 | 0 |
|  | 2 | 3 | 15 | 4 | 0 |
|  | 3 | 0.3 | 15 | 1 | 0 |
|  | 4 | 1 | 15 | 4 | 0 |
|  | 5 | 3 | 15 | 12 | 0 |

Group 1: negative control group;
Group 2: adjuvant control group;
Group 3: low dosage group of the test sample;
Group 4: middle dosage group of the test sample; and
Group 5: high dosage group of the test sample

TABLE 21

Summary of the blood cell counts in the male animals (3 days after the last administration, D32)

| Groups | Dosage (dose/animal) |  | PLT Thrombocyte ($\times 10^9$/L) | WBC Leucocyte ($\times 10^9$/L) | Neut Neutrophilic granulocyte (%) |
|---|---|---|---|---|---|
| 1 | 0 | Mean ± SD | 1301.4 ± 153.5 | 9.47 ± 2.17 | 11.58 ± 3.11 |
|  |  | n | 10 | 10 | 10 |
| 2 | 3 | Mean ± SD | 1441.6 ± 142.2 | 10.93 ± 1.69 | 12.48 ± 1.79 |
|  |  | n | 10 | 10 | 10 |
| 3 | 0.3 | Mean ± SD | 1301.9 ± 100.3 | 10.69 ± 2.20 | 13.57 ± 4.50 |
|  |  | n | 10 | 10 | 10 |
| 4 | 1 | Mean ± SD | 1401.7 ± 203.6 | 12.33 ± 2.54* | 19.55 ± 3.01* |
|  |  | n | 10 | 10 | 10 |
| 5 | 3 | Mean ± SD | 1597.0 ± 219.6* | 14.17 ± 3.33* | 22.93 ± 4.64* |
|  |  | n | 10 | 10 | 10 |

Group 1: negative control group;
Group 2: adjuvant control group;
Group 3: low dosage group of the test sample;
Group 4: middle dosage group of the test sample; and
Group 5: high dosage group of the test sample

TABLE 22

Summary of the blood cell counts in the female animals (3 days after the last administration, D32)

| Groups | Dosage (dose/animal) | | PLT (×10$^9$/L) | WBC (×10$^9$/L) | Neut Neutrophilic granulocyte (%) |
|---|---|---|---|---|---|
| 1 | 0 | Mean ± SD | 1379.0 ± 158.8 | 9.89 ± 4.84 | 9.16 ± 4.15 |
|   |   | n | 10 | 10 | 10 |
| 2 | 3 | Mean ± SD | 1431.4 ± 143.5 | 11.77 ± 3.95 | 9.86 ± 2.38 |
|   |   | n | 10 | 10 | 10 |
| 3 | 0.3 | Mean ± SD | 1453.7 ± 129.0 | 9.82 ± 2.74 | 12.32 ± 4.74 |
|   |   | n | 10 | 10 | 10 |
| 4 | 1 | Mean ± SD | 1389.6 ± 163.6 | 12.38 ± 4.84 | 15.16 ± 3.28* |
|   |   | n | 10 | 10 | 10 |
| 5 | 3 | Mean ± SD | 1611.7 ± 154.3* | 15.89 ± 4.17* | 22.44 ± 6.77* |
|   |   | n | 10 | 10 | 10 |

Group 1: negative control group;
Group 2: adjuvant control group;
Group 3: low dosage group of the test sample;
Group 4: middle dosage group of the test sample; and
Group 5: high dosage group of the test sample As indicated by the body temperature, the T lymphocyte subpopulation assay and the biochemical assay of blood, no toxicologically abnormal change was observed in the animals of each dosage group of the test sample, as compared with the negative control group.

As compared with the negative control group, no test sample-related toxicologically abnormal change was observed for the indices of the male animals, including the organ weight, the organ/body weight ratio and the organ/brain weight ratio.

Antibodies against each component in all dosage groups of the test sample could be detected on Day 57.

TABLE 23

IgG antibody detection in the serum (HI)

| Testing time | Groups | Dosage (dose/animal) | N | Generation rate of the antibody |
|---|---|---|---|---|
| D1 | Negative control group | 0 | 10 | 0/10 |
|   | Low dosage group of the test sample | 0.3 | 10 | 0/10 |
|   | Middle dosage group of the test sample | 1 | 10 | 0/10 |
|   | High dosage group of the test sample | 3 | 10 | 0/10 |
| D14 | Negative control group | 0 | 10 | 0/10 |
|   | Low dosage group of the test sample | 0.3 | 10 | 5/10 |
|   | Middle dosage group of the test sample | 1 | 10 | 2/10 |
|   | High dosage group of the test sample | 3 | 10 | 6/10 |
| D21 | Negative control group | 0 | 10 | 0/10 |
|   | Low dosage group of the test sample | 0.3 | 10 | 7/10 |
|   | Middle dosage group of the test sample | 1 | 10 | 10/10 |
|   | High dosage group of the test sample | 3 | 10 | 9/10 |
| D28 | Negative control group | 0 | 10 | 0/10 |
|   | Low dosage group of the test sample | 0.3 | 10 | 9/10 |
|   | Middle dosage group of the test sample | 1 | 10 | 10/10 |
|   | High dosage group of the test sample | 3 | 10 | 10/10 |
| D57 | Negative control group | 0 | 10 | 0/10 |
|   | Low dosage group of the test sample | 0.3 | 10 | 10/10 |
|   | Middle dosage group of the test sample | 1 | 10 | 10/10 |
|   | High dosage group of the test sample | 3 | 10 | 10/10 |

TABLE 24

IgG antibody detection in the serum (MntC)

| Testing time | Groups | Dosage (dose/animal) | N | Generation rate of the antibody |
|---|---|---|---|---|
| D1 | Negative control group | 0 | 10 | 0/10 |
|   | Low dosage group of the test sample | 0.3 | 10 | 0/10 |
|   | Middle dosage group of the test sample | 1 | 10 | 0/10 |
|   | High dosage group of the test sample | 3 | 10 | 0/10 |
| D14 | Negative control group | 0 | 10 | 0/10 |
|   | Low dosage group of the test sample | 0.3 | 10 | 10/10 |
|   | Middle dosage group of the test sample | 1 | 10 | 10/10 |
|   | High dosage group of the test sample | 3 | 10 | 10/10 |
| D21 | Negative control group | 0 | 10 | 0/10 |
|   | Low dosage group of the test sample | 0.3 | 10 | 10/10 |
|   | Middle dosage group of the test sample | 1 | 10 | 10/10 |
|   | High dosage group of the test sample | 3 | 10 | 10/10 |
| D28 | Negative control group | 0 | 10 | 0/10 |
|   | Low dosage group of the test sample | 0.3 | 10 | 10/10 |

TABLE 24-continued

IgG antibody detection in the serum (MntC)

| Testing time | Groups | Dosage (dose/animal) | N | Generation rate of the antibody |
|---|---|---|---|---|
| | Middle dosage group of the test sample | 1 | 10 | 10/10 |
| | High dosage group of the test sample | 3 | 10 | 10/10 |
| D57 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |

TABLE 25

IgG antibody detection in the serum (mSEB)

| Testing time | Groups | Dosage (dose/animal) | N | Generation rate of the antibody |
|---|---|---|---|---|
| D1 | Negative control group | 0 | 10 | 0/10 |
| | Low dosage group of the test sample | 0.3 | 10 | 0/10 |
| | Middle dosage group of the test sample | 1 | 10 | 0/10 |
| | High dosage group of the test sample | 3 | 10 | 0/10 |
| D14 | Negative control group | 0 | 10 | 0/10 |
| | Low dosage group of the test sample | 0.3 | 10 | 5/10 |
| | Middle dosage group of the test sample | 1 | 10 | 9/10 |
| | High dosage group of the test sample | 3 | 10 | 9/10 |
| D21 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |
| D28 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |
| D57 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |

TABLE 26

IgG antibody detection in the serum (SpA5 (KKAA))

| Testing time | Groups | Dosage (dose/animal) | N | Generation rate of the antibody |
|---|---|---|---|---|
| D1 | Negative control group | 0 | 10 | 0/10 |
| | Low dosage group of the test sample | 0.3 | 10 | 0/10 |
| | Middle dosage group of the test sample | 1 | 10 | 0/10 |
| | High dosage group of the test sample | 3 | 10 | 0/10 |
| D14 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |
| D21 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |
| D28 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |
| D57 | Negative control group | 0 | 10 | 0/10 |
| | Low dosage group of the test sample | 0.3 | 10 | 10/10 |
| | Middle dosage group of the test sample | 1 | 10 | 10/10 |
| | High dosage group of the test sample | 3 | 10 | 10/10 |

Example 31: Toxicity Test of 4-Week Repeated Intramuscular Injection to Cynomolgus Monkeys and 4-Week Recovery 1) The test samples, adjuvant control and negative control were the same as described in Example 28.

2) Experiment Methods

Experiment animals: cynomolgus monkeys (ordinary grade, Hainan experimental primate corporation)

Route of administration: intramuscular injection

Administration frequency and period: administration once on D1, D15, D22 and D29, for totally 4 times.

TABLE 27

Experiment scheme

| Groups | Dosage a (dose/animal) | Volume b (mL/animal) | Number of the animal c (animal/gender) | No. Male | Female |
|---|---|---|---|---|---|
| 1 Negative control group | 0 | 3 | 2 + 2 | 13-4161~13-4164 | 13-4165~13-4168 |
| 2 Adjuvant control group | 5 | 3 | 2 + 2 | 13-4169~13-4172 | 13-4173~13-4176 |
| 3 Low dosage group of the test sample | 0.2 | 0.12 | 2 + 2 | 13-4177~13-4180 | 13-4181~13-4184 |
| 4 Middle dosage group of the test sample | 1 | 0.6 | 2 + 2 | 13-4185~13-4188 | 13-4189~13-4192 |
| 5 High dosage group of the test sample | 5 | 3 | 2 + 2 | 13-4193~13-4196 | 13-4197~13-4200 | a. The intended clinical dosage was 0.6 mL/dose/time/person, and the dosage unit for the monkeys was "dose/animal". 1 dose corresponded to 1 clinical inoculation dosage.
b. The volume in the Table above was a theoretical administration volume, and the actual administration volume was kept in original recording.
c. For each group, the first 2 animals/gender/group were used for anatomy on day 3 after the last administration, and the last 2 animals/gender/group were used for anatomy after 4-week recovery.

3) Test Results:

TABLE 28

Clinical observation (D1-D32)

| Groups | Dosage (dose/animal) | n | Loose stools | Erythema | Sclerosis |
|---|---|---|---|---|---|
| 1 | 0 | 8 | 0 | 0 | 0 |
| 2 | 5 | 8 | 0 | 1 | 7 |
| 3 | 0.2 | 8 | 1 | 0 | 1 |
| 4 | 1 | 8 | 0 | 2 | 7 |
| 5 | 5 | 8 | 0 | 1 | 8 |

As indicated by the body weight, the body temperature, the T lymphocyte subpopulation assay, the blood cell assay and the biochemical assay of blood, no test sample-related toxicologically abnormal change was observed, as compared with the negative control group.

TABLE 29

Results of ELISPOT (D18)

| Groups | Dosage (dose/animal) | | HI | MntC | mSEB | SpA5 |
|---|---|---|---|---|---|---|
| 1 | 0 | Mean ± SD | 33.8 ± 50.8 | 38.8 ± 69.8 | 36.3 ± 83.8 | 6.9 ± 19.4 |
| | | n | 8 | 8 | 8 | 8 |
| 2 | 5 | Mean ± SD | 111.3 ± 247.1 | 195.6 ± 403.2 | 95.6 ± 250.5 | 6.9 ± 10.3 |
| | | n | 8 | 8 | 8 | 8 |
| 3 | 0.2 | Mean ± SD | 89.4 ± 135.3 | 142.5 ± 140.8 | 85.6 ± 151.6 | 28.1 ± 56.6 |
| | | n | 8 | 8 | 8 | 8 |
| 4 | 1 | Mean ± SD | 168.1 ± 312.3 | 459.4 ± 602.6 | 203.8 ± 272.3 | 290.6 ± 200.4* |
| | | n | 8 | 8 | 8 | 8 |
| 5 | 5 | Mean ± SD | 81.9 ± 121.2 | 29.4 ± 55.3 | 35.6 ± 81.3 | 35.6 ± 81.3 |
| | | n | 8 | 8 | 8 | 8 |

Group 1: negative control group; Group 2: adjuvant control group; Group 3: low dosage group of the test sample; Group 4: middle dosage group of the test sample; and Group 5: high dosage group of the test sample

TABLE 30

Experiment scheme

| Groups | Dosage a (dose/animal) | Volume b (mL/animal) | Number of the animals Male | Female c |
|---|---|---|---|---|
| 1 Negative control group | 0 | 1.8 | 28 | 28 + 28 |
| 2 Adjuvant control group | 3 | 1.8 | 28 | 28 + 28 |
| 3 Low dosage group of the test sample | 1 | 0.6 | 28 | 28 + 28 |
| 4 High dosage group of the test sample | 3 | 1.8 | 28 | 28 + 28 |

Note:
the first 28 female animals in each group were used for normal delivery until the stage of lactation is finished, and the last 28 animals were used for anatomy on Day 20 of gestation (GD20) to examine the fetal rats.

Administration frequency and period: the male rats were administrated for 3 times (D1, D15 and D22) before mating; and the female rats were also administrated for 3 times (D1, D15 and D22) before mating. The male and female rats were raised in the same cage for mating 1 week after administration of the last dose to the male rats. The female rats were administrated once on Day 6 of gestation (GD6).

3) Test Results

As compared with the negative control group, no toxicological abnormal change was observed for the body weight of the animals in each dosage groups of the test sample.

Example 32: Toxicity Test on Reproductive Development of SD Rats Administrated by Repeated Intramuscular Injection 1) The test samples, adjuvant control and negative control were the same as described in Example 28.

2) Experiment Methods:

Animals: SD rats (SPF grade, Beijing Charles River Laboratories. Inc.)

As compared with the negative control group, no toxicological abnormal change was observed for the food intake of the animals in each dosage groups of the test sample.

TABLE 31

Reproductive capacity of the parent male and female rats

| | Negative control group (0 dose/animal) | Adjuvant control group (3 doses/animal) | Low dosage group of the test sample (1 dose/animal) | High dosage group of the test sample (3 doses/animal) |
|---|---|---|---|---|
| Number of the animals in the same cage | 28(♂), 28 (♀) | 28 (♂), 28 (♀) | 28 (♂), 28 (♀) | 28 (♂), 28 (♀) |
| Mating rate of the male rats (%) | 100.0 (28/28) | 100.0 (28/28) | 100.0 (28/28) | 100.0 (28/28) |
| Fertility rate of the male rats (%) | 85.7 (24/28) | 78.6 (22/28) | 85.7 (24/28) | 78.6 (22/28) |
| Mating rate of the female rats (%) | 100.0 (28/28) | 100.0 (28/28) | 100.0 (28/28) | 100.0 (28/28) |
| Fertility rate of the female rats (%) | 85.7 (24/28) | 78.6 (22/28) | 85.7 (24/28) | 78.6 (22/28) |
| Pregnancy rate (%) | 85.7 (24/28) | 78.6 (22/28) | 85.7 (24/28) | 78.6 (22/28) |
| Gestation rate (%) | 85.7 (24/28) | 78.6 (22/28) | 85.7 (24/28) | 78.6 (22/28) |
| Number of the female rats of irregular estrous cycle | 5 | 5 | 2 | 7 |
| Rate of irregularly estrous rats (%) | 17.9 (5/28) | 17.9 (5/28) | 7.1 (2/28) | 25.0 (7/28) |
| Days in the same cage | 5.4 ± 4.9 | 4.5 ± 3.9 | 4.0 ± 3.1 | 4.8 ± 4.3 |
| Days of mating | 5.4 ± 4.9 | 4.5 ± 3.9 | 4.0 ± 3.1 | 4.8 ± 4.3 |

Detection Indices for the Parent Male Rats:

TABLE 32

Organ weight and coefficient of the parent male rats

| | | | | Organ coefficient (%) | | |
|---|---|---|---|---|---|---|
| Groups | Testicle (bilateral, g) | Epididymis (bilateral, g) | Prostate (g) | Testicle (bilateral) | Epididymis (bilateral) | Prostate |
| Negative control group | 3.123 ± 0.291 | 1.033 ± 0.124 | 1.014 ± 0.156 | 0.743 ± 0.083 | 0.245 ± 0.027 | 0.241 ± 0.038 |
| Adjuvant control group | 3.026 ± 0.505 | 1.023 ± 0.154 | 1.072 ± 0.150 | 0.750 ± 0.142 | 0.254 ± 0.045 | 0.266 ± 0.042 |
| Low dosage group of the test sample | 3.101 ± 0.346 | 1.028 ± 0.090 | 1.034 ± 0.198 | 0.765 ± 0.096 | 0.254 ± 0.027 | 0.254 ± 0.046 |
| High dosage group of the test sample | 3.114 ± 0.283 | 1.038 ± 0.098 | 1.100 ± 0.215 | 0.779 ± 0.071 | 0.260 ± 0.024 | 0.275 ± 0.054* |

Sperm motility and counts of the parent male rats: as compared with the negative control group, no statistical differences of the sperm motility, the ratio of forward motile sperm, the average speed, the speed for linear motion, the speed for curvilinear motion, the amplitude of lateral head displacement, the beat cross frequency, the forward motility, the straight motility, the elongation and the sperm counts of cauda epididymidis were observed in the male rats in each dosage group of the test sample ($P>0.05$).

Morphological examination on the sperm of the parent male rats: as compared with the negative control group, no statistical differences of the headless deformity rate, the hook-less deformity rate, amorphous head deformity rate, the tail-less deformity rate, the folding deformity rate, the prehensile tail rate, the rate of excessive hook bending and the total deformity rate of sperms were observed in the animals in the high dosage group of the test sample ($P>0.05$).

TABLE 33

Examination on the parent female rats by cesarean delivery (conducted on GD20)

| | Negative control group (0 dose/animal) | Adjuvant control group (3 doses/animal) | Low dosage group of the test sample (1 dose/animal) | High dosage group of the test sample (3 doses/animal) |
|---|---|---|---|---|
| Weight of uterus and fetus (g) | 75.218 ± 19.530 | 70.757 ± 23.323 | 73.536 ± 13.972 | 77.624 ± 12.000 |
| Average number of corpus luteum graviditatis | 18.5 ± 3.4 | 17.5 ± 3.6 | 17.6 ± 3.6 | 17.5 ± 3.0 |
| Average nidation number | 15.1 ± 3.5 | 14.2 ± 3.5 | 14.5 ± 2.8 | 15.3 ± 2.1 |
| Nidation rate (%) | 82.63 ± 16.84 | 82.11 ± 16.94 | 83.93 ± 15.01 | 88.78 ± 11.99 |
| Loss rate before nidation (%) | 17.37 ± 16.84 | 17.89 ± 16.94 | 16.07 ± 15.01 | 11.22 ± 11.99 |
| Loss rate after nidation (%) | 8.72 ± 11.26 | 9.88 ± 21.92 | 8.89 ± 9.75 | 7.21 ± 7.64 |
| Live birth rate (%) | 91.28 ± 11.26 | 90.12 ± 21.92 | 91.11 ± 9.75 | 92.79 ± 7.64 |
| Adsorbed embryo rate (%) | 8.72 ± 11.26 | 9.88 ± 21.92 | 8.89 ± 9.75 | 6.95 ± 7.57 |
| Stillbirth rate (%) | 0.00 ± 0.00 | 0.00 ± 0.00 | 0.00 ± 0.00 | 0.27 ± 1.25 |

TABLE 34

Examination on the fetal rats

| Groups | Fetal body weight (g) Male | Fetal body weight (g) Female | Weight of placenta (g) | Fetal body length (mm) | Fetal tail length (mm) | Gender ratio (number of male rats/number of female rats) |
|---|---|---|---|---|---|---|
| Negative control group | 3.549 ± 0.314 | 3.451 ± 0.307 | 0.499 ± 0.065 | 36.47 ± 0.90 | 11.87 ± 0.34 | 1.3 (191/144) |
| Adjuvant control group | 3.637 ± 0.301 | 3.516 ± 0.335 | 0.541 ± 0.183 | 36.76 ± 0.86 | 11.89 ± 0.41 | 1.0 (135/137) |
| Low dosage group of the test sample | 3.653 ± 0.406 | 3.521 ± 0.303 | 0.499 ± 0.060 | 36.57 ± 0.97 | 12.00 ± 0.31 | 1.3 (181/139) |
| High dosage group of the test sample | 3.614 ± 0.337 | 3.461 ± 0.375 | 0.476 ± 0.054 | 36.64 ± 0.99 | 12.03 ± 0.35 | 1.2 (171/142) |

As compared with the negative control group, no statistical differences of the deformed fetal appearance rate and the abnormal placenta rate were seen in each dosage group of the test sample ($P>0.05$).

TABLE 35

Examination on the fetal skeleton

| | Negative control group (0 dose/animal) | High dosage group of the test sample (3 doses/animal) |
|---|---|---|
| Number of the litters examined | 23 | 22 |
| Number of the fetal rats examined | 166 | 163 |
| Left middle hand bones | 3.41 ± 0.32 | 3.50 ± 0.33 |
| Right middle hand bones | 3.41 ± 0.32 | 3.48 ± 0.33 |
| Left middle foot bones | 3.98 ± 0.05 | 4.00 ± 0.02 |
| Right middle foot bones | 3.99 ± 0.05 | 4.00 ± 0.02 |
| Number of the breastbones | 5.46 ± 0.56 | 5.42 ± 0.65 |
| Number of the sacrococcygeal vertebra | 7.33 ± 0.46 | 7.36 ± 0.68 |
| Rate of abnormal bones (%) | 5.21 ± 10.23 | 2.24 ± 4.91 |
| Rate of aberrant bones (%) | 14.72 ± 18.28 | 11.02 ± 17.53 |

TABLE 36

Examination on the fetal organs

| | Negative control group (0 dose/animal) | High dosage group of the test sample (3 doses/animal) |
|---|---|---|
| Number of the litters examined | 24 | 22 |
| Number of the fetal rats examined | 161 | 150 |

TABLE 36-continued

Examination on the fetal organs

| | Negative control group (0 dose/animal) | High dosage group of the test sample (3 doses/animal) |
|---|---|---|
| Rate of abnormal organs (%) | 0.60 ± 2.92 | 0.76 ± 3.55 |
| Rate of aberrant organs (%) | 27.41 ± 23.21 | 28.78 ± 24.12 |

Examination Items for the Fetal Rats of Generation F1
Survival of the fetal rats of generation F1
Body weight and gender ratio of the fetal rats of generation F1
Deformed appearance of the fetal rats of generation F1
Examination on the body development indices of the fetal rats of generation F1;
Examination on the reflex development indices of the fetal rats of generation F1;
As compared with the negative control group, no statistical differences of each index were seen in the generation F1 fetal rats in each dosage group of the test sample (P>0.05).
Results:
No adverse effects were seen on the fertility of the parent male and female rats, and on the gestation/lactation of the female rats.
No toxicity and teratogenicity were seen on the development of the embryo-fetus.
No obvious effects on the body development indices and the reflex development indices were seen in the fetal rats of generation F1.

D. Establishment of Animal Models

During the research process of the present invention, suitable animal models were demanded to simulate human pathogenic environment for investigation on the pathogenic mechanism and process of *Staphylococcus aureus*. The action mechanism of therapeutic medicines or vaccines could be elucidated by pharmacological and pharmacodynamic experiments, so that novel medicines for the prevention and treatment of *Staphylococcus aureus* infections would be developed. Accordingly, animal models were required to stimulate the diseases. In recent years, a great number of experiments were carried out by investigators in China or abroad using pneumonia animal models, including rhesus monkey model, rabbit model, mouse model, pig model, and rat model, etc. The monkey was an ideal experimental animal, due to similar physiologic structure to human. However, the use of monkey in experiment was limited due to lower quantity and higher cost. At present, rodents were commonly adopted in a pneumonia animal model in China or abroad.

Researches on establishing a pneumonia mouse model were reported. For example, a pneumonia mouse model was generated by the follows methods: adding 50 μL bacteria suspension directly to the left nasal cavity of a BALB/C mouse dropwise, as described by Wang Xing et al. (Wang Xing et al., Chinese Journal of antibiotics, 2011, 8(36), 8, 617-602); or after weighing and intraperitoneal anesthesia using 10% chloral hydrate solution, fixing a Kunming mouse of 6-8 weeks old on an experiment table in supine position to expose glottis, and then injecting bacteria suspension to the tracheae using a self-made syringe with a blunt needle inserted into the upper trachea, as described by Lv Xiaoyan et al. (Lv Xiaoyan et al., Shandong Medical Journal, 2010, 50(3), 10-12). The pneumonia model could be established by the methods above. However, problems still existed in these methods, which mainly included: 1. a proportion of bacteria suspension might be added into oral cavity rather than lung for the mouse used without anaesthesia, since the nasal cavity was in connection with the oral cavity, so that the infection dosage could not be controlled precisely, resulting in an unstable model; 2. as an invasive method, inserting a needle into the trachea would hurt the organs of the animal, or even kill the animal during operation, although the infection dosage could be controlled; 3. there were so many mouse species that no susceptible model had been definitely determined; 4. unstable infection and colonization might lead to an unstable model, and success in establishing a model depended on a stable infection dosage.

Based on the problems above, in this section, the present invention provided a method for establishing a *Staphylococcus aureus* pneumonia model, in order to enhance the accuracy of the infection by bacteria suspension, increase the infection efficiency, and improve the stability of the pneumonia model.

The method for establishing a *Staphylococcus aureus* pneumonia model includes the following steps:
(1) anesthetizing the mouse; (2) subject the mouse to nasal drip;
wherein:
In step (1), the mouse was anaesthetized by isoflurane; preferably, anaesthesia was performed by inhalation of isoflurane at a concentration of 4%-6% (preferably, 5%) delivered in oxygen, and after the stage of deep anaesthesia was attained, anaesthesia was maintained by delivering isoflurane at a concentration of 2%-4% (preferably, 3%).

In step (2), a. during nasal drip, the supination amplitude of the mouse head should not larger than the physiological curvature of nasopharynx; b. medicine solution was dropped along the lateral wall of nasal cavity, in order to avoid as many bubbles generated during nasal drip as possible; c. at the beginning moment of inspiration, less than 5 μL medicine was dropped; d. bacteria density was from $2 \times 10^{10}$-$2 \times 10^{11}$ CFU/mL; e total dosage of bacteria was $5 \times 10^9$-$1 \times 10^{10}$ CFU during nasal drip. Preferably, two separate nasal drips (each of a volume of 25-35 μL) were performed with a total volume of 50-70 μL and a interval of 30 min.

Preferably, infection was evaluated in two ways: lung tissue culture and pathological section. Healthy mouse was used as a control.

Preferably, C57BL/6J mouse was used; and more preferably, the C57BL/6J mouse was of SPF grade and 8-week old.

The infection conducted by the method of the invention was easily controllable, and stable, with higher infection rate. The infection could result in obvious symptoms of pneumonia.

The materials and primary reagents used in this section were as follows:
1. Experiment Animals
Female C57BL/6J mice of 6-8 weeks old, supplied by Beijing HFK Bioscience Co., Ltd.
2. Strains (Purchased from ATCC);
*Staphylococcus aureus* strain MRSA 252, *Staphylococcus aureus* strain MRSA US-300, *Staphylococcus aureus* strain MRSA MW2, *Staphylococcus aureus* strain MRSA WHO-2, *Staphylococcus aureus* strain MRSA COL, and *Staphylococcus aureus* strain MRSA NEWMAN, were preserved in a refrigerator at −80° C. in our lab.
3. Equipments and Reagents
All equipments used were ordinary in the field of biology, including a incubator, a centrifuge, a spectrophotometer, a super-clean bench, and a shaker, etc.

MHA culture medium (purchased from Beijing Aoboxing Biotechnology Co., Ltd.), MHB culture medium (purchased from Beijing Aoboxing Biotechnology Co., Ltd.), MH agar plate and liquid medium (purchased from Beijing Aoboxing Biotechnology Co., Ltd.), NaCl (NS, supplied by Southwest Pharmaceutical Co., Ltd.), and isoflurane (purchased from Shandong Keyuan Pharmaceutical Co., Ltd.).

Recombinant *Staphylococcus aureus* vaccine, containing SpA5, HI, MntC and mSEB protein, each at a concentration of 50 μg/ml.

Example 33: Preparation of *Staphylococcus aureus* Suspension

Cryopreserved MRSA 252 was revived by aerobic culture on an MH agar plate at 37° C. over night. Individual colonies were picked up and inoculated to 1000 mL MH liquid medium. Subsequently, it was incubated aerobically in a shaker at 210 rpm for 7 h at 37° C. The suspension was centrifugated at 4700 rpm to collect the bacteria, which was then re-suspended in physiological saline after washing by physiological saline twice. $OD_{600}$ of the test suspension was detected by a spectrophotometer, and the concentration of bacteria was calculated based on $1OD=2\times10^9$ CFU/mL.

Example 34: Establishment of Anaesthesia and Nasal Drip Scheme of Mouse

In the infection test using the *Staphylococcus aureus* pneumonia model, mice were initially anaesthetized by isoflurane to ensure a successful nasal drip. Procedure for anaesthesia: anaesthesia was performed by inhalation of isoflurane at a concentration of 5% delivered in oxygen, and after the stage of deep anesthesia was attained, anaesthesia was maintained by delivering isoflurane at a concentration 3%. Using this method, favorable anaesthesia effect could be achieved. A stable model depended on a controlled dosage of nasal drip. In order to control the dosage better, to prevent the bacteria suspension from entering the oral cavity, and to avoid generating bubbles, the following measures were adopted: the supination amplitude of the mouse head should not be larger than the physiological curvature of nasopharynx during nasal drip, since the physiological curvature allowed the nasal drops to enter the oral cavity more easily at larger supination amplitude; (2) dropping the medicine solution along the lateral wall of nasal cavity, in order to avoid as many bubbles generated during nasal drip as possible; (3) performing with a good rhythm, and dropping less than 5 μL medicine at the beginning moment of inspiration; (4) two separate nasal drips (each of a volume of 25 μL) were performed at an interval of 30 min, since the dosage of 50 μL used in this Example was too large for a single dose. (5) As discovered according to the experiments using the bacteria suspensions of various concentrations, less bubbles were generated at a bacteria density of about $2\times10^{10}$-$2\times10^{11}$ CFU/ml.

Example 35: Preliminary Investigation on the Infection Dosage

The MRSA 252 suspension of Examples 33 was adjusted to 5 concentrations using physiological saline. Female C57BL/6J mice were randomly divided into 5 groups. After anaesthesia by isoflurane, infection was performed to the mice via nasal drip with an infection dosage of 50 μL for each mouse. Physiological saline (NS) of the same volume was used as a control. Animal Groups and infection dosages were listed in Table 37. After infection, mice were observed every other day for survival or death. The observation continued for 10 days. After the observation, the rest animals were euthanized by $CO_2$ inhalation.

TABLE 37

Preliminary investigation on the infection dosage in the *Staphylococcus aureus* pneumonia model

| SA strains | Groups | Dosage (CFU) | Number | Concentration (CFU/ml) | Dropping volume (μL) |
|---|---|---|---|---|---|
| MRSA 252 | 1 | $1.5 \times 10^{10}$ | 10 | $3 \times 10^{11}$ | 50 |
| MRSA 252 | 2 | $1.2 \times 10^{10}$ | 10 | $2.4 \times 10^{11}$ | 50 |
| MRSA 252 | 3 | $1 \times 10^{10}$ | 10 | $2 \times 10^{11}$ | 50 |
| MRSA 252 | 4 | $8 \times 10^9$ | 10 | $1.6 \times 10^{11}$ | 50 |
| MRSA 252 | 5 | $5 \times 10^9$ | 10 | $1 \times 10^{11}$ | 50 |

Figure 55:
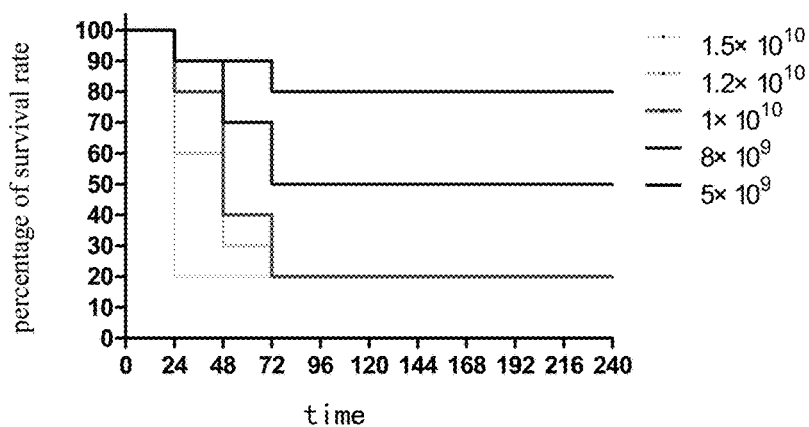
FIG. 55 is a plot showing preliminary investigation on the survival rate vs the infective dose of *Staphylococcus aureus*.

Initially, C57BL/6J mice were infected by the suspensions of *Staphylococcus aureus* strain MRSA 252 at various concentrations, and after 10 days observation, as shown in FIG. 55, the results were as follows: only 20% of mice died at a infection dosage of $5\times10^9$ CFU, 80% died at $1\times10^{10}$ CFU, and no obvious change was observed with further increased dosages, when infected by nasal drip.

Example 36: Determination of Final Infection Dosage

Based on preliminary investigation, the concentration was further adjusted. After anaesthesia by isoflurane, female C57BL/6J mice were infected via nasal drip with an infection dosage of 50 μL for each mouse. Physiological saline (NS) of the same volume was used as a control. Animal Groups and infection dosages were listed in Table 38. After infection, mice were observed every other day for survival or death. The observation continued for 10 days. After the observation, the rest animals were euthanized by $CO_2$ inhalation.

TABLE 38

Final infection dosage for the *Staphylococcus aureus* pneumonia model

| SA strains | Group | Dosage (CFU) | Number | Concentration (CFU/ml) | Dropping volume (μL) |
|---|---|---|---|---|---|
| MRSA 252 | 1 | $1 \times 10^{10}$ | 10 | $2 \times 10^{11}$ | 50 |
| MRSA 252 | 2 | $8 \times 10^9$ | 10 | $1.6 \times 10^{11}$ | 50 |
| MRSA 252 | 3 | $5 \times 10^9$ | 10 | $1 \times 10^{11}$ | 50 |

Figure 56:
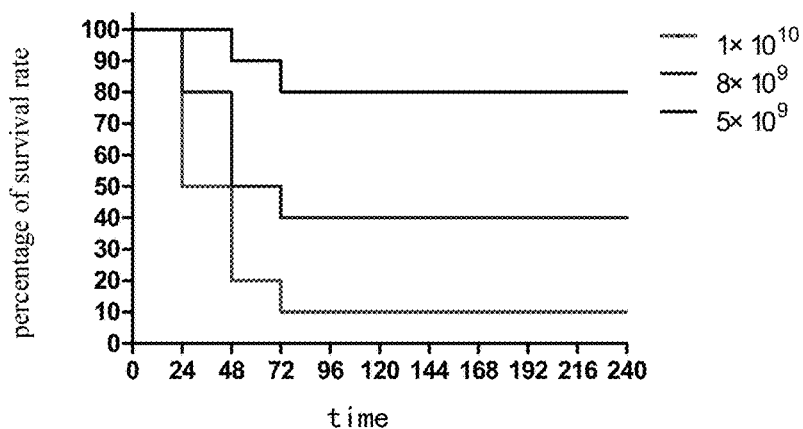
FIG. 56 is a plot that determines the infective dose in a pneumonia model.

Based on preliminary investigation, the concentration of bacteria for infection was further adjusted. The highest concentration of bacteria was controlled at $2\times10^{11}$ CFU/ml, since higher concentration is difficult to be conducted for nasal drip. After observation, as shown in FIG. 56, the results were listed as follows: the mortality rate was 20% at an infection dosage of $5\times10^9$ CFU, 40% at an infection dosage of $8\times10^9$ CFU, and 90% at an infection dosage of $1\times10^{10}$ CFU, which was substantially consistent with the previous results. The dosage of nasal drip was finally determined as $1\times10^{10}$ CFU for mouse.

Example 37: Evaluation on Infection 10 female C57BL/6J mice were infected at a final dosage of $1\times10^{10}$ CFU. The mice were killed 12 h after infection. Subsequently, both lungs were washed by physiological saline. The lungs were ground by adding 1 mL physiological saline. 100 µL suspension obtained after grinding was diluted in a ratio of 1:10000000. 100 µL dilution was smeared on an MH plate. After aerobic culture over night, the plate was observed and the colonies were counted. Log 10 of the colony counts was plotted. The mice were killed by cervical dislocation after anaesthesia, at 72 h after infection. Both lungs of the mouse were placed in 10% neutral formalin solution, fixed overnight, embedded in paraffin, sectioned (30 µm), and HE stained. Meanwhile, nasal drip was performed to 10 female C57BL/6J mice using physiological saline as a negative control.

Figure 57:
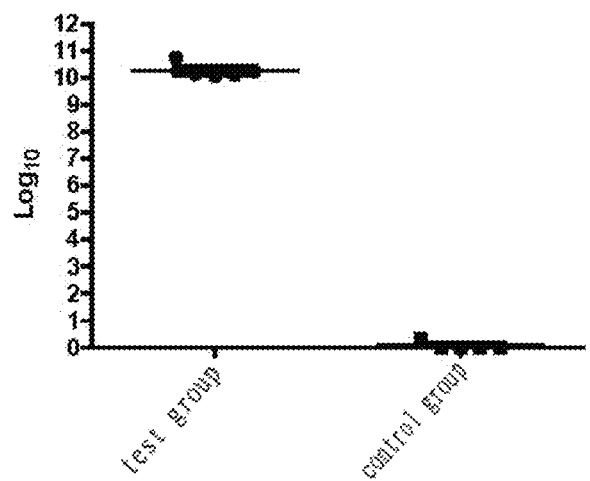
FIG. 57 illustrates the counts in both lungs in C57BL/6J mice after infection by SA77.

The mice were killed 12 h after infection. The lung tissue was cultured, and the result was shown in FIG. 57. After MRSA 252 infection, a positive rate of 100% was obtained for *Staphylococcus aureus* culture of the lung tissue, whereas negative result was observed for the control group, demonstrating that the infection was successful and stable.

Figure 58:
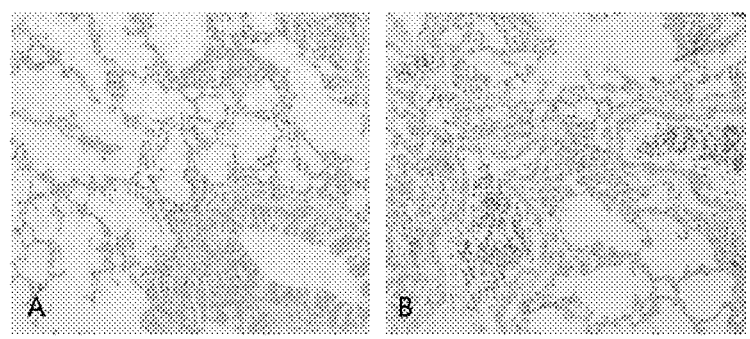
FIG. 58 illustrates pulmonary tissue sections in experiment group (100×, A for control group, and B for experiment group).

The mice were killed 72 h after infection. Both lungs of the mouse were placed in 10% neutral formalin solution, fixed overnight, embedded in paraffin, sectioned (30 µm), and HE stained. The result indicated that in mice of the experimental group, the following symptoms were observed, including: disappearance of some pulmonary alveolus structure, hyperemia and massive inflammatory cell infiltration. FIG. 58 showed thickening of alveolar septa, vicarious swelling of pulmonary alveolus and massive inflammatory cell infiltration. Obvious symptoms of pneumonia were induced in the *Staphylococcus aureus* infected C57BL/6J mouse model prepared using this method.

Example 38: Evaluation on the Immunoprotective Effect of the Recombinant *Staphylococcus aureus* Vaccine in a Pneumonia Model C57BL/6J mice were immunized by intramuscular injection of the recombinant *Staphylococcus aureus* vaccine using the procedure of immunization on Day 0, Day 3 and Day 7. On Day 10-14 after the last immunization, the cryopreserved MRSA 252, MRSA US-300, MRSA MW2, MRSA WHO-2, MRSA COL, and MRSA NEWMAN strain were revived. The concentration of the bacteria suspension was adjusted to LD80-LD90. After anaesthesia by isoflurane, infection was performed to the mice via nasal drip with an infection dosage of 50-70 µL for each mouse. Physiological saline (NS) of the same volume was used as a control. Animal Groups and infection dosages were listed in Table 39.

TABLE 39

Various strains and infection dosages used in the *Staphylococcus aureus* pneumonia model

| SA strains | Group | Dosage (CFU) | Quantity | Concentration (CFU/ml) | Volume of nasal drip (µl) |
|---|---|---|---|---|---|
| MRSA 252 | NS | $9.6 \times 10^9$ | 10 | $1.6 \times 10^{11}$ | 60 |
| MRSA 252 | vaccine | $9.6 \times 10^9$ | 10 | $1.6 \times 10^{11}$ | 60 |
| MRSA COL | NS | $9.6 \times 10^9$ | 10 | $1.6 \times 10^{11}$ | 60 |
| MRSA COL | vaccine | $9.6 \times 10^9$ | 10 | $1.6 \times 10^{11}$ | 60 |
| MRSA WHO-2 | NS | $9.6 \times 10^9$ | 10 | $1.6 \times 10^{11}$ | 60 |
| MRSA WHO-2 | vaccine | $9.6 \times 10^9$ | 10 | $1.6 \times 10^{11}$ | 60 |
| MRSA MW2 | NS | $8 \times 10^9$ | 10 | $1.6 \times 10^{11}$ | 50 |
| MRSA MW2 | vaccine | $8 \times 10^9$ | 10 | $1.6 \times 10^{11}$ | 50 |
| MRSA US-300 | NS | $1.12 \times 10^{10}$ | 10 | $1.6 \times 10^{11}$ | 70 |
| MRSA US-300 | vaccine | $1.12 \times 10^{10}$ | 10 | $1.6 \times 10^{11}$ | 70 |
| MRSA NEWMAN | NS | $9.6 \times 10^9$ | 10 | $1.6 \times 10^{11}$ | 60 |
| MRSA NEWMAN | vaccine | $9.6 \times 10^9$ | 10 | $1.6 \times 10^{11}$ | 60 |

After infection, mice were observed every other day for survival or death. The observation continued for 10 days. After the observation, the rest animals were euthanized by $CO_2$ inhalation.

TABLE 40

Survival rate (10 days later) in the pneumonia model infected by various strains after immunization by the *Staphylococcus aureus* vaccine

| SA strain | Group | Number | Number of dead mice | Mortality rate | Survival rate |
|---|---|---|---|---|---|
| MRSA 252 | NS | 10 | 9 | 90% | 10% |
| MRSA 252 | vaccine | 10 | 2 | 20% | 80% |
| MRSA COL | NS | 10 | 9 | 90% | 10% |
| MRSA COL | vaccine | 10 | 3 | 30% | 70% |
| MRSA WHO-2 | NS | 10 | 10 | 100% | 0% |
| MRSA WHO-2 | vaccine | 10 | 4 | 40% | 60% |
| MRSA MW2 | NS | 10 | 7 | 70% | 30% |
| MRSA MW2 | vaccine | 10 | 1 | 10% | 90% |
| MRSA US-300 | NS | 10 | 8 | 80% | 20% |
| MRSA US-300 | vaccine | 10 | 2 | 20% | 80% |
| MRSA NEWMAN | NS | 10 | 8 | 80% | 20% |
| MRSA NEWMAN | vaccine | 10 | 2 | 20% | 80% |

As shown, the mice can be effectively infected by the method of the invention, and an animal pneumonia model infected by *Staphylococcus aureus* was successfully established. The mouse model was stable after infection, and suitable for researches, such as evaluation on the immunoprotection by the *Staphylococcus aureus* vaccine.

E. Dissociation of the Vaccine Formulation and Method for Antigen Content Detection During the research and development of the recombinant protein vaccines, the stability of antigen protein after adsorption by the adjuvant should be monitored, i.e., the antigen content in the finished vaccine product must be precisely determined. However, a finished vaccine product was typically a colloidal complex formed by adsorption of the antigen protein by the adjuvant. Accordingly, the difficulties that should be addressed for antigen content detection lied in how to make the protein dissociate from the adjuvant while retain its properties. At present, methods for dissociation between the protein and the adjuvant have been reported by using sodium citrate, or guanidinium hydrochloride, etc. However, problems, such as incomplete dissociation, and longer dissociation duration, etc., were often accompanied. Additionally, SDS-PAGE, ELISA, or HPLC etc would be commonly used for detecting the antigen content in a finished product of protein vaccine after dissociation between the antigen and the adjuvant. However, in the recombinant *Staphylococcus aureus* vaccine of the invention, the antigen components were complicated with similar molecular weights for several antigen proteins, so that the protein bands or peaks might overlap each other when detected by SDS-PAGE or HPLC, respectively, which would lead to inaccurate quantification. Furthermore, monoclonal antibodies for all 4 corresponding proteins would be required when detected by ELISA, resulting in higher cost and extended research period.

In term of the problems above, after intensive investigation, dissociation between the antigen protein and the adjuvant was implemented by the inventors in 10 min using a sodium carbonate solution. Meanwhile, western blot was performed for antigen standards of different concentrations and for the samples of the finished vaccine products after dissociation at the same time using the rabbit anti-serums against these 4 antigens; after development by enzymatic reaction, the grey-scale values for each band were detected by a scanner; a standard curve was established by correlating the grey-scale values to the antigen concentrations; the antigen contents in the finished product were calculated according to the regression equation. These methods could be used for quantification of an antigen in a finished vaccine product, and had advantages, such as easy operation, and good repeatability. At present, no related research has been reported yet.

In this section, the present invention provided a dissociation method for the *Staphylococcus aureus* vaccine formulation and a method for antigen content detection, which includes:

1) the dissociation solution: 1.5-2.5 M sodium carbonate solution

Method for dissociation: the dissociation solution was combined with the vaccine solution in a volume ratio of 0.5-2:1; and preferably, the concentration of the dissociation solution was 2 M, and the volume ratio between the dissociation solution and the vaccine solution was 1:1.

Taking the 4-component recombinant *Staphylococcus aureus* vaccine of the invention as an example, a dose of the finished vaccine product was centrifuged at 5000 rpm for 10 min at room temperature. Subsequently, a half volume of the supernatant was discarded, and the dissociation solution of the same volume was added. The mixture was then shaken at room temperature for 10 min. For example, if 600 μL of the finished vaccine product was taken out, 300 μL of the supernatant was discarded and another 300 μL of the dissociation solution was added.

2) detection of the antigen content: western blot was performed for antigen standards of different concentrations and for the samples of the finished products after dissociation at the same time using the anti-serums against various antigens; after development by enzymatic reaction, the grey-scale values for each band were detected by a scanner; a standard curve was established by correlating the grey-scale values to the antigen concentrations; the antigen contents in the finished product were calculated according to the regression equation.

Preferably, the finished vaccine product comprises the antigen and the adjuvant.

Preferably, the finished vaccine product comprises a plurality of antigens, such as 2, 3, 4, 5, or 6 antigens. More preferably, the antigens were selected from SpA5 protein, HI protein, mSEB protein, and MntC protein.

In another aspect, the present invention provided a kit for the method of the invention, which comprises: a dissociation solution and reagents for detecting the antigen content. Preferably, the dissociation solution was 1.5-2.5 M sodium carbonate solution; and more preferably, the dissociation solution was 2 M sodium carbonate solution; the reagents for detecting the antigen content were the reagents for western blot.

Using this method, rapid and complete dissociation between the antigen and the adjuvant could be achieved. Meanwhile, complex antigens in a finished vaccine product could be quantified. Accordingly, problems in the vaccine formulation assay, such as the dissociation and the antigen content detection in a finished product, were solved. The present invention was applicable to the dissociation and antigen content detection for the protein vaccines in the bio-pharmaceutical field.

The antigen proteins and various reagents used in this section were listed as follows:

1) Materials

Stock solutions of 4 antigens in the recombinant *Staphylococcus aureus* vaccine of the invention (SpA5 (KKAA), HI, MntC, and mSEB), with a concentration for each solution of 50 μg/ml;

In the finished 4-component recombinant *Staphylococcus aureus* vaccine product of the invention, the concentration for each component was 50 μg/ml;

Rabbit polyantiserums against 4 antigen components: New Zealand big ear white rabbits were immunized by the finished recombinant *Staphylococcus aureus* vaccine product based on the procedure of immunization on D0, D14, and D21 for 3 times, and the serums were obtained by blood collection on Day 14 after the last immunization.

2) Equipments

Water purification system (ELGA), electronic balance (Mettler Toledo), electrophoresis gel mould (BIORAD), protein gel imaging system (BIORAD), electrophoresis apparatus (BIORAD) and Semi-dried gel transfer apparatus (BIORAD).

3) Reagents

Trihydroxymethyl aminomethane (Tris), glycine, methanol, sodium chloride, hydrochloric acid, Tween 20, skimmed milk powder, DAB color developing reagent kit, 30% acrylamide, ammonium persulfate, 1.5 M Tris-HCl (pH 8.8), 10% SDS, 10% ammonium persulfate, TEMED, 1.0 M Tris-HCl (pH 6.8), 5× loading buffer, PVDF membrane (Milipore), and horse radish peroxidase-labled goat anti-rabbit IgG secondary antibody (BD corporation).

4) Preparation of Reagents

Dissociation solution: 2 M sodium carbonate solution;

Transfer buffer: 3.03 g Tris and 14.41 g glycine were added to 200 mL methanol, to which water was added to a final volume of 1 L. The solution was stored at 4° C.

10×TBS buffer: 24.228 g Tris and 87.75 g sodium chloride were dissolved in a suitable amount of water, and the pH value was adjusted to 7.5 using HCl, to which water was added to a final volume of 1 L. The solution was stored at 4° C.

TBST washing solution: 10×TBS buffer was diluted to 1×TBS buffer, to which 0.5% Tween 20 was added to prepare 1×TBST washing solution.

10×SDS-PAGE electrophoresis buffer: 3.03 g Tris, 14.41 g glycine and 1 g SDS were dissolved in ddH$_2$O, followed by adding ddH$_2$O to a final volume of 1 L.

Other solutions were prepared as described herein elsewhere.

Figure 59:
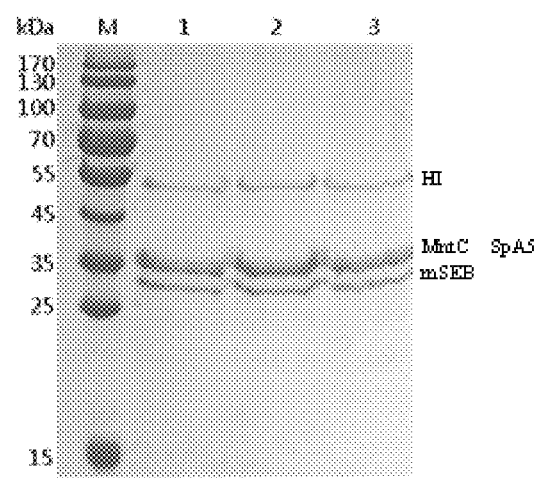
FIG. 59 is a graph that determines the dissociation time between the antigen and the adjuvant in Example 38; Lane M: protein molecular weight markers, and Lane 1, 2 and 3 showing the results at the dissociation time of 10, 20 and 30 min, respectively.

Example 39: Determination of the Dissociation Duration Between the Antigen and the Adjuvant Taking the recombinant *Staphylococcus aureus* vaccine as an example, 600 μl of the finished vaccine product in one dose was centrifuged at 5000 rpm for 10 min at room temperature. Subsequently, 300 μL of the supernatant was discarded, and subsequently 300 μL of the dissociation solution (2 M Na$_2$CO$_3$) was added. The mixture was then suspended at room temperature, and shaken for 10 min, 20 min and 30 min. After standing for 5 min, 40 μL supernatant was added to 10 μL 5× loading buffer, and subjected to SDS-PAGE. As shown in FIG. 59, after dissociation for 10 min, 20 min and 30 min, bands appeared on the gel with similar size, in a sequence from top to bottom of HI (48.2 kDa), MntC (32.9 kDa), SpA5 (32.7 kDa), and mSEB (28.1 kDa). The result indicated that there was no significant difference among various dissociation times. Accordingly, the dissociation time was determined as 10 min.

Figure 60:
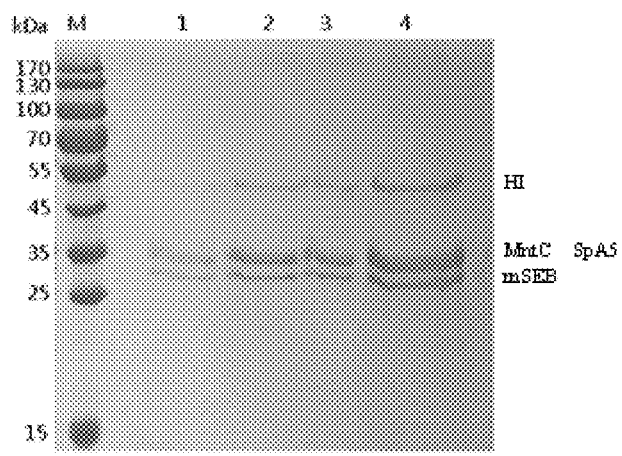
FIG. 60 is a graph showing the comparison between dissociation using sodium carbonate and other methods: Lane M: protein molecular weight markers, and Lane 1, 2, 3 and 4 representing dissociation using sodium citrate, guanidinium hydrochloride, citric acid and sodium carbonate, respectively.

Example 40: Comparison Between the Dissociation Method of the Invention and Other Methods The dissociation method of Example 39 was adopted in the present invention, with a dissociation duration of 10 min. The same procedure as described above was used for the control method, except for a varied formulation of the dissociation solution and different dissociation duration. There were 3 control methods, specifically as follows: (1) dissociation by 1 M sodium citrate at room temperature for 1 h; (2) dissociation by 2 M guanidinium hydrochloride at room temperature over night; (3) dissociation by 0.1 M citric acid at room temperature for 1 h. As shown in FIG. 60, more clear bands appeared on the gel for the sample dissociated by sodium carbonate, as compared with other methods, suggesting a more complete dissociation by this method. Additionally, what's more important was that the dissociation duration for the method of the invention was short, with simple operation. As indicated by these results, the method of the invention has more advantages over the reported methods.

Example 41: Detection of Antigen Content in a Finished Vaccine Product

Methods:
Preparation of the samples for electrophoresis: suitable amount of the stock antigen solution was diluted by ddH$_2$O to a concentration of 10 μg/ml, 30 μg/ml, 50 μg/ml, 70 μg/ml, and 90 μg/ml, to which a certain amount of 5× loading buffer was added to obtain 1× loading buffer. The samples were heated at 100° C. for 5 min. At the same time, one dose of finished vaccine product was taken, and 600 μL of the finished vaccine product was withdrawn to a 1.5 mL EP tube after mixed, and centrifugated at 5000 rpm for 10 min. 300 μL of the supernatant was discarded, and 300 μL 2 M Na$_2$CO$_3$ solution was added, and mixed. After becoming clear, the solution was centrifugated. Subsequently, to a suitable amount of supernatant, 5× loading buffer was added. The samples were then heated at 100° C. for 5 min.

SDS-PAGE: 20 μl samples of various antigen concentrations were loaded. The samples initially run at 80 v for 20 min, and then at 160 v until bromphenol blue was 0.5 cm away from the edge of glass plate.

Transfer: 2 pieces of filter paper was soaked in the transfer buffer, and a PVDF membrane was wetted by methanol. Transfer was conducted using a semi-dried gel transfer apparatus operated at 20 v for 20 min.

Blotting: after transfer, the PVDF membrane was washed by the TBST washing solution for 3 times, each for 10 min. The PVDF membrane was then placed in the blocking solution at 4° C. over night. Subsequently, the PVDF membrane was washed by the TBST washing solution for 3 times, each for 10 min. The self-made primary antibody (rabbit polyclonal antibody) was diluted in 1×TBS buffer for 5000 folds. The blocked PVDF membrane was then incubated in the primary antibody at 37° C. for 1 h. Subsequently, the PVDF membrane was washed by the TBST washing solution for 3 times, each for 10 min. The horse radish peroxidase-labeled goat anti rabbit secondary antibody was diluted in 1×TBS buffer for 5000 folds. Subsequently, the PVDF membrane was incubated in the secondary antibody at 37° C. for 40 min. The PVDF membrane was then washed by the TBST washing solution for 4 times, each for 10 min. Color developing was carried out according to the instructions of the DAB color developing reagent kit. After suitable developing, the reaction was stopped by washing with water. Evaluation on the results: the bands for the antigen standards should gradually become thicker. The grey-scale value was detected using a gel imaging system to establish a standard curve. The content of each antigen in the finished vaccine product was determined.

Figure 61:
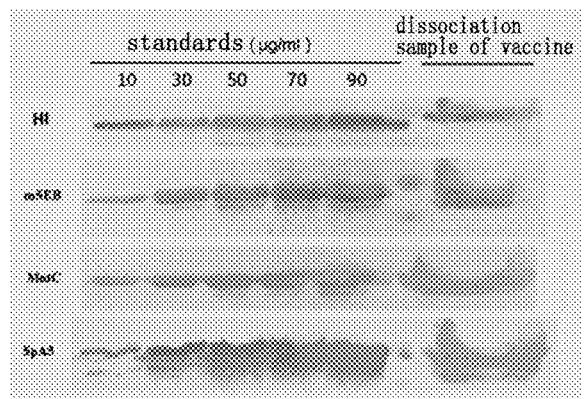
FIG. 61 shows the antigenicity of the vaccines detected by western-blot in Example 40.

Results: antigen standards of various concentrations (10 μg/ml, 30 μg/ml, 50 μg/ml, 70 μg/ml, and 90 μg/ml) were used as the control for western blot, as shown in FIG. 61. After an obvious color development reaction with the rabbit polyclonal antibody prepared using various antigens, a clear color band appeared at the position of corresponding molecular weight. With increased concentrations of each antigen, a clear size gradient was observed for the band.

Figure 62:
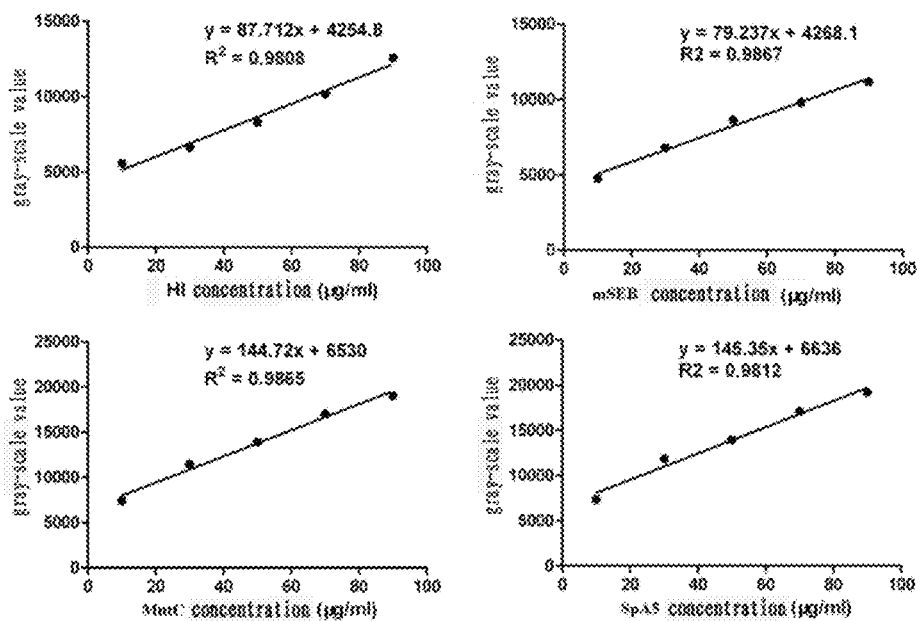
FIG. 62 is standard curves plotted between the concentrations of 4 standard antigens vs grey values in Example 40.

After scanning using a gel imaging system, the gray-scale values for each band were obtained, as listed in Table 41. Additionally, a standard curve was established between the gray-scale values and the antigen concentrations, as shown in FIG. 62. The results indicated that a clear linear correlation was observed between the gray-scale values of the western blot bands and their concentrations for each antigen standard, with a correlation coefficient $R^2$ larger than 0.98, which could be used for the antigen content detection in the finished vaccine product.

TABLE 41

Results of the gray-scale values of the western blot bands for different antigen standards

| Antigen concentration (μg/ml) | HI | mSEB | MntC | SpA5 |
| --- | --- | --- | --- | --- |
| 10 | 5553 | 4755 | 7375 | 7343 |
| 30 | 6645 | 6780 | 11442 | 11854 |
| 50 | 8281 | 8648 | 13910 | 13952 |
| 70 | 10151 | 9798 | 17071 | 17127 |
| 90 | 12571 | 11169 | 19033 | 19242 |

Using the same method, the gray-scale values of the western blot bands were determined for the dissociated samples of the finished vaccine product, and the contents of 4 antigens, including HI, mSEB, MntC, and SpA5, were determined as 46.03 μg/ml, 49.87 μg/ml, 48.82 μg/ml and 46.72 μg/ml, respectively, based on the equation in FIG. 62. The determined contents were close to their actual content of 50 μg/ml, and were within normal limits. In another aspect, the results also demonstrated that a complete dissociation could be implemented between the protein and the adjuvant using the established method of the invention. The above results also demonstrated that the antigen content in the finished vaccine product could be determined by the standard curve established using the gray-scale values of the western blot bands.

TABLE 42

Detection of the contents of 4 antigens in the finished vaccine product

| Type of antibody | HI | mSEB | MntC | SpA5 |
|---|---|---|---|---|
| Gray-scale value of the dissociated vaccine sample | 8292 | 8220 | 13596 | 13427 |
| Antigen content (μg/ml) | 46.03 | 49.87 | 48.82 | 46.72 |

F. Detection of the Bactericidal Antibody in the Serum

Example 42: Detection of the Antibody Serum-Mediated In Vitro Opsono-Phagocytosis Capacity of Staphylococcus aureus in the Rat Immunized by the Recombinant Staphylococcus aureus Vaccine An antibody bound to IgG FcR at the surface of the neutrophilic granulocyte through the Fc fragment of IgG (IgG1 and IgG3), and the Fc fragment of IgM bound to IgM FcR at the surface of the phagocyte by activating the complement system, which promoted the endocytosis and killing capacity of neutrophilic granulocyte and phagocyte against particulate antigens, such as bacteria etc.

1. Source of Antibody:
the rat serum of Example 30
2. List of Equipments
Incubator, superclean bench, low-speed centrifuge, low temperature refrigerated centrifuge, protein purification system, ultra-low temperature freezer, high & low temperature shaker (Thermo, Ilcermo 481), nucleic acid and protein analyzer (Smart Spec™ plus BD); OD tube (BD); and refrigerated centrifuge (Thermo scientific, SORVAIL ST40R Centrifuge).
3. Reagents
MH (A) bacteria culture plate; physiological saline; IMDM medium; fetal bovine serum (Gibco); $Ca^{2+}$, or $Mg^{2+}$ containing Hanks's solution (Gibco); $Ca^{2+}$, or $Mg^{2+}$ free Hanks's solution; RPMI-1640 culture solution (Gibco); dimethyl formamide (DMF); sterilized water; and PBS.
4. Procedure
4.1 Culture and Differentiation of HL-60 Cells (Human Promyelocytic Leukemia Cells, Supplied by Institute of Biochemistry and Cell Biology, SIBS, CAS)
HL-60 cells stably grew in IMDM (Gibco) culture medium containing 20% fetal bovine serum in a disposable cell culture bottle. Mature HL-60 cells were cultured at a concentration of $4 \times 10^5$ cell/mL in complete medium (IMDM+20% FBS) containing 0.8% DMF for differentiation for 4 days.
4.2 Preparation of the Working Seed Lot of MRSA252:
4.2.1 Culture and Cryopreservation of MRSA252
The bacteria were inoculated on an MHA solid plate by the tri-linear method, labeled, and incubated at 37° C. overnight. On the next day, single colony was picked up from the MHA solid plate, and inoculated to a flask containing 20 mL MHB medium. The flask was numbered and labeled, and placed in a shaker controlled at temperature of 37° C. shaken at a rotation rate of 220 rpm. Enlarged cultivation was conducted for 6 h. After detecting the concentration, bacteria were preserved by combining the bacteria suspension with 50% glycerol in a ratio of 1:1, and stored at −70° C.
4.2.2 Determination of the Working Dilution of the Cryopreserved Bacteria
500 μL cryopreserved working seed of MRSA252 was thawed in a water bath at 37□ and washed twice by the opsonophagocytosis buffer (Hanks's solution containing $Ca^{2+}$ and $Mg^{2+}$), and centrifugated at 12000 rpm for 2 min. The bacteria were suspended in 500 μl opsonophagocytosis buffer, and diluted in a series of eight 5-fold dilutions. 10 μl suspension was collected from each dilution, added to 8 individual wells of an U-bottom 96-well plate (containing 20 μl opsonophagocytosis buffer in each well), and cultured in a shaker at 700 rpm for 30 min.

40 μl of the differentiated HL-60 cell (concentration of $4 \times 10^5$ cell/ml), pre-washed twice by $Ca^{2+}$ and $Mg^{2+}$ containing Hanks's solution and $Ca^{2+}$ and $Mg^{2+}$ free Hanks's solution, was added to each well, and subsequently, 10 μl complement was added. The mixture was cultured at 37° C. in an atmosphere of 5% $CO_2$ in a shaker at 700 rpm for 45 min, and then placed in an ice bath for 20 min. Finally, it was smeared on an MHA plate. Based on the result of pre-experiment, an ideal colony count (120 CFU/Spot), i.e., the $5^{th}$ dilution, was selected as the working dilution.

4.3 Complement Collection and Screening:
The complement was harvested from the blood collected from the heart of newborn chinchilla rabbits (Experiment Animal Center, Third Military Medical), and stored at −70° C.

The complement stored at −70° C. was thawed at room temperature, deactivated in a water bath at 56° C. for 30 min, and stored at 4° C. for further use. Differentiated HL-60 cells were washed twice by the $Ca^{2+}$ and $Mg^{2+}$ containing Hanks's solution and the $Ca^{2+}$ and $Mg^{2+}$ free Hanks's solution (centrifugation at 1200 rpm for 5 min). A suitable amount of opsonophagocytosis buffer was added to a final cell concentration of $1 \times 10^7$ cell/ml, and the suspension was stored at root temperature for further use.

Cryopreserved working seed of MRSA252 was diluted in a series of eight 5-fold dilutions. At the same time, the same batch of cryopreserved complement was thawed at room temperature. 10 μl of the complement was each added to the first 8 wells, to which 40 μl of the differentiated HL-60 cell was added. Subsequently, to the last 8 wells, 10 μl of the deactivated complement and 40 μl of the differentiated HL-60 cells were added, and cultured at 37° C. in an atmosphere of 5% $CO_2$, at 700 rpm for 45 min. After maintained in an ice bath for 20 min, the samples were spotted. On the next day, the survival colonies were counted, and non-specific killing (NSK) of this batch of complement was calculated. Non-specific killing of the complement (%)=[Control B−Control A]/Control A]×100%. Wherein, Control A was the survival colony counts after incubation of MRSA with the heat-inactivated complement and HL-60 cells for 45 min, and Control B was the survival colony counts after incubation of MRSA with the complement and HL-60 cells for 45 min. Based on the experiment results, the non-specific killing of this batch of complement was 39%, which met the requirements of the experiment.

4.4 Opsonophagocytosis Test:
4.4.1 All test serums were deactivated in a water bath at 56° C. for 30 min, with 20 μl in each well. For the control well, the serum was substituted by 20 μl opsonophagocytosis buffer. To each well, 40 μl of the HL-60 cells, 10 μl of the complement, and 10 μl of the bacteria suspension were added and cultured at 37° C. in an atmosphere of 5% $CO_2$ at 700 rpm for 45 min. After maintained in an ice bath for 20 min, 10 μl suspension was collected and smeared on a plate. On the next day, the survival colonies were counted.
4.4.2 Counting: the colonies on the MHA plate were counted.
4.4.3 Statistics: the bactericidal rate by each antibody was calculated using the average colony counts on 3 plates. T test was adopted for comparison among groups.

5. Result Evaluation:

For the control group, the result was the survival colony counts after incubation of MRSA 252 with the complement and HL-60 cells.

For the experiment group, the result was the survival colony counts after incubation of MRSA 252 with the antibody, the complement and HL-60 cells.

Bactericidal rate by the antibody=[(control group−experiment group)/control group]×100%

6. Results:

TABLE 43

Individual data of bacteria-killing antibodies in the serum of rat immunized by repeated intramuscular injection of the recombinant *Staphylococcus aureus* vaccine

| Groups | No. | Sterilizing rate of the antibody in the immunized serum | | | | |
|---|---|---|---|---|---|---|
| | | D-1 | D14 | D21 | D28 | D57 |
| Negative control group | 13-2481 | — | — | died | | |
| | 13-2482 | — | — | — | 0.3% | — |
| | 13-2483 | — | — | — | — | — |
| | 13-2484 | — | — | — | — | — |
| | 13-2485 | — | — | 0.1% | — | 0.7% |
| | 13-2486 | — | — | — | — | — |
| | 13-2487 | — | — | — | — | 0.7% |
| | 13-2488 | — | — | — | — | — |
| | 13-2489 | — | — | — | — | — |
| | 13-2490 | — | — | — | 0.6% | — |
| Low dosage group of the test sample | 13-2491 | — | 0.4% | 7.4% | 28.5% | 41.2% |
| | 13-2492 | — | 0.7% | 1.8% | 29.6% | 33.5% |
| | 13-2493 | — | 1.8%- | 6.8% | 34.7% | 46.0% |
| | 13-2494 | — | — | 6.1% | 19.8% | 37.9% |
| | 13-2495 | — | 3.9% | 9.3% | 34.7% | 40.0% |
| | 13-2496 | — | — | 3.7% | 33.9% | 34.5% |
| | 13-2497 | — | — | 5.4% | 27.5% | 39.9% |
| | 13-2498 | — | — | 9.5% | 17.8% | 26.3% |
| | 13-2499 | — | 0.3% | 5.8% | 30.1% | 41.1% |
| | 13-2500 | — | — | 2.9% | 28.9% | 30.6% |
| Middle dosage group of the test sample | 13-2501 | — | 2.6% | 27.3% | 33.7% | 57.2% |
| | 13-2502 | — | 3.2% | 18.2% | 29.9% | 41.3% |
| | 13-2503 | 0.4% | 7.4% | 21.7% | 39.8% | 60.4% |
| | 13-2504 | — | 2.8% | 14.6% | 53.1% | 64.5% |
| | 13-2505 | — | 3.0% | 13.4% | 27.9% | 59.6% |
| | 13-2506 | — | 2.3% | 20.1% | 31.7% | 64.8% |
| | 13-2507 | — | 1.0% | 25.2% | 46.9% | 50.3% |
| | 13-2508 | — | 2.5% | 30.5% | 46.5% | 60.1% |
| | 13-2509 | — | 3.3% | 9.7% | 28.8% | 59.0% |
| | 13-2510 | — | 2.5% | 16.3% | 39.9% | 47.6% |
| High dosage group of the test sample | 13-2511 | — | 3.7% | 20.0% | 23.0% | 39.8% |
| | 13-2512 | — | 4.1% | 15.4% | 41.9% | 55.7% |
| | 13-2513 | — | 2.4% | 32.1% | 44.6% | 46.0% |
| | 13-2514 | 0.3% | 2.8% | 25.5% | 35.8% | 52.4% |
| | 13-2515 | — | 3.0% | 11.9% | 32.7% | 61.3% |
| | 13-2516 | 0.2% | 3.3% | 17.7% | 39.6% | 57.8% |
| | 13-2517 | — | 3.5% | 34.3% | 50.5% | 53.6% |
| | 13-2518 | — | 3.1% | 9.9% | 34.6% | 48.2% |
| | 13-2519 | — | 3.6% | 28.3% | 42.7% | 49.3% |
| | 13-2520 | — | 3.7% | 37.4% | 53.9% | 64.0% |

Note:
"—" represented a negative result of neutralizing antibody detection.

The dosages and the animal numbering in this table was as described in Table 18 of Example 30.

Apparent bactericidal activity was observed for the antibodies in the serum of rat after immunization by the vaccine.

Example 43: Detection of the Antibody Serum-Mediated In Vitro Opsono-Phagocytosis Capacity of *Staphylococcus aureus* in the Cynomolgus Monkey Immunized by the Recombinant *Staphylococcus aureus* Vaccine Source of antibody: the cynomolgus monkey serum of Example 31;

The experiment method was the same as described in Example 42.

TABLE 44

Individual data of bacteria-killing antibodies in the serum of cynomolgus monkey immunized by repeated intramuscular injection of the recombinant *Staphylococcus aureus* vaccine

| Groups | No. | Sterilizing rate of the antibody in the serum | |
|---|---|---|---|
| | | D14 | D28 |
| Low dosage group of the test sample | 13-4177 | 13.1% | 28.0% |
| | 13-4178 | 11.7% | 32.8% |
| | 13-4179 | 9.8% | 21.3% |
| | 13-4180 | 17.4% | 29.7% |
| | 13-4181 | 12.4% | 19.5% |
| | 13-4182 | 16.3% | 31.8% |
| | 13-4183 | 9.9% | 22.9% |
| | 13-4184 | 13.2% | 23.6% |
| Middle dosage group of the test sample | 13-4185 | 47.6% | 60.4% |
| | 13-4186 | 52.1% | 63.0% |
| | 13-4187 | 48.9% | 66.3% |
| | 13-4188 | 48.7% | 67.5% |
| | 13-4189 | 49.9% | 68.0% |
| | 13-4190 | 51.3% | 66.7% |
| | 13-4191 | 39.6% | 59.7% |
| | 13-4192 | 50.8* | 63.0% |
| High dosage group of the test sample | 13-4193 | 55.3% | 68.0% |
| | 13-4194 | 47.8% | 61.9% |
| | 13-4195 | 59.0% | 67.4% |
| | 13-4196 | 55.5% | 60.7% |
| | 13-4197 | 49.6% | 63.9% |
| | 13-4198 | 60.0% | 65.7% |
| | 13-4199 | 58.4% | 69.9% |
| | 13-4200 | 53.3% | 62.7% |

Note:
"—" represented a negative result of bactericidal antibody detection.

The dosages and the animal numbering in this table was as described in Table 27 of Example 31.

Apparent bactericidal activity was observed for the antibodies in the serum of cynomolgus monkey after immunization by the vaccine.

The invention claimed is:

1. A SpA5 protein, wherein the amino acid sequence of the protein is selected from any one of SEQ ID NO. 1-4.

2. An antibody generated by immunization using the SpA5 protein according to claim 1.

3. A composition comprising the SpA5 protein according to claim 1.

4. The composition according to claim 3, further comprising one or more of MntC, HI and mSEB protein.

5. The composition according to claim 4, wherein the amino acid sequence of the SpA5 protein is selected from any one of SEQ ID NO. 1-4; the amino acid sequence of MntC protein is shown in SEQ ID NO. 13; the amino acid sequence of mSEB protein is shown in SEQ ID NO. 14; and the amino acid sequence of HI protein is shown in SEQ ID NO. 15 the concentration of each protein is in the range from 10 to 100 μg/ml.

6. A method for preparation of the composition according to claim 3, comprising separately diluting an aluminum adjuvant and a SpA5 protein and mixing the diluted aluminum adjuvant with the diluted SpA5 protein.

7. The method according to claim 6, which comprises diluting the individual protein components by the formulation solution separately, mixing each solution with the aluminium adjuvant solution diluted by the formulation solution of the same volume, adsorbing separately, and mixing all the protein solutions together; or diluting the individual protein components by the vaccine diluent separately, mixing each solution with the diluted aluminium adjuvant solution of the same volume separately, mixing all the protein solutions, and adsorbing together; or mixing all protein components together, diluting them by the vaccine diluent and mixing well, mixing the solution with the diluted aluminium adjuvant solution of the same volume, and adsorbing.

8. The method according to claim 6, wherein the mixing mode for adsorption is vertical suspension or horizontal suspension at 14 rpm for adsorption of 1 h, at a temperature from 4-37° C., the weight ratio between the protein and the element aluminium is 1:1.98; and the aluminium adjuvant is aluminum phosphate or aluminium hydroxide.

9. The method according to claim 7, wherein the formulation solution is histidine buffer, comprising 10 mmol/L histidine, 0.02% poloxamer 188 and 0.9% sodium chloride, pH 6.0.

10. A method for immunizing against *Staphylococcus aureus* (SA) infections, comprising immunizing a subject in need thereof with an effective amount of the SpA5 protein according to claim 1.

11. The method according to claim 10, comprising immunizing the subject in need at the following time points: Day 0, Day 14, and Day 21; Day 0, Day 3, and Day 7; or Day 0, Day 3, Day 7, and Day 14.

12. A method for treatment of SA infections, comprising immunizing a subject in need thereof with an effective amount of the composition of claim 3.

13. The method according to claim 12, comprising immunizing the subject in need at the following time points: Day 0, Day 14, and Day 21; Day 0, Day 3, and Day 7; or Day 0, Day 3, Day 7, and Day 14.

* * * * *

SEQUENCE LISTING

<160> NUMBER OF SEQ ID NOS: 16

<210> SEQ ID NO 1
<211> LENGTH: 296
<212> TYPE: PRT
<213> ORGANISM: Artificial sequence
<220> FEATURE:

<223> OTHER INFORMATION: Recombinant SpA5(KKAA) protein

<400> SEQUENCE: 1

Gly Pro Leu Gly Ser Ala Gln His Asp Glu Ala Lys Lys Asn Ala Phe
1               5                   10                  15

Tyr Gln Val Leu Asn Met Pro Asn Leu Asn Ala Asp Gln Arg Asn Gly
                20                  25                  30

Phe Ile Gln Ser Leu Lys Ala Ala Pro Ser Gln Ser Ala Asn Val Leu
            35                  40                  45

Gly Glu Ala Gln Lys Leu Asn Asp Ser Gln Ala Pro Lys Ala Asp Ala
    50                  55                  60

Lys Lys Asn Lys Phe Asn Lys Asp Gln Gln Ser Ala Phe Tyr Glu Ile
65                  70                  75                  80

Leu Asn Met Pro Asn Leu Asn Glu Glu Gln Arg Asn Gly Phe Ile Gln
                85                  90                  95

Ser Leu Lys Ala Ala Pro Ser Gln Ser Thr Asn Val Leu Gly Glu Ala
            100                 105                 110

Lys Lys Leu Asn Glu Ser Gln Ala Pro Lys Ala Asp Asn Asn Phe Asn
        115                 120                 125

Lys Glu Lys Lys Asn Ala Phe Tyr Glu Ile Leu Asn Met Pro Asn Leu
    130                 135                 140

Asn Glu Glu Gln Arg Asn Gly Phe Ile Gln Ser Leu Lys Ala Ala Pro
145                 150                 155                 160

Ser Gln Ser Ala Asn Leu Leu Ala Glu Ala Lys Lys Leu Asn Glu Ser
                165                 170                 175

Gln Ala Pro Lys Ala Asp Asn Lys Phe Asn Lys Glu Lys Lys Asn Ala
            180                 185                 190

Phe Tyr Glu Ile Leu His Leu Pro Asn Leu Asn Glu Glu Gln Arg Asn
        195                 200                 205

Gly Phe Ile Gln Ser Leu Lys Ala Ala Pro Ser Gln Ser Ala Asn Leu
    210                 215                 220

Leu Ala Glu Ala Lys Lys Leu Asn Asp Ala Gln Ala Pro Lys Ala Asp
225                 230                 235                 240

Asn Lys Phe Asn Lys Glu Lys Lys Asn Ala Phe Tyr Glu Ile Leu His
                245                 250                 255

Leu Pro Asn Leu Thr Glu Glu Gln Arg Asn Gly Phe Ile Gln Ser Leu
            260                 265                 270

Lys Ala Ala Pro Ser Val Ser Lys Glu Ile Leu Ala Glu Ala Lys Lys
        275                 280                 285

Leu Asn Asp Ala Gln Ala Pro Lys
    290                 295

<210> SEQ ID NO 2
<211> LENGTH: 296
<212> TYPE: PRT
<213> ORGANISM: Artificial sequence
<220> FEATURE:
<223> OTHER INFORMATION: Recombinant SpA5(RRAA) protein

<400> SEQUENCE: 2

Gly Pro Leu Gly Ser Ala Gln His Asp Glu Ala Arg Arg Asn Ala Phe
1               5                   10                  15

Tyr Gln Val Leu Asn Met Pro Asn Leu Asn Ala Asp Gln Arg Asn Gly
                20                  25                  30

Phe Ile Gln Ser Leu Lys Ala Ala Pro Ser Gln Ser Ala Asn Val Leu
            35                  40                  45

Gly Glu Ala Gln Lys Leu Asn Asp Ser Gln Ala Pro Lys Ala Asp Ala
            50                  55                  60

Arg Arg Asn Lys Phe Asn Lys Asp Gln Gln Ser Ala Phe Tyr Glu Ile
 65                  70                  75                  80

Leu Asn Met Pro Asn Leu Asn Glu Glu Gln Arg Asn Gly Phe Ile Gln
                    85                  90                  95

Ser Leu Lys Ala Ala Pro Ser Gln Ser Thr Asn Val Leu Gly Glu Ala
                100                 105                 110

Lys Lys Leu Asn Glu Ser Gln Ala Pro Lys Ala Asp Asn Asn Phe Asn
                115                 120                 125

Lys Glu Arg Arg Asn Ala Phe Tyr Glu Ile Leu Asn Met Pro Asn Leu
            130                 135                 140

Asn Glu Glu Gln Arg Asn Gly Phe Ile Gln Ser Leu Lys Ala Ala Pro
145                 150                 155                 160

Ser Gln Ser Ala Asn Leu Leu Ala Glu Ala Lys Lys Leu Asn Glu Ser
                165                 170                 175

Gln Ala Pro Lys Ala Asp Asn Lys Phe Asn Lys Glu Arg Arg Asn Ala
                180                 185                 190

Phe Tyr Glu Ile Leu His Leu Pro Asn Leu Asn Glu Glu Gln Arg Asn
            195                 200                 205

Gly Phe Ile Gln Ser Leu Lys Ala Ala Pro Ser Gln Ser Ala Asn Leu
210                 215                 220

Leu Ala Glu Ala Lys Lys Leu Asn Asp Ala Gln Ala Pro Lys Ala Asp
225                 230                 235                 240

Asn Lys Phe Asn Lys Glu Arg Arg Asn Ala Phe Tyr Glu Ile Leu His
                245                 250                 255

Leu Pro Asn Leu Thr Glu Glu Gln Arg Asn Gly Phe Ile Gln Ser Leu
                260                 265                 270

Lys Ala Ala Pro Ser Val Ser Lys Glu Ile Leu Ala Glu Ala Lys Lys
                275                 280                 285

Leu Asn Asp Ala Gln Ala Pro Lys
        290                 295

<210> SEQ ID NO 3
<211> LENGTH: 296
<212> TYPE: PRT
<213> ORGANISM: Artificial sequence
<220> FEATURE:
<223> OTHER INFORMATION: Recombinant SpA5(KKVV) protein

<400> SEQUENCE: 3

Gly Pro Leu Gly Ser Ala Gln His Asp Glu Ala Lys Lys Asn Ala Phe
1               5                   10                  15

Tyr Gln Val Leu Asn Met Pro Asn Leu Asn Ala Asp Gln Arg Asn Gly
                20                  25                  30

Phe Ile Gln Ser Leu Lys Val Val Pro Ser Gln Ser Ala Asn Val Leu
            35                  40                  45

Gly Glu Ala Gln Lys Leu Asn Asp Ser Gln Ala Pro Lys Ala Asp Ala
            50                  55                  60

Lys Lys Asn Lys Phe Asn Lys Asp Gln Gln Ser Ala Phe Tyr Glu Ile
 65                  70                  75                  80

Leu Asn Met Pro Asn Leu Asn Glu Glu Gln Arg Asn Gly Phe Ile Gln
                    85                  90                  95

Ser Leu Lys Val Val Pro Ser Gln Ser Thr Asn Val Leu Gly Glu Ala
                100                 105                 110

```
Lys Lys Leu Asn Glu Ser Gln Ala Pro Lys Ala Asp Asn Asn Phe Asn
            115                 120                 125

Lys Glu Lys Lys Asn Ala Phe Tyr Glu Ile Leu Asn Met Pro Asn Leu
    130                 135                 140

Asn Glu Glu Gln Arg Asn Gly Phe Ile Gln Ser Leu Lys Val Val Pro
145                 150                 155                 160

Ser Gln Ser Ala Asn Leu Leu Ala Glu Ala Lys Lys Leu Asn Glu Ser
                165                 170                 175

Gln Ala Pro Lys Ala Asp Asn Lys Phe Asn Lys Glu Lys Lys Asn Ala
                180                 185                 190

Phe Tyr Glu Ile Leu His Leu Pro Asn Leu Asn Glu Glu Gln Arg Asn
                195                 200                 205

Gly Phe Ile Gln Ser Leu Lys Val Val Pro Ser Gln Ser Ala Asn Leu
            210                 215                 220

Leu Ala Glu Ala Lys Lys Leu Asn Asp Ala Gln Ala Pro Lys Ala Asp
225                 230                 235                 240

Asn Lys Phe Asn Lys Glu Lys Lys Asn Ala Phe Tyr Glu Ile Leu His
                245                 250                 255

Leu Pro Asn Leu Thr Glu Glu Gln Arg Asn Gly Phe Ile Gln Ser Leu
                260                 265                 270

Lys Val Val Pro Ser Val Ser Lys Glu Ile Leu Ala Glu Ala Lys Lys
            275                 280                 285

Leu Asn Asp Ala Gln Ala Pro Lys
            290                 295

<210> SEQ ID NO 4
<211> LENGTH: 296
<212> TYPE: PRT
<213> ORGANISM: Artificial sequence
<220> FEATURE:
<223> OTHER INFORMATION: Recombinant SpA5(RRVV) protein

<400> SEQUENCE: 4

Gly Pro Leu Gly Ser Ala Gln His Asp Glu Ala Arg Arg Asn Ala Phe
1               5                   10                  15

Tyr Gln Val Leu Asn Met Pro Asn Leu Asn Ala Asp Gln Arg Asn Gly
            20                  25                  30

Phe Ile Gln Ser Leu Lys Val Val Pro Ser Gln Ser Ala Asn Val Leu
        35                  40                  45

Gly Glu Ala Gln Lys Leu Asn Asp Ser Gln Ala Pro Lys Ala Asp Ala
    50                  55                  60

Arg Arg Asn Lys Phe Asn Lys Asp Gln Gln Ser Ala Phe Tyr Glu Ile
65                  70                  75                  80

Leu Asn Met Pro Asn Leu Asn Glu Glu Gln Arg Asn Gly Phe Ile Gln
                85                  90                  95

Ser Leu Lys Val Val Pro Ser Gln Ser Thr Asn Val Leu Gly Glu Ala
            100                 105                 110

Lys Lys Leu Asn Glu Ser Gln Ala Pro Lys Ala Asp Asn Asn Phe Asn
            115                 120                 125

Lys Glu Arg Arg Asn Ala Phe Tyr Glu Ile Leu Asn Met Pro Asn Leu
    130                 135                 140

Asn Glu Glu Gln Arg Asn Gly Phe Ile Gln Ser Leu Lys Val Val Pro
145                 150                 155                 160

Ser Gln Ser Ala Asn Leu Leu Ala Glu Ala Lys Lys Leu Asn Glu Ser
                165                 170                 175
```

```
Gln Ala Pro Lys Ala Asp Asn Lys Phe Asn Lys Glu Arg Arg Asn Ala
            180                 185                 190
Phe Tyr Glu Ile Leu His Leu Pro Asn Leu Asn Glu Glu Gln Arg Asn
        195                 200                 205
Gly Phe Ile Gln Ser Leu Lys Val Val Pro Ser Gln Ser Ala Asn Leu
    210                 215                 220
Leu Ala Glu Ala Lys Lys Leu Asn Asp Ala Gln Ala Pro Lys Ala Asp
225                 230                 235                 240
Asn Lys Phe Asn Lys Glu Arg Arg Asn Ala Phe Tyr Glu Ile Leu His
                245                 250                 255
Leu Pro Asn Leu Thr Glu Glu Gln Arg Asn Gly Phe Ile Gln Ser Leu
            260                 265                 270
Lys Val Val Pro Ser Val Ser Lys Glu Ile Leu Ala Glu Ala Lys Lys
        275                 280                 285
Leu Asn Asp Ala Gln Ala Pro Lys
    290                 295

<210> SEQ ID NO 5
<211> LENGTH: 516
<212> TYPE: PRT
<213> ORGANISM: Staphylococcus aureus

<400> SEQUENCE: 5

Met Lys Lys Lys Asn Ile Tyr Ser Ile Arg Lys Leu Gly Val Gly Ile
1               5                   10                  15
Ala Ser Val Thr Leu Gly Thr Leu Leu Ile Ser Gly Gly Val Thr Pro
            20                  25                  30
Ala Ala Asn Ala Ala Gln His Asp Glu Ala Gln Gln Asn Ala Phe Tyr
        35                  40                  45
Gln Val Leu Asn Met Pro Asn Leu Asn Ala Asp Gln Arg Asn Gly Phe
    50                  55                  60
Ile Gln Ser Leu Lys Asp Asp Pro Ser Gln Ser Ala Asn Val Leu Gly
65                  70                  75                  80
Glu Ala Gln Lys Leu Asn Asp Ser Gln Ala Pro Lys Ala Asp Ala Gln
                85                  90                  95
Gln Asn Lys Phe Asn Lys Asp Gln Gln Ser Ala Phe Tyr Glu Ile Leu
            100                 105                 110
Asn Met Pro Asn Leu Asn Glu Glu Gln Arg Asn Gly Phe Ile Gln Ser
        115                 120                 125
Leu Lys Asp Asp Pro Ser Gln Ser Thr Asn Val Leu Gly Glu Ala Lys
    130                 135                 140
Lys Leu Asn Glu Ser Gln Ala Pro Lys Ala Asp Asn Asn Phe Asn Lys
145                 150                 155                 160
Glu Gln Gln Asn Ala Phe Tyr Glu Ile Leu Asn Met Pro Asn Leu Asn
                165                 170                 175
Glu Glu Gln Arg Asn Gly Phe Ile Gln Ser Leu Lys Asp Asp Pro Ser
            180                 185                 190
Gln Ser Ala Asn Leu Leu Ala Glu Ala Lys Lys Leu Asn Glu Ser Gln
        195                 200                 205
Ala Pro Lys Ala Asp Asn Lys Phe Asn Lys Glu Gln Gln Asn Ala Phe
    210                 215                 220
Tyr Glu Ile Leu His Leu Pro Asn Leu Asn Glu Glu Gln Arg Asn Gly
225                 230                 235                 240
Phe Ile Gln Ser Leu Lys Asp Asp Pro Ser Gln Ser Ala Asn Leu Leu
```

```
                    245                 250                 255
Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
            325                 330                 335

Glu Asp Asn Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
            355                 360                 365

Glu Asp Asn Lys Lys Pro Gly Lys Glu Asp Gly Asn Lys Pro Gly Lys
            370                 375                 380

Glu Asp Gly Asn Lys Pro Gly Lys Glu Asp Gly Asn Lys Pro Gly Lys
385                 390                 395                 400

Glu Asp Gly Asn Lys Pro Gly Lys Glu Asp Gly Asn Lys Pro Gly Lys
            405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
            435                 440                 445

Asn Lys Leu Ala Asp Lys Asn Met Ile Lys Pro Gly Gln Glu Leu Val
            450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
            485                 490                 495

Phe Gly Gly Leu Ser Leu Ala Leu Gly Ala Ala Leu Leu Ala Gly Arg
            500                 505                 510

Arg Arg Glu Leu
        515

<210> SEQ ID NO 6
<211> LENGTH: 301
<212> TYPE: PRT
<213> ORGANISM: Artificial sequence
<220> FEATURE:
<223> OTHER INFORMATION: Comparison SpA5 mutantSpA5ref(KKAA) protein

<400> SEQUENCE: 6

Gly Pro Leu Gly Ser Ala Gln Ala Gln Gln Asn Gln His Asp Glu Ala
1               5                   10                  15

Lys Lys Asn Ala Phe Tyr Gln Val Leu Asn Met Pro Asn Leu Asn Ala
            20                  25                  30

Asp Gln Arg Asn Gly Phe Ile Gln Ser Leu Lys Ala Ala Pro Ser Gln
        35                  40                  45

Ser Ala Asn Val Leu Gly Glu Ala Gln Lys Leu Asn Asp Ser Gln Ala
    50                  55                  60

Pro Lys Ala Asp Ala Lys Lys Asn Asn Phe Asn Lys Asp Gln Gln Ser
65                  70                  75                  80

Ala Phe Tyr Glu Ile Leu Asn Met Pro Asn Leu Asn Glu Ala Gln Arg
```

```
                    85                  90                  95
Asn Gly Phe Ile Gln Ser Leu Lys Ala Ala Pro Ser Gln Ser Thr Asn
                100                 105                 110
Val Leu Gly Glu Ala Lys Lys Leu Asn Glu Ser Gln Ala Pro Lys Ala
                115                 120                 125
Asp Asn Asn Phe Asn Lys Glu Lys Lys Asn Ala Phe Tyr Glu Ile Leu
130                 135                 140
His Leu Pro Asn Leu Asn Glu Glu Gln Arg Asn Gly Phe Ile Gln Ser
145                 150                 155                 160
Leu Lys Ala Ala Pro Ser Gln Ser Ala Asn Leu Leu Ser Glu Ala Lys
                165                 170                 175
Lys Leu Asn Glu Ser Gln Ala Pro Lys Ala Asp Asn Lys Phe Asn Lys
                180                 185                 190
Glu Lys Lys Asn Ala Phe Tyr Glu Ile Leu His Leu Pro Asn Leu Asn
                195                 200                 205
Glu Glu Gln Arg Asn Gly Phe Ile Gln Ser Leu Lys Ala Ala Pro Ser
            210                 215                 220
Gln Ser Ala Asn Leu Leu Ala Glu Ala Lys Lys Leu Asn Asp Ala Gln
225                 230                 235                 240
Ala Pro Lys Ala Asp Asn Lys Phe Asn Lys Glu Lys Lys Asn Ala Phe
                245                 250                 255
Tyr Glu Ile Leu His Leu Pro Asn Leu Thr Glu Glu Gln Arg Asn Gly
                260                 265                 270
Phe Ile Gln Ser Leu Lys Ala Ala Pro Ser Val Ser Lys Glu Ile Leu
                275                 280                 285
Ala Glu Ala Lys Lys Leu Asn Asp Ala Gln Ala Pro Lys
                290                 295                 300

<210> SEQ ID NO 7
<211> LENGTH: 296
<212> TYPE: PRT
<213> ORGANISM: Artificial sequence
<220> FEATURE:
<223> OTHER INFORMATION: Recombinant SpA5 wild type protein (SpA5wt)

<400> SEQUENCE: 7

Gly Pro Leu Gly Ser Ala Gln His Asp Glu Ala Gln Gln Asn Ala Phe
1               5                   10                  15
Tyr Gln Val Leu Asn Met Pro Asn Leu Asn Ala Asp Gln Arg Asn Gly
                20                  25                  30
Phe Ile Gln Ser Leu Lys Asp Asp Pro Ser Gln Ser Ala Asn Val Leu
                35                  40                  45
Gly Glu Ala Gln Lys Leu Asn Asp Ser Gln Ala Pro Lys Ala Asp Ala
            50                  55                  60
Gln Gln Asn Lys Phe Asn Lys Asp Gln Gln Ser Ala Phe Tyr Glu Ile
65                  70                  75                  80
Leu Asn Met Pro Asn Leu Asn Glu Glu Gln Arg Asn Gly Phe Ile Gln
                85                  90                  95
Ser Leu Lys Asp Asp Pro Ser Gln Ser Thr Asn Val Leu Gly Glu Ala
                100                 105                 110
Lys Lys Leu Asn Glu Ser Gln Ala Pro Lys Ala Asp Asn Asn Phe Asn
                115                 120                 125
Lys Glu Gln Gln Asn Ala Phe Tyr Glu Ile Leu Asn Met Pro Asn Leu
130                 135                 140
Asn Glu Glu Gln Arg Asn Gly Phe Ile Gln Ser Leu Lys Asp Asp Pro
```

| | | | | | | | | | | | | |
|---|---|---|---|---|---|---|---|---|---|---|---|---|
| | 145 | | | 150 | | | 155 | | | 160 | | |

Ser Gln Ser Ala Asn Leu Leu Ala Glu Ala Lys Lys Leu Asn Glu Ser
                  165                170                175

Gln Ala Pro Lys Ala Asp Asn Lys Phe Asn Lys Glu Gln Gln Asn Ala
                  180                185                190

Phe Tyr Glu Ile Leu His Leu Pro Asn Leu Asn Glu Glu Gln Arg Asn
                  195                200                205

Gly Phe Ile Gln Ser Leu Lys Asp Asp Pro Ser Gln Ser Ala Asn Leu
    210                  215                220

Leu Ala Glu Ala Lys Lys Leu Asn Asp Ala Gln Ala Pro Lys Ala Asp
225                  230                235              240

Asn Lys Phe Asn Lys Glu Gln Gln Asn Ala Phe Tyr Glu Ile Leu His
                  245                250                255

Leu Pro Asn Leu Thr Glu Glu Gln Arg Asn Gly Phe Ile Gln Ser Leu
                  260                265                270

Lys Asp Asp Pro Ser Val Ser Lys Glu Ile Leu Ala Glu Ala Lys Lys
                  275                280                285

Leu Asn Asp Ala Gln Ala Pro Lys
    290                  295

<210> SEQ ID NO 8
<211> LENGTH: 5
<212> TYPE: PRT
<213> ORGANISM: Artificial sequence
<220> FEATURE:
<223> OTHER INFORMATION: From pGEX-6P-2 vector series

<400> SEQUENCE: 8

Gly Pro Leu Gly Ser
1             5

<210> SEQ ID NO 9
<211> LENGTH: 891
<212> TYPE: DNA
<213> ORGANISM: Artificial sequence
<220> FEATURE:
<223> OTHER INFORMATION: Encoding sequence of recombinant SpA5(KKAA)
    protein

<400> SEQUENCE: 9

```
gggcccctgg gatccgcgca acacgatgaa gctaaaaaaa atgctttta tcaagtgtta       60 aatatgccta acttaaacgc tgatcaacgt aatggtttta tccaaagcct taaagcagca      120
ccaagccaaa gtgctaacgt tttaggtgaa gctaaaaac ttaatgactc tcaagctcca       180
aaagctgatg cgaaaaaaaa taagttcaac aaagatcaac aaagcgcctt ctatgaaatc      240
ttgaacatgc taacttaaaa cgaagagcaa cgcaatggtt tcattcaaag tcttaaagca      300
gcaccaagcc aaagcactaa cgttttaggt gaagctaaaa aattaaacga atctcaagca      360
ccgaaagctg acaacaattt caacaaagaa aaaaaaatg ctttctatga atcttgaac        420 atgcctaact tgaacgaaga caacgcaat ggtttcatcc aaagcttaaa agcagcacca       480
agtcaaagtg ctaaccttt agcagaagct aaaaagttaa atgaatctca agcaccgaaa       540
gctgataaca aattcaacaa agaaaaaaaa atgctttct atgaaatctt acatttacct       600
aacttaaatg aagaacaacg caatggtttc atccaaagct aaaagcagc accaagccaa       660 agcgctaacc ttttagcaga agctaaaaag ctaaatgatg cacaagcacc aaaagctgac      720
aacaaattca caagaaaaa aaaaaatgct ttctatgaaa ttttacattt acctaactta       780
```

-continued

| actgaagaac aacgtaacgg cttcatccaa agccttaaag cagcaccttc agtgagcaaa | 840 |
| gaaattttag cagaagctaa aaagctaaac gatgctcaag caccaaaata a | 891 |

<210> SEQ ID NO 10
<211> LENGTH: 891
<212> TYPE: DNA
<213> ORGANISM: Artificial sequence
<220> FEATURE:
<223> OTHER INFORMATION: Encoding sequence of recombinant SpA5(RRAA)
      protein

<400> SEQUENCE: 10

| gggcccctgg gatccgcgca acacgatgaa gctcgccgca atgcttttta tcaagtgtta | 60 |
| aatatgccta acttaaacgc tgatcaacgt aatggtttta tccaaagcct taaagcagca | 120 |
| ccaagccaaa gtgctaacgt tttaggtgaa gctcaaaaac ttaatgactc tcaagctcca | 180 |
| aaagctgatg cgcgccgcaa taagttcaac aaagatcaac aaagcgcctt ctatgaaatc | 240 |
| ttgaacatgc ctaacttaaa cgaagagcaa cgcaatggtt tcattcaaag tcttaaagca | 300 |
| gcaccaagcc aaagcactaa cgttttaggt gaagctaaaa aattaaacga atctcaagca | 360 |
| ccgaaagctg acaacaattt caacaaagaa cgccgcaatg ctttctatga atcttgaac | 420 |
| atgcctaact tgaacgaaga caacgcaat ggtttcatcc aaagcttaaa agcagcacca | 480 |
| agtcaaagtg ctaaccttt agcagaagct aaaaagttaa atgaatctca agcaccgaaa | 540 |
| gctgataaca aattcaacaa agaacgccgc aatgctttct atgaaatctt acatttacct | 600 |
| aacttaaatg aagaacaacg caatggtttc atccaaagct aaaagcagc accaagccaa | 660 |
| agcgctaacc ttttagcaga agctaaaaag ctaaatgatg cacaagcacc aaaagctgac | 720 |
| aacaaattca caaagaacg ccgcaatgct ttctatgaaa ttttacattt acctaactta | 780 |
| actgaagaac aacgtaacgg cttcatccaa agccttaaag cagcaccttc agtgagcaaa | 840 |
| gaaattttag cagaagctaa aaagctaaac gatgctcaag caccaaaata a | 891 |

<210> SEQ ID NO 11
<211> LENGTH: 891
<212> TYPE: DNA
<213> ORGANISM: Artificial sequence
<220> FEATURE:
<223> OTHER INFORMATION: Encoding sequence of recombinant SpA5(KKVV)
      protein

<400> SEQUENCE: 11

| gggcccctgg gatccgcgca acacgatgaa gctaaaaaaa atgcttttta tcaagtgtta | 60 |
| aatatgccta acttaaacgc tgatcaacgt aatggtttta tccaaagcct taaagttgtt | 120 |
| ccaagccaaa gtgctaacgt tttaggtgaa gctcaaaaac ttaatgactc tcaagctcca | 180 |
| aaagctgatg cgaaaaaaaa taagttcaac aaagatcaac aaagcgcctt ctatgaaatc | 240 |
| ttgaacatgc ctaacttaaa cgaagagcaa cgcaatggtt tcattcaaag tcttaaagtt | 300 |
| gttccaagcc aaagcactaa cgttttaggt gaagctaaaa aattaaacga atctcaagca | 360 |
| ccgaaagctg acaacaattt caacaaagaa aaaaaaatg ctttctatga atcttgaac | 420 |
| atgcctaact tgaacgaaga caacgcaat ggtttcatcc aaagcttaaa agttgttcca | 480 |
| agtcaaagtg ctaaccttt agcagaagct aaaaagttaa atgaatctca agcaccgaaa | 540 |
| gctgataaca aattcaacaa agaaaaaaaa atgctttct atgaaatctt acatttacct | 600 |
| aacttaaatg aagaacaacg caatggtttc atccaaagct aaaagttgt tccaagccaa | 660 |
| agcgctaacc ttttagcaga agctaaaaag ctaaatgatg cacaagcacc aaaagctgac | 720 |

```
aacaaattca acaaagaaaa aaaaaatgct ttctatgaaa ttttacattt acctaactta    780
actgaagaac aacgtaacgg cttcatccaa agccttaaag ttgttccttc agtgagcaaa    840
gaaattttag cagaagctaa aaagctaaac gatgctcaag caccaaaata a             891
```

<210> SEQ ID NO 12
<211> LENGTH: 891
<212> TYPE: DNA
<213> ORGANISM: Artificial sequence
<220> FEATURE:
<223> OTHER INFORMATION: Encoding sequence of recombinant SpA5(RRVV) protein

<400> SEQUENCE: 12

```
gggcccctgg gatccgcgca acacgatgaa gctcgccgca atgcttttta tcaagtgtta     60
aatatgccta acttaaacgc tgatcaacgt aatggtttta tccaaagcct taaagttgtt    120
ccaagccaaa gtgctaacgt tttaggtgaa gctcaaaaac ttaatgactc tcaagctcca    180
aaagctgatg cgcgccgcaa taagttcaac aaagatcaac aaagcgcctt ctatgaaatc    240
ttgaacatgc taacttaaa cgaagagcaa cgcaatggtt tcattcaaag tcttaaagtt     300
gttccaagcc aaagcactaa cgttttaggt gaagctaaaa aattaaacga atctcaagca    360
ccgaaagctg acaacaattt caacaaagaa cgccgcaatg ctttctatga atcttgaac    420 atgcctaact tgaacgaaga acaacgcaat ggtttcatcc aaagcttaaa agttgttcca    480
agtcaaagtg ctaacctttt agcagaagct aaaaagttaa atgaatctca agcaccgaaa    540
gctgataaca aattcaacaa agaacgccgc aatgctttct atgaaatctt acatttacct    600
aacttaaatg aagaacaacg caatggtttc atccaaagct taaagttgt tccaagccaa    660 agcgctaacc ttttagcaga agctaaaaag ctaaatgatg cacaagcacc aaaagctgac    720
aacaaattca caaagaacg ccgcaatgct ttctatgaaa ttttacattt acctaactta    780
actgaagaac aacgtaacgg cttcatccaa agccttaaag ttgttccttc agtgagcaaa    840
gaaattttag cagaagctaa aaagctaaac gatgctcaag caccaaaata a             891
```

<210> SEQ ID NO 13
<211> LENGTH: 290
<212> TYPE: PRT
<213> ORGANISM: Artificial sequence
<220> FEATURE:
<223> OTHER INFORMATION: Recombinant MntC protein

<400> SEQUENCE: 13

```
Gly Pro Leu Gly Ser Ser Ser Asp Lys Ser Asn Gly Lys Leu Lys Val
1               5                   10                  15

Val Thr Thr Asn Ser Ile Leu Tyr Asp Met Ala Lys Asn Val Gly Gly
            20                  25                  30

Asp Asn Val Asp Ile His Ser Ile Val Pro Val Gly Gln Asp Pro His
        35                  40                  45

Glu Tyr Glu Val Lys Pro Lys Asp Ile Lys Lys Leu Thr Asp Ala Asp
    50                  55                  60

Val Ile Leu Tyr Asn Gly Leu Asn Leu Glu Thr Gly Asn Gly Trp Phe
65                  70                  75                  80

Glu Lys Ala Leu Glu Gln Ala Gly Lys Ser Leu Lys Asp Lys Lys Val
                85                  90                  95

Ile Ala Val Ser Lys Asp Val Lys Pro Ile Tyr Leu Asn Gly Glu Glu
            100                 105                 110
```

-continued

```
Gly Asn Lys Asp Lys Gln Asp Pro His Ala Trp Leu Ser Leu Asp Asn
        115                 120                 125

Gly Ile Lys Tyr Val Lys Thr Ile Gln Gln Thr Phe Ile Asp Asn Asp
    130                 135                 140

Lys Lys His Lys Ala Asp Tyr Glu Lys Gln Gly Asn Lys Tyr Ile Ala
145                 150                 155                 160

Gln Leu Glu Lys Leu Asn Asn Asp Ser Lys Asp Lys Phe Asn Asp Ile
                165                 170                 175

Pro Lys Glu Gln Arg Ala Met Ile Thr Ser Glu Gly Ala Phe Lys Tyr
            180                 185                 190

Phe Ser Lys Gln Tyr Gly Ile Thr Pro Gly Tyr Ile Trp Glu Ile Asn
        195                 200                 205

Thr Glu Lys Gln Gly Thr Pro Glu Gln Met Arg Gln Ala Ile Glu Phe
    210                 215                 220

Val Lys Lys His Lys Leu Lys His Leu Leu Val Glu Thr Ser Val Asp
225                 230                 235                 240

Lys Lys Ala Met Glu Ser Leu Ser Glu Glu Thr Lys Lys Asp Ile Phe
                245                 250                 255

Gly Glu Val Tyr Thr Asp Ser Ile Gly Lys Glu Gly Thr Lys Gly Asp
            260                 265                 270

Ser Tyr Tyr Lys Met Met Lys Ser Asn Ile Glu Thr Val His Gly Ser
        275                 280                 285

Met Lys
    290

<210> SEQ ID NO 14
<211> LENGTH: 240
<212> TYPE: PRT
<213> ORGANISM: Artificial sequence
<220> FEATURE:
<223> OTHER INFORMATION: Recombinant mSEB protein

<400> SEQUENCE: 14

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
            20                  25                  30

His Val Ser Ala Ile Asn Val Lys Ser Ile Asp Gln Phe Arg Tyr Phe
        35                  40                  45

Asp Leu Ile Tyr Ser Ile Lys Asp Thr Lys Leu Gly Asn Tyr Asp Asn
    50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Ala Tyr Tyr Gln Cys Ala Phe
                85                  90                  95

Ser Lys Lys Thr Asn Asp Ile Asn Ser His Gln Thr Asp Lys Arg Lys
            100                 105                 110

Thr Cys Met Tyr Gly Gly Val Thr Glu His Asn Gly Asn Gln Leu Asp
        115                 120                 125

Lys Tyr Arg Ser Ile Thr Val Arg Val Phe Glu Asp Gly Lys Asn Leu
    130                 135                 140

Leu Ser Phe Asp Val Gln Thr Asn Lys Lys Lys Val Thr Ala Gln Glu
145                 150                 155                 160

Leu Asp Tyr Leu Thr Arg His Tyr Leu Val Lys Asn Lys Lys Leu Tyr
                165                 170                 175
```

```
Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
        195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys Lys
225                 230                 235                 240

<210> SEQ ID NO 15
<211> LENGTH: 424
<212> TYPE: PRT
<213> ORGANISM: Artificial sequence
<220> FEATURE:
<223> OTHER INFORMATION: Recombinant HI protein

<400> SEQUENCE: 15

Gly Pro Leu Gly Ser Met Ala Asp Ser Asp Ile Asn Ile Lys Thr Gly
1               5                   10                  15

Thr Thr Asp Ile Gly Ser Asn Thr Thr Val Lys Thr Gly Asp Leu Val
            20                  25                  30

Thr Tyr Asp Lys Glu Asn Gly Met Leu Lys Lys Val Phe Tyr Ser Phe
        35                  40                  45

Ile Asp Asp Lys Asn His Asn Lys Lys Ile Leu Val Ile Arg Thr Lys
    50                  55                  60

Gly Thr Ile Ala Gly Gln Tyr Arg Val Tyr Ser Glu Glu Gly Ala Asn
65                  70                  75                  80

Lys Ser Gly Leu Ala Trp Pro Ser Ala Phe Lys Val Gln Leu Gln Leu
                85                  90                  95

Pro Asp Asn Glu Val Ala Gln Ile Ser Asp Tyr Tyr Pro Arg Asn Ser
            100                 105                 110

Ile Asp Thr Lys Glu Tyr Met Ser Thr Leu Thr Tyr Gly Phe Asn Gly
        115                 120                 125

Asn Val Thr Gly Asp Asp Ser Gly Lys Ile Gly Gly Leu Ile Gly Ala
130                 135                 140

Asn Val Ser Ile Gly His Thr Leu Lys Tyr Val Gln Pro Asp Phe Lys
145                 150                 155                 160

Thr Ile Leu Glu Ser Pro Thr Asp Lys Lys Val Gly Trp Lys Val Ile
                165                 170                 175

Phe Asn Asn Met Val Asn Gln Asn Trp Gly Pro Tyr Asp Arg Asp Ser
            180                 185                 190

Trp Asn Pro Val Tyr Gly Asn Gln Leu Phe Met Lys Thr Arg Asn Gly
        195                 200                 205

Ser Met Lys Ala Ala Glu Asn Phe Leu Asp Pro Asn Lys Ala Ser Ser
    210                 215                 220

Leu Leu Ser Ser Gly Phe Ser Pro Asp Phe Ala Thr Val Ile Thr Met
225                 230                 235                 240

Asp Arg Lys Ala Thr Lys Gln Gln Thr Asn Ile Asp Val Ile Tyr Glu
                245                 250                 255

Arg Val Arg Asp Asp Tyr Gln Leu His Trp Thr Ser Thr Asn Trp Lys
            260                 265                 270

Gly Thr Asn Thr Lys Asp Lys Trp Thr Asp Arg Ser Ser Glu Arg Tyr
        275                 280                 285

Lys Ile Asp Trp Glu Lys Glu Glu Met Thr Asn Gly Gly Gly Gly Ser
    290                 295                 300
```

-continued

```
Lys Met Thr Asp Leu Gln Asp Thr Lys Tyr Val Val Tyr Glu Ser Val
305                 310                 315                 320

Glu Asn Asn Glu Ser Met Met Asp Ala Phe Val Lys His Pro Ile Lys
                325                 330                 335

Thr Gly Met Leu Asn Gly Lys Lys Tyr Met Val Met Glu Thr Thr Asn
            340                 345                 350

Asp Asp Tyr Trp Lys Asp Phe Met Val Glu Gly Gln Arg Val Arg Thr
        355                 360                 365

Ile Ser Lys Asp Ala Lys Asn Asn Thr Arg Thr Ile Ile Phe Pro Tyr
    370                 375                 380

Val Glu Gly Lys Thr Leu Tyr Asp Ala Ile Val Lys Val His Val Lys
385                 390                 395                 400

Thr Ile Asp Tyr Asp Gly Gln Tyr His Val Arg Ile Val Asp Lys Glu
                405                 410                 415

Ala Phe Thr Lys Ala Asn Leu Glu
            420

<210> SEQ ID NO 16
<211> LENGTH: 15
<212> TYPE: DNA
<213> ORGANISM: Artificial sequence
<220> FEATURE:
<223> OTHER INFORMATION: Encoding sequence of amino acid fragment GPLGS
      from pGEX-6P-2

<400> SEQUENCE: 16
gggcccctgg gatcc                                                      15
```